US012673987B2

(12) United States Patent
Hotamisligil et al.

(10) Patent No.: US 12,673,987 B2

(45) Date of Patent: Jul. 7, 2026

(54) METHOD TO IDENTIFY COMPOUNDS USEFUL TO TREAT DYSREGULATED LIPOGENESIS, DIABETES, AND RELATED DISORDERS

(71) Applicant: President and Fellows of Harvard College, Cambridge, MA (US)

(72) Inventors: Gökhan S. Hotamisligil, Weston, MA (US); Kosei Eguchi, Brookline, MA (US)

(73) Assignee: President and Fellows of Harvard College

( * ) Notice: Subject to any disclaimer, the term of this patent is extended or adjusted under 35 U.S.C. 154(b) by 897 days.

(21) Appl. No.: 17/825,697

(22) Filed: May 26, 2022

(65) Prior Publication Data

US 2022/0411490 A1 Dec. 29, 2022

Related U.S. Application Data

(63) Continuation of application No. 16/708,015, filed on Dec. 9, 2019, now Pat. No. 11,345,748, which is a (Continued)

(51) Int. Cl.

*C07K 16/18* (2006.01)

*A61P 1/16* (2006.01)

(Continued)

(52) U.S. Cl.

CPC ................ *C07K 16/18* (2013.01); *A61P 1/16* (2018.01); *A61P 3/04* (2018.01); *A61P 3/10* (2018.01)

(58) Field of Classification Search

CPC ....... C07K 16/18; C07K 2317/76; A61P 3/10; G01N 2333/4703; G01N 2500/04; A61K 2039/505

See application file for complete search history.

(56) References Cited

U.S. PATENT DOCUMENTS

| | | | |
|---|---|---|---|
| 5,858,366 A | 1/1999 | Sodroski et al. | |
| 5,889,167 A | 3/1999 | Cascieri et al. | |

(Continued)

FOREIGN PATENT DOCUMENTS

| | | | |
|---|---|---|---|
| CN | 103665139 A | 3/2014 | |
| DE | 102006034607 | 7/2007 | |

(Continued)

OTHER PUBLICATIONS

Burak, M. Furkan, et al. "Development of a therapeutic monoclonal antibody that targets secreted fatty acid-binding protein aP2 to treat type 2 diabetes." Science translational medicine 7.319 (2015): 319ra205-319ra205. (Year: 2015).*

(Continued)

*Primary Examiner* — Bao-Thuy L Nguyen

*Assistant Examiner* — Christopher Evans

(74) *Attorney, Agent, or Firm* — Knowles Intellectual Property Strategies, LLC

(57) ABSTRACT

Provided herein are compounds, compositions, and methods of identifying compounds that neutralize the ability of the cannabinoid receptor type-1 (CB1) agonist 2-arachidonylglycerol (2-AG) in complex with its obligate binding partner adipocyte lipid binding protein (aP2) from agonizing CB1 signaling in peripheral tissues. Further provided herein are methods of treating a disorder associated with dysregulated or abnormal hepatic de novo lipogenesis and/or hepatic selective insulin resistance by inhibiting cannabinoid receptor type-1 (CB1) agonist 2-arachidonylglycerol (2-AG) in complex with its obligate binding partner adipocyte lipid binding protein (aP2) from binding and agonizing CB1.

6 Claims, 27 Drawing Sheets

Specification includes a Sequence Listing.

Related U.S. Application Data continuation of application No. PCT/US2018/036941, filed on Jun. 11, 2018.

(60) Provisional application No. 62/517,611, filed on Jun. 9, 2017.

(51) Int. Cl.

| | |
|---|---|
| ***A61P 3/04*** | (2006.01) |
| ***A61P 3/10*** | (2006.01) |

(56) References Cited

U.S. PATENT DOCUMENTS

| | | | | |
|---|---|---|---|---|
| 6,548,529 | B1 | 4/2003 | Robl et al. | |
| 7,358,254 | B2 | 4/2008 | Robl et al. | |
| 7,390,824 | B1 | 6/2008 | Robl et al. | |
| 7,906,117 | B2 | 3/2011 | Smith et al. | |
| 8,846,413 | B2 | 9/2014 | Ruzicka | |
| 9,062,104 | B2 | 6/2015 | Garcia-Martinez et al. | |
| 11,014,979 | B2 | 5/2021 | Hotamisligil et al. | |
| 2002/0035064 | A1 | 3/2002 | Robl et al. | |
| 2003/0040516 | A1 | 2/2003 | Sulsky et al. | |
| 2004/0010119 | A1 | 1/2004 | Guo et al. | |
| 2004/0110226 | A1 | 6/2004 | Lazar et al. | |
| 2009/0022659 | A1 | 1/2009 | Olson et al. | |
| 2009/0076033 | A1 | 3/2009 | Robl et al. | |
| 2010/0048408 | A1 | 2/2010 | Naiki et al. | |
| 2011/0312946 | A1 | 12/2011 | Seed et al. | |
| 2012/0134998 | A1 | 5/2012 | Hotamisligil et al. | |
| 2013/0302399 | A1 | 11/2013 | Feldhaus et al. | |
| 2015/0093769 | A1 | 4/2015 | Ruzicka | |
| 2016/0297874 | A1 | 10/2016 | Hotamisligil et al. | |
| 2016/0319003 | A1* | 11/2016 | Hotamisligil | A61P 3/04 |
| 2019/0161536 | A1 | 5/2019 | Hotamisligil et al. | |

FOREIGN PATENT DOCUMENTS

| | | | |
|---|---|---|---|
| WO | WO 2000/15229 | A1 | 3/2000 |
| WO | WO 2000/15230 | A1 | 3/2000 |
| WO | WO 2000/47734 | A1 | 8/2000 |
| WO | WO 2003/043624 | A1 | 5/2003 |
| WO | WO 2005113600 | A2 | 12/2005 |
| WO | WO-2009/014192 | A1 | 1/2009 |
| WO | WO 2010/057260 | A1 | 5/2010 |
| WO | WO 2010/102171 | A2 | 9/2010 |
| WO | WO 2011/091435 | A2 | 7/2011 |
| WO | WO 2014/093189 | A1 | 6/2014 |
| WO | WO 2014/210205 | A1 | 12/2014 |
| WO | WO 2016/044337 | A1 | 3/2016 |
| WO | WO 2017/058771 | A1 | 9/2016 |
| WO | WO-2018/005551 | A1 | 1/2018 |

OTHER PUBLICATIONS

US, U.S. Pat. No. 9,879,078 B2, U.S. Appl. No. 15/093,508, Hotamisligil et al., Jan. 30, 2018.

US, U.S. Pat. No. 10,160,798 B2, U.S. Appl. No. 15/143,162, Hotamisligil et al., Dec. 25, 2018.

US, U.S. Pat. No. 10,882,901 B2, U.S. Appl. No. 15/851,040, Hotamisligil et al., Jan. 5, 2021.

US, U.S. Pat. No. 11,014,979 B2, U.S. Appl. No. 16/197,066, Hotamisligil et al., May 25, 2021.

US, U.S. Pat. No. 11,345,748 B2, U.S. Appl. No. 16/708,015, Hotamisligil et al., May 31, 2022.

US, 2019/0135888 A1, U.S. Appl. No. 16/228,297, Hotamisligil et al., May 9, 2019.

US, 2021/0147527 A1, U.S. Appl. No. 17/102,329, Hotamisligil et al., May 20, 2021.

US, 2021/0171599 A1, U.S. Appl. No. 16/937,316, Hotamisligil et al., Jun. 10, 2021.

US, 2022/0089705 A1, U.S. Appl. No. 17/327,170, Hotamisligil et al., Mar. 24, 2022.

Almargo & Fransson, Frontier in Bioscience, 2008, 13, 1619-1633.

Banaszak et al., "Lipid-binding proteins: a family of fatty acid and retinoid transport proteins" Adv. Protein Chem., 1994, 45, 89-151.

Barf et al. "N-Benzyl-indolo carboxylic acids: Design and synthesis of potent and selective adipocyte fatty-acid binding protein (A-FABP) inhibitors" Bioorganic and Medicinal Chemistry Letters, Mar. 15, 2009; 19(6): 1745-1748.

Barutta et al., "Cannabinoid receptor 1 blockade ameliorates albuminuria in experimental diabetic nephropathy", Diabetes. 2010; 59: 1046-1054.

Baxa et al. "Human adipocyte lipid-binding protein: purification of the protein and cloning of its complementary DNA" Biochemistry, 1989: 28: 8683-8690.

Blanc et al. "Exosome release by reticulocytes—An integral part of the red blood cell differentiation system" Blood Cells, Molecules and Diseases, 2005; 35: 21-26.

Boord et al., "adipocyte fatty acid-binding protein, aP2, alters late atherosclerotic lesion formation in severe hypercholesterolemia", Arteriosclerosis Trhombo. Vasc. Bio., 2002, 22(10), 1686-1691.

Brand C L et al., "Immunonuetralization of endogenous glucagon with monoclonal glucagon antibody normalizes hyperglycemia in moderately streptozotocin-diabetic rats", Diabetologia, 1994, 34(10), 985-993, XP00908952; ISSN: 0012-186X.

Bronova et al., "Protection from radiation-induced pulmonary fibrosis by peripheral targeting of cannabinoid receptor-1", Am J Respir Cell Mol Biol. 2015; 53(4): 555-562.

Burak et al., "Development of a therapeutic monoclonal antibody that targets secreted fatty acid-binding protein a P2 to treat type 2 diabetes", 2015, 7(319) ww.sciencetranslationmedicine.org.

Burak, M.F., et al., "Chain L, Development of A Therapeutic Monoclonal Antibody Targeting Secreted Ap2 To Treat Type 2 Diabetes." PDB:5D8J_L deposited on Aug. 17, 2015 and released on Aug. 2, 2017, available at: https://www.ncbi.nlm.nih.gov/protein/5D8J_L.

Burak, M.F., et al., "Development of a monoclonal antibody targeting secreted aP2 to treat diabetes and fatty liver disease," PDB:5CON deposited on Jun. 12, 2015 and released on Jun. 24, 2015, available at: http://www.rcsb.org/pdb/explore/explore.do?structureId=5C0N.

Cabre et al., "Fatty acid binding protein 4 is increased in metabolic syndrome and with thiazolidinedione treatment in diabetic patients", Atherosclerosis, 2007, 195, e150-e158.

Cai et al. "Benzbromarone, an old uricosuric drug, inhibits human fatty acid binding protein 4 in vitro and lowers the blood glucose level in db/db mice" Acta Pharmacologica Sinica, 2013; 34: 1397-1402.

Cao et al. "Adipocyte lipid chaperone aP2 is a secreted adipokine regulating hepatic glucose production" Cell Metabolism, May 2013; 17(5); 768-778.

Cao et al. "Identification of a Lipokine, a Lipid Hormone Linking Adipose Tissue to Systemic Metabolism" Cell, Sep. 19, 2008: 134:933-944.

Cao et al., "Regulation of metabolic responses by adipocyte/macrophage fatty acid binding protein in leptin-deficient mice", Diabetes, 2006, 55, 1915-1922.

Cayman Chemical FABP4 Polyclonal Antibody product sheet (5 pages) downloaded on Sep. 30, 2015.

Chamow and Ashkanazi, TIBTECH, 1996, 14, 52-60.

Chen et al., "Enhancement and destruction of antibody function by somatic mutation: unequal occurrence is controlled by V gene combinatorial associations", The EMBO Journal, 1995, 14(12), 2784-2794, XP055530299, ISSN: 0261-4189, DOI: 10.1002/j.1460-2075.1995.tb07278.x.

Cinar et al., "Cannabinoid CB(1) receptor overactivity contributes to the pathogenesis of idiopathic pulmonary fibrosis", JCI insight, 2017, 2(8), e92281 https://doi.org/10.1172/jci.insight.

Colman P. M., "Effects of amino acid sequence changes on antibody-antigen interactions", Research in Immunology, Editions Scientifiques et Medicales Elsevier, FR, 1994, 145(1), 33-36, XP023944838, ISSN: 0923-2494, DOI: 10.1016/S0923-2494(9)80039-1.

DeFronzo "Insulin resistance, lipotoxicity, type 2 diabetes and atherosclerosis: the missing links. The Claude Brenard Lecture 2009" Diabetologia, 2010; 53: 1270-1287.

(56) References Cited

OTHER PUBLICATIONS

De Genst et al., Dev Comp Immunol, 2006, 30, 187-198.
De Luca et al., "Endocannabinoid 2-Arachidonoylglycerol Self-Administration by Sprague-Dawley Rats and Stimulation in vivo Dopamine Transmission in the Nucleus Accumbens Shell", Frontiers in Psychiatry, vol. 5, Oct. 17, 2014 (Oct. 17, 2014).
Distel et al. "Fatty Acid Regulation of Gene Expression: Transcriptional and Post-Transcriptional Mechanism" The Journal of Biological Chemistry; Mar. 25, 1992; 267(9): 5937-5941.
Erbay et al. "Reducing endoplasmic reticulum stress through a macrophage lipid chaperone alleviates atherosclerosis" Nature Medicine, Dec. 2009; 15(12): 1383-1391.
Etrunc et al., "Secretion of fatty acid binding protein aP2 from adipocytes through nonclassical pathway in response to adipocyte activity" Journal of Lipid Research, 2015, 56, 423-434.
European Search Report for PCT/US2017/039585 mailed on Feb. 18, 2020.
European Search Report for PCT/US2016/030303 mailed on Apr. 20, 2020.
Fu et al. "Oxidized LDL induces the expression of ALBP/aP2 mRNA and protein in human THP-1 macrophages" Journal of Lipid Research, 2000; 41: 2017-2023.
Furuhashi et al. "Adipocyte/Macrophage Fatty Acid-Binding Proteins Contribute to Metabolic Deterioration Through Actions in Both Macrophages and Adipocytes in Mice" J. Clin. Invest., Jul. 2008; 118(7): 2640-2650.
Furuhashi et al. "Serum Fatty Acid-Binding Protein 4 Is a Predictor of Cardiovascular Events in End-Stage Renal Disease" PLOS ONE, Nov. 2011; 6(11): e27356.
Furuhashi et al. "Treatment of diabetes and atherosclerosis by inhibiting fatty-acid-binding protein aP2" Nature, 2007; 447(21); 959-965.
Gillilan et al. "Structural Basis for Activation of Fatty Acid-binding Protein 4" J. Mol. Biol. 2007; 372:1246-1260.
Girona et al. "FABP4 Induces Vascular Smooth Muscle Cell Proliferation and Migration through a MAPK-Dependent Pathway" PloS ONE, Nov. 2013; 8(11): e81914.
Gorbenko et al. "Generation and Characterization of Monoclonal Antibodies against FABP4" Hybridoma, 2006; 25(2): 86-90.
Gorbenko et al. Identification of novel PTEN-binding partners: PTEN interaction with fatty acid binding protein FABP4. Mol Cell Biochem. Apr. 2010, vol. 337, No. 1-2, pp. 299-305. 42-65, 67-68 Especially abstract. para 2, p. 601 col. 1 para 2, p. 601 col. 2 para 1.
Hall et al. "USP7 Attenuates Hepatic Gluconoegenesis Through Modulation of FoxO1 Gene Promoter Occupancy" Mol. Endocrinol., Jun. 2014; 28(6): 912-924.
Hecker et al. "Heat Shock proteins as biomarkers for the rapid detection of brain and spinal cord ischemia: a review and comparison to other methods of detection in thoracic aneurysm repair" Cell Stress and Chaperones, 2011; 16: 119-131.
Hellberg et al. "X-ray crystallographic analysis of adipocyte fatty acid binding protein (aP2) modified with 4-hydroxy-2-nonenal" Protein Science, 2010; 19: 1480-1489.
Hertzel et al., "The mammalian fatty acid binding protein multigene family: molecular and genetic insight into function". Trends in Endocrinology and Metabolism, 2000, 11(5), 175-180.
Hertzel et al. "Identification and characterization of a small molecule inhibitor of Fatty Acid binding proteins" Journal of Medicinal Chemistry, Oct. 8, 2009; 52(19): 6024-6031.
Hoo et al. "Pharmacological inhibition of adipocyte fatty acid binding protein alleviates both acute liver injury and non-alcoholic steatohepatitis in mice" Journal of Hepatology, 2013; 58: 358-364.
Hotamisligil et al. Metabolic functions of FABPs-mechanisms and therapeutic implications Nat Rev Endocrinol. Oct. 15, 2015, vol. 11. No. 10 pp. 592-605, Especially p. 597 col. 1.
Hotamisligil et al. "Uncoupling of Obesity from Insulin Resistance Through a Targeted Mutation in aP2, the Adipocyte Fatty Acid Binding Protein" Science, Nov. 22, 1996; 274(5291): 1377-1379.
Howlett et al., "Endocannabinoid tone versus constitutive activity of cannabinoid receptors", Br J Pharmacol., 2011, 163(7),1329-43.
Hunt et al. "Adipocyte P2 gene: Developmental expression and homology of 5'-flanking sequences among fat cell-specific genes" PNAS, Jun. 1986; 83: 3786-3790.
Hunter-Lavin et al. "Hsp70 release from peripheral blood mononuclear cells" Biochemical and Biophysical Research Communications, Nov. 12, 2004; 324(2): 511-517.
International Search Report and Written Opinion for PCT/US17/36941 mailed Oct. 22, 2018.
Ishimura et al. "Circulating Levels of Fatty Acid-Binding Protein Family and Metabolic Phenotype in the General Population" PLUS ONE, Nov. 2013; 8(11): e81318.
Jack et al. "C-terminal binding protein: A metabolic sensor implicated in regulating adipogenesis" The International Journal of Biochemistry & Cell Biology, 2011; 43: 693-696.
Janiak et al., "Blockade of cannabinoid CB1 receptors improves renal function, metabolic profile, and increased survival of obese Zucker rats", Kidney Intl. 2007; 72: 1345-1357.
Joyner C J et al., "Development of a monoclonal antibody to the aP2 protein to identify adipocyte precursors in tumors of adipose differentiation", Pathology Research and Practice, 1999, 195(7), 461-466, XP002797422, ISSN: 0344-0338.
Kaess et al. "Cardiometabolic Correlates and Heritability of Fetuin-A, Retinol-Binding Protein 4, and Fatty-Acid Binding Protein 4 in the Framingham Heart Study" J. Clin. Endocrinol. Metab., Oct. 2012. 97(10): e1943-e1947.
Kajimura et al. "Regulation of the brown and white fat gene programs through a PRDM16/CtBP transcriptional complex" Genes & Development, 2008; 22: 1397-1409.
Karakas et al."Serum fatty acid binding protein 4, free fatty acids, and metabolic risk markers" Metabolism Clinical and Experimental, 2009; 58: 1002-1007.
Kashima et al. "Diagnostic utility of aP2/FABP4 expression in soft tissue tumors" Virchows Archiv., Apr. 2013; 462(4): 465-472.
Kussie, Ph et al., "A single engineered amino acid substituted changes antibody fine specificity", The Journal of Immunology, 1994, 152, 146-152, XP055530279.
LaLonde et al., "X-ray Crystallographic Structures of Adipocyte Lipid-Binding Protein Complexed with Palmitate and Hexadecanesulfonic Acid. Properties of Cavity Binding Sites" Biochemistry, 1994; 33: 4885-4895.
Lan et al. "Small-molecule inhibitors of FABP4/5 ameliorate dyslipidemia but not insulin resistance in mice with diet-induced obesity" Journal of Lipid Research, Apr. 2011; 52(4): 646-656.
Layne et al. "Role of macrophage-expressed adipocyte fatty acid binding protein in the development of accelerated atherosclerosis in hypercholesterolemic mice" The FASEB Journal, Dec. 2001; 15: 2733-2735.
Lecru et al., "Cannabinoid receptor 1 is a major mediator of renal fibrosis", Kidney International, vol. 88, Jan. 1, 2015 (Jan. 1, 2015).
Lehmann et al. "Discovery of inhibitors of human adipocyte fatty acid-binding protein, a potential type 2 diabetes arget" Bioorganic and Medicinal Chemistry Letters, Sep. 6, 2004; 14(17):4445-4448.
Lin et al. "Cannabinoid receptor 1 disturbance of PPARγ2 augments hyperglycemia induction of mesangial inflammation and fibrosis in renal glomeruli", J. Mol Med. 2012; 90(3): 72-84.
Lin et al. "Hormonal Regulation of Hepatic Glucose Production in Health and Disease" Cell Metabolism, Jul. 6, 2011; 14:9-19.
Maeda et al. "Adipocyte/Macrophage Fatty-Acid Bonding Proteins Control Integrated Metabolic Responses in Obesity and Diabetes" Cell Metab., Feb. 2005; 1:107-119.
Makowski et al. "Lack of Macrophage Fatty-Acid-Binding Protein aP2 Protects Mice Deficient in Apolipoprotein E Against Atherosclerosis" Nat. Med., Jun. 2001; 7(6):699-705.
Makowski et al. "The Fatty Acid-binding Protein, aP2, Coordinates Macrophage Cholesterol Trafficking and Inflammatory Activity" The Journal of Biological Chemistry, Apr. 1, 2005; 280(13): 12888-12895.
Marquart et al., "Inactivation of the cannabinoid receptor CB1 prevents leukocyte infiltration and experimental fibrosis", Arthritis Rheum. 2010; 62: 3467-3476.

(56) References Cited

OTHER PUBLICATIONS

Melki et al. "Expression of the adipocyte fatty acid-binding protein streptozotocin-diabetes: Effects of insulin deficiency and supplementation" Journal of Lipid Research, 1993; 34: 1527-1534.
Miao et al. "The mAb against adipocyte fatty acid-binding protein 2E4 attenuates the inflammation in the mouse model of high-fat diet-induced obesity via toll-like receptor 4 pathway" Molecular and Cellular Endocrinology, 2015; 403: 1-9.
Muniyappa et al., Am J Physiol. Endocrinol. Metab., 2008, 294, 15-16.
Nardini et al. "CtBP/BARS: a dual-function protein involved in transcription co-repression and Golgi membrane fission" the EMBO Journal, 2003; 22(12): 3122-3130.
Ozcan et al. "Chemical Chaperones Reduce ER Stress and Restore Glucose Homeostasis in a Mouse Model of Type 2 Diabetes" Science, Aug. 25, 2006; 313(5790): 1137-1140.
Paglialunga and Dehn, "Clinical assessment of hepatic de novo lipogenesis in non-alcoholic fatty liver disease" Lipids in Health and Disease (2016) 15:159; 2016.
PCT/US2018/036941, Invitation to pay additional fees and, where applicable, protest fee, mailed Aug. 28, 2018.
Ringom et al. "Substituted benzylamino-6-(trufluoromethyl)pyramidin-4(1H)-ones: a novel class of selective human A-ABP inhibitors" Bioorganic and Medicinal Chemistry Letters, 2004; 14: 4449-4452.
Rosen et al. "Adipocytes as Regulators of Energy Balance and Glucose Homeostasis" Nature, Dec. 14, 2006; 44:847-853.
Rudikoff et al., PNAS, 1982, 79, 1979-1983.
Saksi et al. "Low-Expression Variant of Fatty Acid-Binding Protein 4 Flavors Reduced Manifestations of Atherosclerotic Disease and Increased Plaque Stability" Circ. Cardiovasc. Genet., 2014; 7: 588-598.
Sanson et al., "Crystallographic study of FABP5 as an intracellular endocannabinoid transporter" Acta Crystallogr D Biol Crystallogr. Feb. 1, 2014; 70(Pt 2): 290-298.
Storch et al. "Structural and functional analysis of fatty acid-binding proteins" Journal of Lipid Research, 2009; 50:S126-S131.
Suh et al. "Serum AFBP levels are elevated in patients with nonalcoholic fatty liver disease" Scandinavian Journal of Gastroenterology, 2014; 49(8): 979-985.
Sulsky et al. "Potent and selective biphenyl azole inhibitors of adipocyte fatty acid binding protein (aFABP)" Bioorganic and Medicinal Chemistry Letters, Jun. 15, 2007; 17(12):351-3515.
Supplementary European Search Report for PCT/US2018/036941 mailed on Mar. 17, 2021.
Tuncman et al. "A genetic variant at the fatty acid-binding protein aP2 locus reduces the risk for hypertriglyceridemia, type 2 diabetes, and cardiovascular disease" PNAS, May 2, 2006; 103(18): 6970-6975.
Uysal et al. "Improved Glucose and Lipid Metabolism in Genetically Obese Mice Lacking aP2" Endocrinology, 2000; 141: 3388-3396.
Van Dongen et al. "Structure-based screening as applied to human FABP4: a highly efficient alternative to HTS for hit generation" Journal of the American Chemical Society, Oct. 9, 2002; 124(40): 11874-11880.
Vernochet et al. "C/EBPalpha and the Corepressors CtBP2 Regulate Repression of Select Visceral White Adipose Genes during Induction of the Brown Phenotype in White Adipocytes by Peroxisome Proliferator-Activated Receptor gamma Agonists" Molecular and Cellular Biology, Sep. 2009; 29(17) 4714-4728.
Von Eynatten et al. "Circulating Adipocyte Fatty Acid-Binding Protein Levels and Cardiovascular Morbidity and Mortality in Patients with Coronary Heart Disease—A 10-year Prospective Study" Arteriscler. Thromb. Vasc. Biol., Sep. 2012; 32: 2327-2335.
Won et al. "Oligopeptide complex for targeted non-viral gene delivery to adipocytes" Nature Materials, Dec. 2014; 13: 1157-1164.
Xu et al. "Adipocyte Fatty-Acid-Binding Protein is a Plasma Biomarker Closely Associated with Obesity and Metabolic Syndrome" Clinical Chemistry, 2006; 52(3): 405-413.
Xu et al. "Circulating Adipocyte-Fatty Acid Binding Protein Levels Predict the Development of the Metabolic Syndrome—A 5-year Prospective Study" Circulation, 2007, 115:1537-1543.
Xu et al. "The adipocyte lipid-binding protein at 1.6-A resolution. Crystal structures of the apoprotein and with bound saturated and unsaturated fatty acids" Journal of Biological Chemistry, 1993; 268: 7874-7884.
Yoo et al, "Serum Adipocyte Fatty Acid-Binding Protein Is Associated Independently with Vascular Inflammation: Analysis with 18F-Fluorodeoxyglucose Positron Emission Tomography" J. Clin. Endocrinol. Metab., Mar. 2011; 96(3): E488-E492.
Zhang et al. "Exosomes" a novel pathway to local and distant intercellular communication that facilitates the growth and metastasis of neoplastic lesions "American Journal of Pathology, Jan. 2014; 184(1)" 28-41.
US, U.S. Pat. No. 11,685,774 B2, U.S. Appl. No. 17/102,329, Hotamisligil et al., Jun. 27, 2023.
US, 2023/0203142 A1, U.S. Appl. No. 17/983,098, Hotamisligil et al., Jun. 29, 2023.
US, 2024/0209072 A1, U.S. Appl. No. 18/341,404, Hotamisligil et al., Jun. 27, 2024.
U.S. Pat. No. 12,247,068 B2, Mar. 11, 2025, Hotamisligil et al., U.S. Appl. No. 17/327,170.
U.S. Pat. No. 12,454,569 B2, Oct. 28, 2025, Hotamisligil et al., U.S. Appl. No. 18/341,404.
US-2025/0346654-A1, Nov. 13, 2025, Hotamisligil et al., U.S. Appl. No. 19/075,616.
US-2025/0346646-A1, Nov. 13, 2025, Hotamisligil et al., U.S. Appl. No. 19/094,546.
Burak, M.F. et al., "Chain D, Development of a Monoclonal Antibody Targeting Secreted Ap2 To Treat Diabetes And Fatty Liver Disease." PDB:5CON_D deposited on Jun. 12, 2015 and released on Jan. 13, 2016, available at: www.ncbi.nlm.nih.gov/protein/5C0N_D, Jun. 12, 2015.

* cited by examiner

SEQUENCE LISTING

```
<160> NUMBER OF SEQ ID NOS: 52

<210> SEQ ID NO 1
<211> LENGTH: 132
<212> TYPE: PRT
<213> ORGANISM: Homo sapiens

<400> SEQUENCE: 1

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
            20                  25                  30

Val Ala Gly Met Ala Lys Pro Asn Met Ile Ile Ser Val Asn Gly Asp
        35                  40                  45

Val Ile Thr Ile Lys Ser Glu Ser Thr Phe Lys Asn Thr Glu Ile Ser
    50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
                85                  90                  95

Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
        115                 120                 125
```

```
Tyr Glu Arg Ala
    130


<210> SEQ ID NO 2
<211> LENGTH: 132
<212> TYPE: PRT
<213> ORGANISM: Mus musculus

<400> SEQUENCE: 2

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
            20                  25                  30

Val Ala Gly Met Ala Lys Pro Asn Met Ile Ile Ser Val Asn Gly Asp
        35                  40                  45

Leu Val Thr Ile Arg Ser Glu Ser Thr Phe Lys Asn Thr Glu Ile Ser
    50                  55                  60

Phe Lys Leu Gly Val Glu Phe Asp Glu Ile Thr Ala Asp Asp Arg Lys
65                  70                  75                  80

Val Lys Ser Ile Ile Thr Leu Asp Gly Gly Ala Leu Val Gln Val Gln
                85                  90                  95

Lys Trp Asp Gly Lys Ser Thr Thr Ile Lys Arg Lys Arg Asp Gly Asp
            100                 105                 110

Lys Leu Val Val Glu Cys Val Met Lys Gly Val Thr Ser Thr Arg Val
        115                 120                 125

Tyr Glu Arg Ala
    130


<210> SEQ ID NO 3
<211> LENGTH: 11
<212> TYPE: PRT
<213> ORGANISM: Artificial Sequence
<220> FEATURE:
<223> OTHER INFORMATION: aP2 nuclear localization amino acid sequence

<400> SEQUENCE: 3

Lys Glu Val Gly Val Gly Phe Ala Thr Arg Lys
1               5                   10


<210> SEQ ID NO 4
<211> LENGTH: 450
<212> TYPE: PRT
<213> ORGANISM: Artificial Sequence
<220> FEATURE:
<223> OTHER INFORMATION: 909gH62 IgG4 VH + human gamma-4P constant

<400> SEQUENCE: 4

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

Arg Pro Asp Asn Glu Gly Thr Ser Gly Tyr Leu Ser Gly Phe Gly Leu
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Lys Thr Tyr Thr Cys Asn Val
195 200 205

Asp His Lys Pro Ser Asn Thr Lys Val Asp Lys Arg Val Glu Ser Lys
210 215 220

Tyr Gly Pro Pro Cys Pro Pro Cys Pro Ala Pro Glu Phe Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser Gln Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Arg Leu Thr Val Asp
405 410 415

Lys Ser Arg Trp Gln Glu Gly Asn Val Phe Ser Cys Ser Val Met His
420 425 430

Glu Ala Leu His Asn His Tyr Thr Gln Lys Ser Leu Ser Leu Ser Leu
435 440 445

Gly Lys
450

<210> SEQ ID NO 5
<211> LENGTH: 399
<212> TYPE: DNA
<213> ORGANISM: Homo sapiens

<400> SEQUENCE: 5
atgtgtgatg cttttgtagg tacctggaaa cttgtctcca gtgaaaactt tgatgattat 60

```
atgaaagaag taggagtggg ctttgccacc aggaaagtgg ctggcatggc caaacctaac    120

atgatcatca gtgtgaatgg ggatgtgatc accattaaat ctgaaagtac ctttaaaaat    180

actgagattt ccttcatact gggccaggaa tttgacgaag tcactgcaga tgacaggaaa    240

gtcaagagca ccataacctt agatgggggt gtcctggtac atgtgcagaa atgggatgga    300

aaatcaacca ccataaagag aaaacgagag gatgataaac tggtggtgga atgcgtcatg    360

aaaggcgtca cttccacgag agtttatgag agagcataa                            399
```

<210> SEQ ID NO 6
<211> LENGTH: 399
<212> TYPE: DNA
<213> ORGANISM: Mus musculus

<400> SEQUENCE: 6

```
atgtgtgatg cctttgtggg aacctggaag cttgtctcca gtgaaaactt cgatgattac     60

atgaaagaag tgggagtggg ctttgccaca aggaaagtgg caggcatggc caagcccaac    120

atgatcatca gcgtaaatgg ggatttggtc accatccggt cagagagtac ttttaaaaac    180

accgagattt ccttcaaact gggcgtggaa ttcgatgaaa tcaccgcaga cgacaggaag    240

gtgaagagca tcataaccct agatggcggg gccctggtgc aggtgcagaa gtgggatgga    300

aagtcgacca caataaagag aaaacgagat ggtgacaagc tggtggtgga atgtgttatg    360

aaaggcgtga cttccacaag agtttatgaa agggcatga                            399
```

<210> SEQ ID NO 7
<211> LENGTH: 11
<212> TYPE: PRT
<213> ORGANISM: Artificial Sequence
<220> FEATURE:
<223> OTHER INFORMATION: CDRL1

<400> SEQUENCE: 7

```
Gln Ala Ser Glu Asp Ile Ser Arg Tyr Leu Val
1               5                   10
```

<210> SEQ ID NO 8
<211> LENGTH: 7
<212> TYPE: PRT
<213> ORGANISM: Artificial Sequence
<220> FEATURE:
<223> OTHER INFORMATION: CDRL2

<400> SEQUENCE: 8

```
Lys Ala Ser Thr Leu Ala Ser
1               5
```

<210> SEQ ID NO 9
<211> LENGTH: 14
<212> TYPE: PRT
<213> ORGANISM: Artificial Sequence
<220> FEATURE:
<223> OTHER INFORMATION: CDRL3

<400> SEQUENCE: 9

```
Gln Cys Thr Tyr Gly Thr Tyr Ala Gly Ser Phe Phe Tyr Ser
1               5                   10
```

<210> SEQ ID NO 10
<211> LENGTH: 14
<212> TYPE: PRT
<213> ORGANISM: Artificial Sequence

```
<220> FEATURE:
<223> OTHER INFORMATION: CDRL3 variant 1

<400> SEQUENCE: 10

Gln Ala Thr Tyr Gly Thr Tyr Ala Gly Ser Phe Phe Tyr Ser
1               5                   10


<210> SEQ ID NO 11
<211> LENGTH: 14
<212> TYPE: PRT
<213> ORGANISM: Artificial Sequence
<220> FEATURE:
<223> OTHER INFORMATION: CDRL3 variant 2

<400> SEQUENCE: 11

Gln Gln Thr Tyr Gly Thr Tyr Ala Gly Ser Phe Phe Tyr Ser
1               5                   10


<210> SEQ ID NO 12
<211> LENGTH: 14
<212> TYPE: PRT
<213> ORGANISM: Artificial Sequence
<220> FEATURE:
<223> OTHER INFORMATION: CDRL3 variant 3

<400> SEQUENCE: 12

Gln His Thr Tyr Gly Thr Tyr Ala Gly Ser Phe Phe Tyr Ser
1               5                   10


<210> SEQ ID NO 13
<211> LENGTH: 9
<212> TYPE: PRT
<213> ORGANISM: Artificial Sequence
<220> FEATURE:
<223> OTHER INFORMATION: CDRL3 variant 4

<400> SEQUENCE: 13

Gln Gln Ala Ser His Tyr Pro Leu Thr
1               5


<210> SEQ ID NO 14
<211> LENGTH: 10
<212> TYPE: PRT
<213> ORGANISM: Artificial Sequence
<220> FEATURE:
<223> OTHER INFORMATION: CDRH1

<400> SEQUENCE: 14

Gly Phe Ser Leu Ser Thr Tyr Tyr Met Ser
1               5                   10


<210> SEQ ID NO 15
<211> LENGTH: 10
<212> TYPE: PRT
<213> ORGANISM: Artificial Sequence
<220> FEATURE:
<223> OTHER INFORMATION: CDRH1 variant 1

<400> SEQUENCE: 15

Gly Tyr Thr Phe Thr Ser Asn Ala Ile Thr
1               5                   10


<210> SEQ ID NO 16
<211> LENGTH: 16
<212> TYPE: PRT
<213> ORGANISM: Artificial Sequence
<220> FEATURE:
```

-continued

```
<223> OTHER INFORMATION: CDRH2

<400> SEQUENCE: 16

Ile Ile Tyr Pro Ser Gly Ser Thr Tyr Cys Ala Ser Trp Ala Lys Gly
1               5                   10                  15


<210> SEQ ID NO 17
<211> LENGTH: 16
<212> TYPE: PRT
<213> ORGANISM: Artificial Sequence
<220> FEATURE:
<223> OTHER INFORMATION: CDRH2 variant 1

<400> SEQUENCE: 17

Ile Ile Tyr Pro Ser Gly Ser Thr Tyr Ser Ala Ser Trp Ala Lys Gly
1               5                   10                  15


<210> SEQ ID NO 18
<211> LENGTH: 17
<212> TYPE: PRT
<213> ORGANISM: Artificial Sequence
<220> FEATURE:
<223> OTHER INFORMATION: CDRH2 variant 2

<400> SEQUENCE: 18

Asp Ile Ser Pro Gly Ser Gly Ser Thr Thr Asn Asn Glu Lys Phe Lys
1               5                   10                  15

Ser


<210> SEQ ID NO 19
<211> LENGTH: 15
<212> TYPE: PRT
<213> ORGANISM: Artificial Sequence
<220> FEATURE:
<223> OTHER INFORMATION: CDRH3

<400> SEQUENCE: 19

Pro Asp Asn Asp Gly Thr Ser Gly Tyr Leu Ser Gly Phe Gly Leu
1               5                   10                  15


<210> SEQ ID NO 20
<211> LENGTH: 15
<212> TYPE: PRT
<213> ORGANISM: Artificial Sequence
<220> FEATURE:
<223> OTHER INFORMATION: CDRH3 variant 1

<400> SEQUENCE: 20

Pro Asp Asn Glu Gly Thr Ser Gly Tyr Leu Ser Gly Phe Gly Leu
1               5                   10                  15


<210> SEQ ID NO 21
<211> LENGTH: 10
<212> TYPE: PRT
<213> ORGANISM: Artificial Sequence
<220> FEATURE:
<223> OTHER INFORMATION: CDRH3 variant 2

<400> SEQUENCE: 21

Leu Arg Gly Phe Tyr Asp Tyr Phe Asp Phe
1               5                   10


<210> SEQ ID NO 22
<211> LENGTH: 12
<212> TYPE: PRT
<213> ORGANISM: Artificial Sequence
```

<220> FEATURE:
<223> OTHER INFORMATION: CDRL1 variant 1

<400> SEQUENCE: 22

Ser Val Ser Ser Ser Ile Ser Ser Ser Asn Leu His
1 5 10

<210> SEQ ID NO 23
<211> LENGTH: 7
<212> TYPE: PRT
<213> ORGANISM: Artificial Sequence
<220> FEATURE:
<223> OTHER INFORMATION: CDRL2 variant 1

<400> SEQUENCE: 23

Gly Thr Ser Asn Leu Ala Ser
1 5

<210> SEQ ID NO 24
<211> LENGTH: 9
<212> TYPE: PRT
<213> ORGANISM: Artificial Sequence
<220> FEATURE:
<223> OTHER INFORMATION: CDRL3 variant 5

<400> SEQUENCE: 24

Gln Gln Trp Ser His Tyr Pro Leu Thr
1 5

<210> SEQ ID NO 25
<211> LENGTH: 10
<212> TYPE: PRT
<213> ORGANISM: Artificial Sequence
<220> FEATURE:
<223> OTHER INFORMATION: CDRH1 variant 2

<400> SEQUENCE: 25

Gly Tyr Thr Phe Thr Ser Asn Trp Ile Thr
1 5 10

<210> SEQ ID NO 26
<211> LENGTH: 17
<212> TYPE: PRT
<213> ORGANISM: Artificial Sequence
<220> FEATURE:
<223> OTHER INFORMATION: CDRH2 variant 3

<400> SEQUENCE: 26

Asp Ile Tyr Pro Gly Ser Gly Ser Thr Thr Asn Asn Glu Lys Phe Lys
1 5 10 15

Ser

<210> SEQ ID NO 27
<211> LENGTH: 11
<212> TYPE: PRT
<213> ORGANISM: Artificial Sequence
<220> FEATURE:
<223> OTHER INFORMATION: CDRH3 variant 3

<400> SEQUENCE: 27

Leu Arg Gly Tyr Tyr Asp Tyr Phe Asp Phe Trp
1 5 10

<210> SEQ ID NO 28
<211> LENGTH: 112
<212> TYPE: PRT

```
<213> ORGANISM: Artificial Sequence
<220> FEATURE:
<223> OTHER INFORMATION: Rabbit Ab 909 VL-region

<400> SEQUENCE: 28

Asp Val Val Met Thr Gln Thr Pro Ala Ser Val Ser Glu Pro Val Gly
1               5                   10                  15

Gly Thr Val Thr Ile Lys Cys Gln Ala Ser Glu Asp Ile Ser Arg Tyr
            20                  25                  30

Leu Val Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Asp Asp Ala Ala Thr Tyr Tyr Cys Gln Cys Thr Tyr Gly Thr Tyr Ala
                85                  90                  95

Gly Ser Phe Phe Tyr Ser Phe Gly Gly Gly Thr Glu Val Val Val Glu
            100                 105                 110


<210> SEQ ID NO 29
<211> LENGTH: 112
<212> TYPE: PRT
<213> ORGANISM: Artificial Sequence
<220> FEATURE:
<223> OTHER INFORMATION: 909 gL1 VL-region

<400> SEQUENCE: 29

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Gly Thr Tyr Ala
                85                  90                  95

Gly Ser Phe Phe Tyr Ser Phe Gly Gly Gly Thr Lys Val Glu Ile Lys
            100                 105                 110


<210> SEQ ID NO 30
<211> LENGTH: 219
<212> TYPE: PRT
<213> ORGANISM: Artificial Sequence
<220> FEATURE:
<223> OTHER INFORMATION: 909 gL1 VL + CL-region

<400> SEQUENCE: 30

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 31
<211> LENGTH: 112
<212> TYPE: PRT
<213> ORGANISM: Artificial Sequence
<220> FEATURE:
<223> OTHER INFORMATION: 909 gL10 VL-region

<400> SEQUENCE: 31

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110


<210> SEQ ID NO 32
<211> LENGTH: 219
<212> TYPE: PRT
<213> ORGANISM: Artificial Sequence
<220> FEATURE:
<223> OTHER INFORMATION: 909 gL10 VL + CL-region

<400> SEQUENCE: 32

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
```

```
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 33
<211> LENGTH: 112
<212> TYPE: PRT
<213> ORGANISM: Artificial Sequence
<220> FEATURE:
<223> OTHER INFORMATION: 909 gL54 VL-region

<400> SEQUENCE: 33

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Thr Tyr Ala
                85                  90                  95

Gly Ser Phe Phe Tyr Ser Phe Gly Gly Gly Thr Lys Val Glu Ile Lys
            100                 105                 110


<210> SEQ ID NO 34
<211> LENGTH: 219
<212> TYPE: PRT
<213> ORGANISM: Artificial Sequence
<220> FEATURE:
<223> OTHER INFORMATION: 909 gL54 VL + CL-region

<400> SEQUENCE: 34

Asp Val Val Met Thr Gln Ser Pro Ser Ser Leu Ser Ala Ser Val Gly
1               5                   10                  15
```

-continued

```
Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 35
<211> LENGTH: 112
<212> TYPE: PRT
<213> ORGANISM: Artificial Sequence
<220> FEATURE:
<223> OTHER INFORMATION: 909 gL55 VL-region

<400> SEQUENCE: 35

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Thr Tyr Gly Thr Tyr Ala
                85                  90                  95

Gly Ser Phe Phe Tyr Ser Phe Gly Gly Gly Thr Lys Val Glu Ile Lys
            100                 105                 110


<210> SEQ ID NO 36
<211> LENGTH: 219
<212> TYPE: PRT
<213> ORGANISM: Artificial Sequence
<220> FEATURE:
<223> OTHER INFORMATION: 909 gL55 VL + CL-region

<400> SEQUENCE: 36
```

Asp Val Val Met Thr Gln Ser Pro Ser Ser Leu Ser Ala Ser Val Gly
1 5 10 15

Asp Arg Val Thr Ile Thr Cys Gln Ala Ser Glu Asp Ile Ser Arg Tyr
20 25 30

Leu Val Trp Tyr Gln Gln Lys Pro Gly Lys Ala Pro Lys Arg Leu Ile
35 40 45

Tyr Lys Ala Ser Thr Leu Ala Ser Gly Val Pro Ser Arg Phe Lys Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Thr Tyr Gly Thr Tyr Ala
85 90 95

Gly Ser Phe Phe Tyr Ser Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 37
<211> LENGTH: 112
<212> TYPE: PRT
<213> ORGANISM: Artificial Sequence
<220> FEATURE:
<223> OTHER INFORMATION: 909 gL13 VL-region

<400> SEQUENCE: 37

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Ser Arg Tyr
20 25 30

Leu Val Trp Tyr Gln Gln Lys Pro Gly Lys Ala Pro Lys Arg Leu Ile
35 40 45

Tyr Lys Ala Ser Thr Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Ala Thr Tyr Gly Thr Tyr Ala
85 90 95

Gly Ser Phe Phe Tyr Ser Phe Gly Gly Gly Thr Lys Val Glu Ile Lys
100 105 110

<210> SEQ ID NO 38
<211> LENGTH: 219
<212> TYPE: PRT
<213> ORGANISM: Artificial Sequence

```
<220> FEATURE:
<223> OTHER INFORMATION: 909 gL13 VL + CL-region

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 39
<211> LENGTH: 112
<212> TYPE: PRT
<213> ORGANISM: Artificial Sequence
<220> FEATURE:
<223> OTHER INFORMATION: 909 gL50 VL-region

<400> SEQUENCE: 39

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Ala Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110
```

<210> SEQ ID NO 40
<211> LENGTH: 219
<212> TYPE: PRT
<213> ORGANISM: Artificial Sequence
<220> FEATURE:
<223> OTHER INFORMATION: 909 gL50 VL + CL-region

<400> SEQUENCE: 40

```
Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Ala Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 41
<211> LENGTH: 120
<212> TYPE: PRT
<213> ORGANISM: Artificial Sequence
<220> FEATURE:
<223> OTHER INFORMATION: Rabbit Ab 909 VH region

<400> SEQUENCE: 41

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Ile Tyr Pro Ser Gly Ser Thr Tyr Cys Ala Ser Trp Ala Lys Gly
    50                  55                  60

Arg Phe Thr Ile Ser Lys Ala Ser Thr Thr Val Asp Leu Lys Ile Thr
65                  70                  75                  80

Ser Pro Thr Thr Glu Asp Thr Ala Thr Tyr Phe Cys Ala Arg Pro Asp
                85                  90                  95
```

-continued

```
Asn Asp Gly Thr Ser Gly Tyr Leu Ser Gly Phe Gly Leu Trp Gly Gln
            100                 105                 110

Gly Thr Leu Val Thr Val Ser Ser
        115                 120


<210> SEQ ID NO 42
<211> LENGTH: 121
<212> TYPE: PRT
<213> ORGANISM: Artificial Sequence
<220> FEATURE:
<223> OTHER INFORMATION: 909gH1 VH region

<400> SEQUENCE: 42

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Phe Thr Ile Ser Lys Ala Ser Thr Thr Val Asp Leu Lys Leu
65                  70                  75                  80

Ser Ser Val Thr Ala Ala Asp Thr Ala Thr Tyr Phe Cys Ala Arg Pro
                85                  90                  95

Asp Asn Asp Gly Thr Ser Gly Tyr Leu Ser Gly Phe Gly Leu Trp Gly
            100                 105                 110

Gln Gly Thr Leu Val Thr Val Ser Ser
        115                 120


<210> SEQ ID NO 43
<211> LENGTH: 448
<212> TYPE: PRT
<213> ORGANISM: Artificial Sequence
<220> FEATURE:
<223> OTHER INFORMATION: 909gH1 IgG4 VH + human gamma-4P constant

<400> SEQUENCE: 43

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Phe Thr Ile Ser Lys Ala Ser Thr Thr Val Asp Leu Lys Leu
65                  70                  75                  80

Ser Ser Val Thr Ala Ala Asp Thr Ala Thr Tyr Phe Cys Ala Arg Pro
                85                  90                  95

Asp Asn Asp Gly Thr Ser Gly Tyr Leu Ser Gly Phe Gly Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His
195 200 205

Lys Pro Ser Asn Thr Lys Val Asp Lys Arg Val Glu Ser Lys Tyr Gly
210 215 220

Pro Pro Cys Pro Pro Cys Pro Ala Pro Glu Phe Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

Lys Thr Lys Pro Arg Glu Glu Gln Phe Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Gly Leu Pro Ser Ser Ile Glu Lys Thr
325 330 335

Ile Ser Lys Ala Lys Gly Gln Pro Arg Glu Pro Gln Val Tyr Thr Leu
340 345 350

Pro Pro Ser Gln Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Arg Leu Thr Val Asp Lys Ser
405 410 415

Arg Trp Gln Glu Gly Asn Val Phe Ser Cys Ser Val Met His Glu Ala
420 425 430

Leu His Asn His Tyr Thr Gln Lys Ser Leu Ser Leu Ser Leu Gly Lys
435 440 445

<210> SEQ ID NO 44
<211> LENGTH: 123
<212> TYPE: PRT
<213> ORGANISM: Artificial Sequence
<220> FEATURE:
<223> OTHER INFORMATION: 909gH14 VH region

<400> SEQUENCE: 44

Glu Val Gln Leu Gln Glu Ser Gly Pro Gly Leu Val Lys Pro Ser Gly
1 5 10 15

Thr Leu Ser Leu Thr Cys Ala Val Ser Gly Phe Ser Leu Ser Thr Tyr
20 25 30

Tyr Met Ser Trp Val Arg Gln Pro Pro Gly Lys Gly Leu Glu Trp Ile
35 40 45

Gly Ile Ile Tyr Pro Ser Gly Ser Thr Tyr Cys Ala Ser Trp Ala Lys
50 55 60

Gly Arg Phe Thr Ile Ser Lys Ala Ser Thr Lys Asn Thr Val Asp Leu
65 70 75 80

```
Lys Leu Ser Ser Val Thr Ala Ala Asp Thr Ala Thr Tyr Phe Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser
        115                 120


<210> SEQ ID NO 45
<211> LENGTH: 450
<212> TYPE: PRT
<213> ORGANISM: Artificial Sequence
<220> FEATURE:
<223> OTHER INFORMATION: 909gH14 IgG4 VH + human gamma-4P constant

<400> SEQUENCE: 45

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 46
<211> LENGTH: 123
<212> TYPE: PRT
<213> ORGANISM: Artificial Sequence
<220> FEATURE:
<223> OTHER INFORMATION: 909 gH15 VH region

<400> SEQUENCE: 46

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser
        115                 120


<210> SEQ ID NO 47
<211> LENGTH: 450
<212> TYPE: PRT
<213> ORGANISM: Artificial Sequence
<220> FEATURE:
<223> OTHER INFORMATION: 909gH15 IgG4 VH + human gamma-4P constant

<400> SEQUENCE: 47

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
```

-continued

```
        35                  40                  45

Gly Ile Ile Tyr Pro Ser Gly Ser Thr Tyr Ser Ala Ser Trp Ala Lys
    50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 48
<211> LENGTH: 123
<212> TYPE: PRT
<213> ORGANISM: Artificial Sequence
<220> FEATURE:
<223> OTHER INFORMATION: 909 gH61 VH region

<400> SEQUENCE: 48

```
Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser
        115                 120
```

<210> SEQ ID NO 49
<211> LENGTH: 450
<212> TYPE: PRT
<213> ORGANISM: Artificial Sequence
<220> FEATURE:
<223> OTHER INFORMATION: 909gH61 IgG4 VH + human gamma-4P constant

<400> SEQUENCE: 49

```
Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 50
<211> LENGTH: 123
<212> TYPE: PRT
<213> ORGANISM: Artificial Sequence
<220> FEATURE:
<223> OTHER INFORMATION: 909 gH62 VH region

<400> SEQUENCE: 50

```
Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
```

-continued

```
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser
        115                 120


<210> SEQ ID NO 51
<211> LENGTH: 107
<212> TYPE: PRT
<213> ORGANISM: Artificial Sequence
<220> FEATURE:
<223> OTHER INFORMATION: IGKV1-17 human germline acceptor framework

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105


<210> SEQ ID NO 52
<211> LENGTH: 113
<212> TYPE: PRT
<213> ORGANISM: Artificial Sequence
<220> FEATURE:
<223> OTHER INFORMATION: IGHV4-4 human germline acceptor framework

<400> SEQUENCE: 52

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

METHOD TO IDENTIFY COMPOUNDS USEFUL TO TREAT DYSREGULATED LIPOGENESIS, DIABETES, AND RELATED DISORDERS

RELATED APPLICATIONS

This application is a continuation of U.S. patent application Ser. No. 16/708,015, filed Dec. 9, 2019, which is a continuation application of International Application No. PCT/US18/36941, filed Jun. 11, 2018, which is related to and claims the benefit of provisional U.S. Application No. 62/517,611, filed Jun. 9, 2017. The entirety of each of these applications is hereby incorporated by reference for all purposes.

STATEMENT OF GOVERNMENTAL INTEREST

This invention was made with government support under DK064360 awarded by the National Institutes of Health. The government has certain rights in this invention.

FIELD OF THE INVENTION

The present invention provides a method to identify compounds useful in the inhibition of abnormal or dysregulated de novo hepatic lipogenesis (DNL) and hepatic selective insulin resistance with potential resulting non-alcoholic fatty liver disease (NAFLD) and type 2-diabetes, as well as antibodies useful in the treatment of these diseases. The invention is based on the discovery that the cannabinoid receptor type-1 (CB1) agonist 2-arachidonylglycerol (2-AG) has an obligate binding partner, adipocyte lipid binding protein (aP2), and that 2-AG carries out certain biological functions in a protein complex with aP2.

INCORPORATION BY REFERENCE

The contents of the text file named "15020-022WO1US2_sequence_ST25.1.txt" which was created Aug. 10, 2022, and is 55.7 KB in size, are hereby incorporated by reference in their entirety.

BACKGROUND OF THE INVENTION

Obesity, which is characterized by adipose tissue expansion, increases the risk of a cluster of diseases including type 2 diabetes (T2D), non-alcoholic fatty liver disease (NAFLD), and dyslipidemia, which in turn increase the mortality rate from cardiovascular diseases (CVD) (Prospective Studies Collaboration, (2009) The Lancet 373, 1083-1096; Shimomura et al., (2000) Molecular cell 6, 77-86). One of the mechanisms proposed to underlie the pathophysiology of these diseases is the concept of hepatic selective insulin resistance, wherein insulin's action to block glucose production is impaired but its signaling to stimulate de novo lipogenesis (DNL) remains intact (Shimomura et al., (2000) Molecular cell 6, 77-86; McGarry (1992) Science 258, 766-770). This allows simultaneous excess production of glucose and fatty acids in the liver, resulting in hyperglycemia and dyslipidemia.

Hepatic DNL is an essential process that enables the storage of excess energy substrates as neutral lipids, but when chronically engaged, this pathway can contribute to metabolic disease. This has been demonstrated by tracer studies, which show that NAFLD patients exhibit a significant increase in the contribution of hepatic DNL to hepatic triglyceride content and to VLDL production (Nielsen et al., (2004) Jour. Clin. Invest. 113, 1582-1588; Lambert et al., (2014) Gastroenterology 146, 726-735). In addition, multiple reports have shown that increased hepatic DNL causes production of large VLDL particles (Horton et al., (1999) Jour. Clin. Invest. 103, 1067-1076; Grefhorst et al., (2002) Journ. Of Biol. Chem. 277, 34182-34190; Melish et al., (1980) American Jour. of Physio. 239, E354-362; Fabbrini et al., (2010) Hepatology 51, 679-689). Importantly, secretion of large VLDL induced by hepatic DNL leads to a highly pro-atherogenic lipoprotein profile: increased small dense LDL and decreased large HDL (Tchernof et al., (1996) Diabetes Care 19, 629-637; Cali et al., (2007) Diabetes Care 30, 3093-3098; Choi et al., (2011) Trends in Endocrin. & Metab. TEM22, 353-363). This may underlie the epidemiological (Sarwar et al., (2007) Circ. 115, 450-458), interventional (Rubins et al., (1999) NEJM 341, 410-418; Keech et al., (2005) Lancet 366, 1849-1861), and genetic (Do et al., (2013) Nature Genetics 45, 1345-1352) evidence for the causal relationship between increased triglyceride rich lipoprotein (TRL) and CVD (Nordestgaard (2016) Circ. Res. 118, 547-563; Musunru et al., (2016) Circ. Res. 118, 579-585). Therefore, increased hepatic DNL is a central mechanism that links obesity with NAFLD, dyslipidemia, and CVD. However, the signals that couple adipose tissue expansion in obesity to hepatic DNL are not well understood.

It is an object of the present invention to identify compounds useful in the inhibition of abnormal or dysregulated de novo hepatic lipogenesis (DNL) and hepatic selective insulin resistance with potential resulting non-alcoholic fatty liver disease (NAFLD) and type 2-diabetes.

It is another object of the present invention to provide new methods and compounds that can be administered in an effective amount to a host in need thereof to treat abnormal or dysregulated de novo hepatic lipogenesis, hepatic selective insulin resistance, fatty liver disease and diabetes.

SUMMARY OF THE INVENTION

The present invention is based on the surprising discovery that the cannabinoid receptor type-1 (CB1) agonist 2-arachidonylglycerol (2-AG) has an obligate binding partner, adipocyte lipid binding protein (aP2), and that biological functions are mediated via this 2-AG/aP2 protein complex. This discovery of this critical signaling protein complex provides a new treatment pathway for modulating lipid disorders.

2-Arachidonylglycerol (2-AG)

Endocannabinoids (ECs), such as anandamide (AEA) and 2-arachidonylglycerol (2-AG), are known endogenous bioactive lipid mediators deriving from arachidonic acid, which are physiologically synthesized and released upon demand from the brain, peripheral organs, and adipose tissue. ECs elicit a broad range of effects via G protein-coupled CB1 and CB2 receptors (Pacher et al., (2006) Pharmacol. Rev. 58, 389-462), which populate both central nervous system and peripheral nervous system as well as non-nervous peripheral tissues. Activation of CB1 promotes food intake (Di Marzo et al., (2001) Nature 410, 822-825), increases lipogenesis in adipose tissue (Cota et al., (2003) J. Clin. Invest. 112, 423-431; Matias et al., J. Clin. Endocrinol. Metab. 91, 3171-3180) and liver (Osei-Hayman et al., (2005) J. Clin. Invest. 115, 1298-1305) and causes insulin resistance (Eckhardt et al., (2009) Diabetologia 52, 664-674; Liu et al., (2012) Gastroenterology 142, 1218-1228) and dyslipidemia (Ruby et al., (2008) Proc. Natl. Acad. Sci. USA 105, 14561-14566), which suggests that the endocannabinoid/

CB1 system (ECS) is involved in obesity and its metabolic complications. The ECS is overactive in obesity (Matias et al., (2006) J. Clin. Endocrin. Metab. 91, 3171-3180), and CB1 inverse agonists reduce body weight and improve metabolic abnormalities in obese subjects (Addy et al., (2008) Cell Metab. 7, 68-78; Despres et al., (2005) NEJM 353, 2121-2134). Such CB1 inverse agonists, however, have been associated with severe adverse neuropsychiatric effects, including significant increases in suicidal incidence and tendencies, which have halted their therapeutic development. More recently, attempts to avoid CNS-directed side effects through the use of antibodies which directly antagonize CB1 have been suggested (See WO 2017/058771 to Bird Rock Bio, Inc.).

Adipocyte Protein 2 (aP2)

Obesity is characterized by increased adipose tissue lipolysis, which results in the release of factors including lipids and adipokines that may contribute to increased hepatic DNL (Horowitz et al., (2000) Amer. J. of Physio, Endocrin. & Metab. 278, E1144-1152; Horowitz et al., (1999) Amer. J. Physio. 276, E278-284; Girousse et al., (2013) PLoS Biol. 11, e10011485; Diraison et al., (2003) Diab. & Metab. 29, 478-485). Recently, it was shown that the lipid binding protein aP2 (Fabp4) is secreted from mouse and human adipocytes in response to lipolysis stimuli (Cao et al., (2013) Cell Metab. 17, 768-778; Ertunc et al., (2015) J. of Lipid Res. 56, 423-434). Interestingly, mice with genetic deletion of aP2 and the related molecule mall (Fabp5) exhibit markedly reduced hepatic DNL (Maeda et al., (2005) Cell Metabolism 1, 107-119; Cao et al., (2006) Diabetes 55, 1915-1922), and antibody-mediated aP2 neutralization blunts the expression of lipogenic enzymes in the liver of obese mice (Burak et al., (2015) Sci. Trans. Med. 7, 319ra205).

2-AG/aP2 Protein Complex

As described for the first time herein, it has been surprisingly discovered that 2-arachidonylglycerol (2-AG) exhibits its agonistic activity on CB1 via a complex in which 2-AG is associated with circulating aP2. Surprisingly, circulating aP2 is an obligatory binding partner of 2-AG, which promotes de novo lipogenesis (DNL) by facilitating 2-AG agonism of CB1 in hepatocytes. Circulating aP2 potentiates 2-AG's action through the CB1 G-protein coupled receptor, both in cell culture models and in vivo, wherein binding of the 2-AG/aP2 complex to CB1 suppresses downstream 5' adenosine monophosphate-activated protein kinase (AMPK) phosphorylation and stimulates DNL. By targeting the upstream stimulator of CB1—the 2-AG/aP2 complex-and not CB1 directly, the risk of neuropsychological side-affects associated with direct CB1 targeting may be reduced.

Thus, compounds, compositions, and methods of identifying compounds are provided that neutralize the ability of the cannabinoid receptor type-1 (CB1) agonist 2-arachidonylglycerol (2-AG) in complex with its obligate binding partner adipocyte lipid binding protein (aP2) from agonizing CB1 signaling in peripheral tissues. Provided herein are antibodies, antibody fragments, and antigen binding agents that target the novel 2-AG/aP2 complex antigen. Further provided herein are methods of treating a disorder associated with dysregulated or abnormal hepatic de novo lipogenesis and/or hepatic selective insulin resistance by inhibiting cannabinoid receptor type-1 (CB1) agonist 2-arachidonylglycerol (2-AG) in complex with its obligate binding partner adipocyte lipid binding protein (aP2) from binding and agonizing CB1.

Accordingly, provided herein are methods of identifying compounds for their ability to neutralize 2-AG/aP2 agonism of CB 1, in both cell-free and cell-based assays, including in vivo assays, the use of such compounds on neutralizing 2-AG/aP2 agonism of CB1, and methods of treating disorders mediated by CB1 stimulation, for example, the dysregulation of DNL and hepatic selective insulin resistance by using compounds capable of neutralizing 2-AG/aP2 agonism of CB1. The utilization of these methods to identify compounds that are capable of inhibiting 2-AG/aP2 agonism of CB1 are further demonstrated herein as shown in the Examples This discovery also allows the skilled person to neutralize the activity of the 2-AG/aP2 protein complex via an antibody that binds to the complex. In one embodiment, the antibody selectively binds to the 2-AG/aP2 complex over aP2 alone. Such antibodies are useful in the treatment of diseases mediated by 2-AG/aP2 agonism of CB1.

In a first aspect, a method of identifying a compound capable of binding 2-arachidonylglycerol/adipocyte binding protein complex (2-AG/aP2) is provided comprising:

i. contacting the compound with 2-AG in complex with aP2 (2-AG/aP2); and,
ii. determining whether the compound binds to 2-AG/aP2.

In one embodiment, the method further comprises introducing the compound into an assay with aP2 and 2-AG, or 2-AG/aP2, and CB1, and, determining whether 2-AG/aP2 binds to CB1, wherein non-binding of 2-AG/aP2 to CB1 is indicative of a compound capable of neutralizing 2-AG/aP2 agonism of CB1. In one embodiment, the method further comprises introducing the compound into a cellular assay in the presence of aP2 and 2-AG, and/or 2-AG/aP2, wherein the cellular assay includes a population of cells expressing CB1, and measuring the biological activity of CB1. In one embodiment, the cell population expressing CB1 are hepatocytes. In one embodiment, the cell population expressing CB1 are human cells. In one embodiment, the cell population expressing CB 1 are human hepatocyte cells.

In a second aspect of the present invention, a method of identifying a compound capable of neutralizing 2-AG/aP2 agonism of CB1 is provided comprising:

i. contacting the compound with aP2 and 2-AG, and/or 2-AG in complex with aP2 (2-AG/aP2);
ii. determining whether the compound binds to aP2, 2-AG, or 2-AG/aP2;
iii. introducing the compound into an assay with aP2 and 2-AG, or 2-AG/aP2, and CB1, and,
iv. determining whether 2-AG/aP2 binds to CB1, wherein non-binding of 2-AG/aP2 to CB1 is indicative of a compound capable of neutralizing 2-AG/aP2 agonism of CB1. In one embodiment, the method further comprises introducing the compound into a cellular assay in the presence of aP2 and 2-AG, and/or 2-AG/aP2, wherein the cellular assay includes a population of cells expressing CB1, and measuring the biological activity of CB1. In one embodiment, the cell population expressing CB1 are hepatocytes. In one embodiment, the cell population expressing CB1 are human cells. In one embodiment, the cell population expressing CB1 are human hepatocyte cells.

In a third aspect of the present invention, provided herein is a method of identifying a compound capable of neutralizing 2-AG/aP2 agonism of CB1 comprising:

i. contacting aP2 and 2-AG, and/or 2-AG/aP2 with CB1 in the presence of a compound;
ii. contacting aP2 and 2-AG, and/or 2-AG/aP2 with CB1 in the absence of a compound; and, iii. comparing the amount of bound 2-AG/aP2 to CB1 in the presence of the compound with the amount of bound 2-AG/aP2 to CB1 in the absence of the compound;

wherein a reduced amount of 2-AG/aP2 binding to CB1 in the presence of the compound is indicative of a compound capable of neutralizing CB1 agonism.

The method for measuring or identifying binding of a compound to 2-AG/aP2 or 2-AG/aP2 binding to CB1 is not particularly limited to the described illustrative embodiments. Examples of methods that can be utilized to are described further herein and in the Examples provided below, and include 8-Anilinonaphthalene-1-sulfonic acid (ANS) binding assay (See Examples 9, 10, and 17; FIGS. 3*e* and 6*e*) and microscale thermophoresis (See Example 17 and FIG. 3*f*).

In a fourth aspect of the present invention, provided herein is a method of identifying a compound capable of neutralizing 2-AG/aP2 agonism of CB1 comprising:

i. introducing aP2 and 2-AG, and/or 2-AG/aP2 into a first cellular assay comprising cells expressing CB1;
ii. determining a biological activity of CB 1 in the cells in the first cellular assay;
iii. introducing aP2 and 2-AG, and/or 2-AG/aP2 into a second cellular assay comprising cells expressing CB1, wherein the aP2 and 2-AG and/or 2-AG/aP2 is introduced in the presence of the compound,
iv. determining a biological activity of CB 1 in the cells in the second cellular assay; and,
v. comparing the biological activity of CB1 in the first cellular assay with the biological activity of CB1 in the second cellular assay, wherein a reduction in CB1 biological activity in the second assay compared to the CB 1 biological activity in the first assay is indicative of a compound that neutralizes 2-AG/aP2 agonism of CB 1. In one embodiment, the cell population comprises hepatocytes. In one embodiment, the cell population comprises human cells. In one embodiment, the cell population comprises human hepatocytes.

In a fifth aspect of the present invention, provided herein is a method of identifying a compound capable of neutralizing 2-AG/aP2 agonism of CB 1 comprising:

i. introducing the compound into a first cellular assay in the presence of aP2 and 2-AG, and/or 2-AG/aP2 and a cell population comprising cells expressing CB1, wherein the compound is present at a fixed concentration, and wherein aP2 and 2-AG and/or 2-AG/aP2 are present at a non-saturated concentration;
ii. determining a biological activity of CB1 in the cell population in the first cellular assay;
iii. introducing the compound into a second cellular assay in the presence of aP2, 2-AG, and/or 2-AG/aP2 and a cell population comprising cells expressing CB1, wherein the compound is present at a fixed concentration, and wherein aP2 and 2-AG, and/or 2-AG/aP2 are present at a saturated concentration;
iv. determining a biological activity of CB 1 in the cell population in the second cellular assay; and,
v. comparing the biological activity of CB 1 in the first cellular assay with the biological activity of CB 1 in the second cellular assay, wherein a reduction in CB 1 biological activity in the first assay greater than a reduction in CB1 biological activity in the second assay is indicative of a compound that neutralizes 2-AG/aP2 agonism of CB 1. In one embodiment, the cell population comprises hepatocytes. In one embodiment, the cell population comprises human cells. In one embodiment, the cell population comprises human hepatocytes.

In a sixth aspect of the present invention, provided herein is a method of identifying a compound capable of neutralizing 2-AG/aP2 agonism of CB 1 comprising:

i. introducing the compound into a first cellular assay in the presence of aP2 and 2-AG, and/or 2-AG in complex with aP2 (2-AG/aP2) and a cell population comprising cells expressing CB1, wherein the compound is present at a fixed concentration, and wherein aP2 and 2-AG and/or 2-AG/aP2 are present at a first concentration;
ii. determining a biological activity of CB 1 in the cell population in the first cellular assay;
iii. introducing the compound into a series of additional cellular assays in the presence of aP2 and 2-AG, and/or 2-AG in complex with aP2 (2-AG/aP2) and a cell population comprising cells expressing CB1, wherein the series of additional cellular assays includes the compound present at a fixed concentration and aP2, 2-AG, and/or 2-AG/aP2 at serially increasing concentration compared to the first cellular assay;
iv. determining a biological activity of CB 1 in the cell population in the series of additional cellular assays; and,
v. comparing the CB1 biological activity in the first cellular assay with the CB1 biological activity in the series of additional cellular assays, wherein a reduction in CB1 biological activity in the first cellular assay greater than a reduction in CB1 biological activity in the series of additional cellular assays is indicative of a compound that neutralizes 2-AG/aP2 agonism of CB1. In one embodiment, the cell population comprises hepatocytes. In one embodiment, the cell population comprises human cells. In one embodiment, the cell population comprises human cells.

In a seventh aspect, provided herein is a method of identifying a compound capable of neutralizing 2-AG/aP2 agonism of CB 1, comprising:

i. contacting the compound with aP2; and,
ii. determining whether the compound binds to aP2 at amino acids Ser54, Phe57, Arg107, Arg127, and/or Tyr129, or a combination thereof;

wherein the binding of the compound to aP2 at amino acids Ser54, Phe57, Arg107, Arg127, and/or Tyr129, or a combination thereof, is indicative of a compound capable of neutralizing 2-AG/aP2 agonism of CB1. In one embodiment, the method further comprises introducing the compound into a cellular assay in the presence of aP2 and 2-AG, and/or 2-AG/aP2, wherein the cellular assay includes a population of cells expressing CB1, and measuring the biological activity of CB1. In one embodiment, the cell population expressing CB1 are hepatocytes. In one embodiment, the cell population expressing CB1 are human cells. In one embodiment, the cell population expressing CB1 are human hepatocyte cells.

In an eighth aspect of the present invention, provided herein is a method of neutralizing 2-AG/aP2 agonism of CB1 in a subject comprising administering to the subject a compound including but not limited to an antibody that neutralizes the ability of 2-AG/aP2 from binding to CB1. In one embodiment, the compound neutralizes the ability of 2-AG/aP2 from binding to CB1 by binding to aP2 at amino acids Ser54, Phe57, Arg107, Arg127, and/or Tyr129, or a combination thereof. In one embodiment, the compound neutralizes the ability of 2-AG/aP2 from binding to CB1 by binding to aP2 at amino acids Ser54, Arg107, Arg127, and/or Tyr129, or a combination thereof.

In a ninth aspect of the present invention, provided herein is a method of neutralizing 2-AG/aP2 agonism of CB1 in a subject comprising administering to the subject a compound including but not limited to an antibody that inhibits the ability of 2-AG/aP2 to form.

In a tenth aspect of the present invention, provided herein is a method of inhibiting hepatic de novo lipogenesis (DNL) in a subject comprising administering to the subject a compound including but not limited to an antibody that neutralizes the ability of a 2-AG/aP2 to agonize CB1, wherein the compound does not directly bind to CB1.

In an eleventh aspect of the present invention, provided herein is a method of inhibiting hepatic selective insulin resistance in a subject comprising administering to the subject a compound including but not limited to an antibody that neutralizes the ability of a 2-AG/aP2 to agonize CB1, wherein the compound does not directly bind to CB1.

In a twelfth aspect of the present invention, provided herein is a method of treating a subject with a disorder mediated by the dysregulation of de novo lipogenesis (DNL) comprising administering to the subject a compound including but not limited to an antibody that neutralizes the ability of a 2-AG/aP2 to agonize CB1, wherein the compound does not directly bind to CB1. When administered to a host in need thereof, using a compound that is capable of targeting the interaction of the 2-AG/aP2 with CB1 provides a decrease in the production of hepatic DNL and suppresses VLDL production, resulting in an improved lipid profile. In one embodiment, the disorder mediated by the dysregulation of DNL is selected from diabetes (both type 1 and type 2), hyperglycemia, diabetic ketoacidosis, hyperglycemic hyperosmolar syndrome, cardiovascular disease, diabetic nephropathy or kidney failure, diabetic retinopathy, impaired fasting glucose, impaired glucose tolerance, dyslipidemia, obesity, cataracts, stroke, atherosclerosis, impaired wound healing, perioperative hyperglycemia, hyperglycemia in the intensive care unit patient, insulin resistance syndrome, metabolic syndrome, fibrosis, including lung and liver fibrosis, and non-alcoholic fatty liver disease (NAFLD), including nonalcoholic steatohepatitis (NASH). In one embodiment, the disorder is selected from dyslipidemia, cardiovascular disease (CVD), atherosclerosis, type-II diabetes, and non-alcoholic fatty liver disease (NAFLD).

In a thirteenth aspect of the present invention, provided herein is a method of treating a subject with a disorder mediated by the hepatic selective insulin resistance comprising administering to the subject a compound including but not limited to an antibody that neutralizes the ability of a 2-AG/aP2 to agonize CB 1, wherein the compound does not directly bind to CB1. In one embodiment, the disorder is type-II diabetes.

In a fourteenth aspect of the present invention, provided herein is a method of reducing very low-density lipoprotein (VLDL) levels in a subject comprising administering to the subject a compound including but not limited to an antibody that neutralizes the ability of a 2-AG/aP2 to agonize CB1, wherein the compound does not directly bind to CB1.

In a fifteenth aspect of the present invention, provided herein is a method of modulating dyslipidemia in a subject comprising administering to the subject a compound including but not limited to an antibody that neutralizes the ability of a 2-AG/aP2 to agonize CB 1, wherein the compound does not directly bind to CB1.

In a sixteenth aspect of the present invention, provided herein is a method of treating fibrosis in a subject comprising administering to the subject a compound including but not limited to an antibody that neutralizes the ability of a 2-AG/aP2 to agonize CB 1, wherein the compound does not directly bind to CB1. In one embodiment, the fibrosis is liver fibrosis. In one embodiment, the fibrosis is lung fibrosis. In one embodiment, the fibrosis is idiopathic lung fibrosis.

In various embodiments, compounds capable of neutralizing 2-AG/aP2 agonism of CB1 acts by one or more of (i) neutralizing the effect of the 2-AG/aP2 complex on hepatocyte DNL; (ii) preventing or decreasing the stimulation of the CB1 receptor by 2-AG/aP2 in a manner that results in increased AMPK phosphorylation; (iii) preventing or decreasing 2-AG/aP2 from binding to the CB1 receptor and activating downstream signaling; (iv) preventing or decreasing aP2 from allosterically binding to the CB1 receptor and changing the receptor's three dimensional conformation such that 2-AG cannot bind the receptor; (v) modifying 2-AG/aP2 by inducing a conformational change that prevents 2-AG/aP2 from binding effectively to the CB1 receptor; (vi) suppressing VLDL production resulting in an improved lipid profile and reduced atherosclerotic plaque burden. Any one or a combination of above are referred to herein as "2-AG/aP2 mediated CB1 receptor activity disruption."

A compound capable of neutralizing 2-AG/aP2 agonism of CB1 can be any compound that prevents 2-AG/aP2 from binding to CB1 or disrupts the ability of 2-AG/aP2 to agonize CB1, resulting in a reduction in CB1 biological activity. CB1 biological activity generally refers to any observable effect resulting from the interaction between the CB1 and its agonistic binding partner 2-AG/aP2. The biological activity may be 2-AG/aP2 binding to CB1, detection of CB1-mediated intracellular signal transduction; or determination of an end-point physiological effect. Representative, but non-limiting, examples of CB1 biological activity upon agonistic stimulation by 2-AG/aP2 include, but are not limited to, signaling and regulation of the processes discussed herein, e.g., suppression of downstream AMPK phosphorylation, phosphorylation of mitogen-activated protein kinases (MAPK), such as p42/p44 MAPK, p38 MAPK and c-Jun N-terminal kinase, increased DNL production, increased VLDL production, and/or inhibition of cyclic AMP formation. In one embodiment, the compound is a small molecule, a ligand, an antibody, antigen binding agent, or antibody fragment that binds to aP2, 2-AG, and or 2-AG/aP2 and neutralizes the ability of 2-AG/aP2 to agonize CB1. Examples of assays to detect CB1 biological activity are further exemplified in the Example below, and include, assays relating to AMPK phosphorylation (see Example 7 and 15; FIGS. 1*d*, 1*g*, and 3j), VLDL production (See examples 4 and 18; FIGS. 4*a*, 4*d*, 4*g*, 7*b*, and 7*c*), and DNL production (See examples 4, 16, and 17; FIGS. 3*b*, 3*i*, 3*k*, 31, and 6*a*).

In one embodiment as described above, the compound is an antibody, antibody binding agent, or antibody fragment that binds aP2 and inhibits the interaction of aP2 with 2-AG. In one embodiment, the compound is an antibody, antibody binding agent, or antibody fragment that binds aP2 in complex with 2-AG and inhibits the interaction of the 2-AG/aP2 complex from binding to CB1. In one embodiment, the antibody, antibody binding agent, or antibody fragment binds aP2 and/or aP2 in complex with 2-AG loosely, for example with a Kd of greater than $10^{-7}$ M.

In some embodiments of any of the aspects described above, the antibody selectively binds to the 2-AG/aP2 complex over aP2 alone. In one embodiment, the antibody selectively binds to the 2-AG/aP2 complex with a Kd of $\leq 10^{-9}$ M. Methods for identifying preferably binding antibodies are generally known in the field. In one embodiment, provided herein is a method of identifying an antibody that selectively binds 2-AG/aP2 over aP2 generally comprising administering to a non-human animal, for example a rabbit, mouse, rat, or goat, a heterologous 2-AG/aP2 protein complex, for example human 2-AG/aP2, in order to raise antibodies against the heterologous 2-AG/aP2 in complex, isolating said antibodies, subjecting said antibodies to one or more binding assays measuring the binding affinity to 2-AG/aP2 and aP2 alone, for example a competitive binding assay, wherein antibodies that preferably bind 2-AG/aP2 over aP2 are isolated for use to neutralize 2-AG/aP2 agonism of CB1. In one embodiment, the preferably binding 2-AG/aP2 antibody comprises CDR regions directed to human 2-AG/aP2. In one embodiment, the preferably binding 2-AG/aP2 antibody is humanized according to known methods. Methods describing antibody production, including humanizing antibodies, include U.S. Pat. Nos. 7,223,392, 6,090,382, 5,859,205, 6,090,382, 6,054,297, 6,881,557, 6,284,471, and 7,070,775.

In one embodiment, the antibody or antibody binding agent contains a light chain or light chain fragment having a variable region, wherein said variable region comprises one, two, or three complementarity determining regions (CDRs) independently selected from Seq. ID No. 7, Seq. ID No. 8, and Seq. ID No. 9. In another embodiment, the antibody or antigen binding agent administered to a subject comprises a light chain or light chain fragment having a variable region, wherein said variable region comprises one, two, or three CDRs independently selected from Seq. ID No. 10, Seq. ID No. 11, Seq. ID No. 12, Seq. ID No. 13, Seq. ID No. 22, Seq. ID No. 23, or Seq. ID No. 24. In still another embodiment, the antibody or antibody binding agent administered comprises a light chain or light chain fragment having a variable region, wherein said variable region comprises one, two, or three CDRs independently selected from Seq. ID No. 7, Seq. ID No. 8 and Seq. ID No. 9, Seq. ID No. 10, Seq. ID No. 11, Seq. ID No. 12, Seq. ID No. 13, Seq. ID No. 22, Seq. ID No. 23, or Seq. ID No. 24. In one embodiment, the antibody or antibody binding agent administered to a subject comprises a light chain or light chain fragment having a variable region, wherein said variable region comprises Seq. ID No. 7, Seq. ID. No. 8, and at least one CDR selected from Seq. ID. No. 9, Seq. ID No. 10, Seq. ID No. 11, Seq. ID No. 12, Seq. ID No. 13, Seq. ID No. 22, Seq. ID No. 23, or Seq. ID No. 24. Alternatively, one or more of the disclosed and selected CDRs can be altered by substitution of one or more amino acids that do not adversely affect or that improve the properties of the antibody or antigen binding agent, as further described herein. In one embodiment, the selected CDR(s) is/are placed in a human immunoglobulin framework. In one embodiment, the human immunoglobulin framework is further modified or altered to maintain the binding affinity specificity of the grafted CDR region. In one embodiment, the antibody or antibody binding agent administered has a Kd for human aP2 of $\geq 10^{-7}$ M.

In one embodiment, the antibody or antibody binding agent administered to a subject includes at least one CDR selected from Seq. ID Nos. 7-13 or Seq. ID Nos. 22-24, and at least one CDR selected from CDRH1 (Seq. ID NO. 14), CDRH1 variant 1 (Seq. ID No. 15), CDRH1 variant 2 (Seq. ID No. 25), CDRH2 (Seq. ID No. 16), CDRH2 variant 1 (Seq. ID No. 17), CDRH2 variant 2 (Seq. ID No. 18), CDRH2 variant 3 (Seq. ID No. 26), CDHR3 (Seq. ID No. 19), CDHR3 variant 1 (Seq. ID No. 20), CDRH3 variant 2 (Seq. ID No. 21), or CDRH3 variant 3 (Seq. ID No. 27), wherein the CDR sequences are grafted into a human immunoglobulin framework. In one embodiment, the human immunoglobulin framework is further modified or altered to maintain the binding affinity specificity of the grafted CDR region.

In certain embodiments, the antibody or antigen binding agent administered includes at least the light chain variable sequence 909 gL1 (Seq. ID No. 29), the light chain sequence 909 gL1 VL+CL (Seq. ID No. 30), the light chain variable sequence 909 gL10 (Seq. ID No. 31), the light chain sequence 909 gL10 VL+CL (Seq. ID No. 32), the light chain variable sequence 909 gL13 (Seq. ID No. 37), the light chain sequence 909 gL13 VL+CL (Seq. ID No. 39), the light chain variable sequence 909 gL50 (Seq. ID No. 38), the light chain sequence 909 gL50 VL+CL (Seq. ID No. 40), the light chain variable sequence 909 gL54 (Seq. ID No. 33), the light chain sequence 909 gL54 VL+CL (Seq. ID No. 34), the light chain variable sequence 909 gL55 (Seq. ID No. 35) or the light chain sequence 909 gL55 VL+CL (Seq. ID No. 36).

In other embodiments, the antibody or antigen binding agent administered includes a light chain variable sequence selected from 909 gL1 (Seq. ID No. 29), 909 gL10 (Seq. ID No. 31), 909 gL13 (Seq. ID No. 37), 909 gL50 (Seq. ID No. 38), 909 gL54 (Seq. ID No. 33), or 909 gL55 (Seq. ID No. 35), and a heavy chain variable sequence selected from 909 gH1 (Seq. ID No. 42), 909 gH14 (Seq. ID No. 44), 909 gH15 (Seq. ID No. 46), 909 gH61 (Seq. ID No. 48), or 909 gH62(Seq. ID No. 50). For example, the antibody or antigen binding agent can include at least the light chain variable sequence 909 gL1 (Seq. ID No. 29) and the heavy chain variable sequence 909 gH1 (Seq. ID. No. 42).

In one embodiment, the antibody or antigen binding agent administered comprises a light chain variable sequence Rabbit Ab 909 VL region (Seq. ID No. 28), and further optionally comprises a heavy chain variable sequence Rabbit Ab 909 VH region (Seq. ID No. 41).

Other features and advantages of the invention will be apparent from the following detailed description and claims.

Other features and advantages of the invention will be apparent from the following detailed description and claims.

BRIEF DESCRIPTION OF THE FIGURES

FIG. 41 shows the atherosclerotic lesion area of en face aortas from $ApoE^{-/-}$ mice fed western diet and treated with PBS, CA33, or CA15 for 12 weeks. n=12, 11, and 12 for PBS, CA33, or CA15, respectively. Error bars are standard error of the mean.

DETAILED DESCRIPTION OF THE INVENTION

Figure 1A:
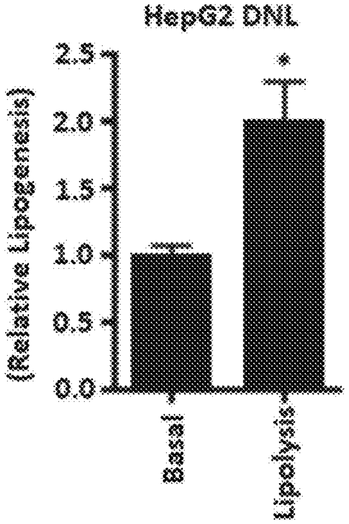
FIG. 1A is a bar graph that shows DNL in HepG2 cells treated with conditioned media from adipose tissue explant before (Basal) and after (Lipolysis) 1 μM IBMX stimulation. DNL was measured by scintillation count, normalized to protein concentration and expressed relative to the basal condition. n=4 in each condition. Error bars are standard error of the mean. The x-axis is the treatment group, and the y-axis is relative lipogenesis.

CB1 receptor signaling has been shown to be directly involved in de novo lipogenesis (DNL), and exhibits detrimental activity in, for example, obesity, diabetes, fibrosis, liver diseases, cardiovascular disease, and cancer (Kunos et al., (2009), Trends Pharmacol Sci 30:1-7). As described herein, it has been discovered that upon lipolysis stimulation, adipocytes secrete a signal—aP2—that directly induces DNL in hepatocytes by facilitating 2AG agonism of CB1 on hepatocytes. It has further been discovered that this mechanism can be therapeutically targeted utilizing compounds that interfere with the ability of 2-AG/aP2 to stimulate CB1. General Definitions Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, and protein and nucleic acid chemistry and hybridization described herein are those well-known and commonly used in the art.

The methods and techniques of the present invention are generally performed according to conventional methods well known in the art and as described in various general and more specific references that are cited and discussed throughout the present specification unless otherwise indicated. Enzymatic reactions and purification techniques may be performed according to manufacturer's specifications, as commonly accomplished in the art or as described herein. The nomenclatures used in connection with, and the laboratory procedures and techniques of, analytical chemistry, synthetic organic chemistry, and medicinal, and pharmaceutical chemistry described herein are those well-known and commonly used in the art. Standard techniques are used for chemical syntheses, chemical analyses, pharmaceutical preparation, formulation, and delivery, and treatment of patients.

That the present invention may be more readily understood, selected terms are defined below.

The term "host," "subject," or "patient" as used herein, typically refers to a human subject. Other hosts may include other mammals or vertebrate species. The term "host, "subject," or "patient" therefore, can alternatively refer to animals such as mice, monkeys, dogs, pigs, rabbits, domesticated swine (pigs and hogs), ruminants, equine, poultry, felines, murines, bovines, canines, and the like.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments, and polypeptide analogs of a protein sequence. A polypeptide may be monomeric or polymeric.

The term "human aP2 protein" or "human FABP4/aP2 protein", as used herein refers to the protein encoded by Seq. ID. No. 1, and natural variants thereof, as described by Baxa, C. A., Sha, R. S., Buelt, M. K., Smith, A. J., Matarese, V., Chinander, L. L., Boundy, K. L., Bernlohr, A. Human adipocyte lipid-binding protein: purification of the protein and cloning of its complementary DNA. Biochemistry 28: 8683-8690, 1989.

The term "mouse aP2 protein" or "mouse FAB4P/aP2 protein", as used herein, refers to the protein encoded by Seq. ID. No. 2, and natural variants thereof. The mouse protein is registered in Swiss-Prot under the number P04117.

"Antigen binding agents" as used herein include single chain antibodies (i.e. a full length heavy chain and light chain); Fab, modified Fab, Fab', modified Fab', F(ab')2, Fv, Fab-Fv, Fab-dsFv, single domain antibodies (e.g. VH or VL or VHH) for example as described in WO 2001090190, scFv, bi, tri or tetra-valent antibodies, Bis-scFv, diabodies, tribodies, triabodies, tetrabodies and epitope-antigen binding agents of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilized versions thereof, the Fab-dsFv was first disclosed in WO2010/035012. Other antibody fragments for use in the present invention include the Fab and Fab' fragments described in International patent applications WO2005/003169, WO2005/003170, and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

A typical Fab' molecule comprises a heavy and a light chain pair in which the heavy chain comprises a variable region VH, a constant domain CH1 and a natural or modified hinge region and the light chain comprises a variable region VL and a constant domain CL.

A dimer of a Fab' to create a F(ab')2 for example dimerization may be through a natural hinge sequence described herein, or derivative thereof, or a synthetic hinge sequence.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains at least some portion of the epitope binding features of an Ig molecule allowing it to specifically bind to aP2 and/or the 2-AG/aP2 complex. Such mutant, variant, or derivative antibody formats are known in the art and described below. Nonlimiting embodiments of which are discussed below. An antibody is said to be "capable of binding" a molecule if it is capable of specifically reacting with the molecule to thereby bind the molecule to the antibody.

A "monoclonal antibody" as used herein is intended to refer to a preparation of antibody molecules, which share a common heavy chain and common light chain amino acid sequence, or any functional fragment, mutant, variant, or derivation thereof which retains at least the light chain epitope binding features of an Ig molecule, in contrast with "polyclonal" antibody preparations that contain a mixture of different antibodies. Monoclonal antibodies can be generated by several known technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

In a full-length antibody, each heavy chain is comprised of a heavy chain variable region (abbreviated herein as HCVR or VH) and a heavy chain constant region (CH). The heavy chain constant region is comprised of four domains-either CH1, Hinge, CH2, and CH3 (heavy chains $\gamma$, $\alpha$ and $\delta$), or CH1, CH2, CH3, and CH4 (heavy chains $\mu$ and $\varepsilon$). Each light chain is comprised of a light chain variable region (abbreviated herein as LCVR or VL) and a light chain constant region (CL). The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antibody construct" as used herein refers to a polypeptide comprising one or more of the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci.

USA 90:6444-6448; Poljak, R. J., et al. (1994) Structure 2:1121-1123). An immunoglobulin constant domain refers to a heavy or light chain constant domain, for example a human IgA, IgD, IgE, IgG or IgM constant domains. Heavy chain and light chain constant domain amino acid sequences are known in the art.

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs (e.g., CDR3) has been replaced with murine CDR sequences.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31-35 (CDR-H1), residues 50-65 (CDR-H2) and residues 95-102 (CDR-H3) according to the Kabat numbering system. However, according to Chothia (Chothia et al., (1987) J. Mol. Biol., 196, 901-917 (1987)), the loop equivalent to CDR-H1 extends from residue 26 to residue 32. Thus, unless indicated otherwise "CDR-H1" as employed herein is intended to refer to residues 26 to 35, as described by a combination of the Kabat numbering system and Chothia's topological loop definition. For the light chain variable region, the hypervariable region ranges from amino acid positions 24 to 34 for CDRL1, amino acid positions 50 to 56 for CDRL2, and amino acid positions 89 to 97 for CDRL3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDRH1, CDRH2 and CDRH3 for the heavy chain CDRs, and CDRL1, CDRL2, and CDRL3 for the light chain CDRs. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia, or a mixture thereof, defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In an embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. See, e.g., Shapiro et al., Crit. Rev. Immunol. 22(3): 183-200 (2002); Marchalonis et al., Adv Exp Med Biol. 484:13-30 (2001). One of the advantages provided by various embodiments of the present invention takes advantage of the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following:

a residue that is adjacent to a CDR, a potential glycosylation site (can be either N- or 0-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" generally refers to antibodies which comprise heavy and light chain variable region sequences from a non-human species (e.g., a rabbit, mouse, etc.) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Another type of humanized antibody is a CDR-grafted antibody, in which at least one non-human CDR is inserted into a human framework. The latter is typically the focus of the present invention.

In particular, the term "humanized antibody" as used herein, is an antibody or a variant, derivative, analog or fragment thereof which immuno-specifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 50, 55, 60, 65, 70, 75 or 80%, preferably at least 85%, at least 90%, at least 95%, at least 98% or at least 99% identical to the amino acid sequence of a non-human antibody CDR. In one embodiment, the humanized antibody has a CDR region having one or more (for example 1, 2, 3 or 4) amino acid substitutions, additions and/or deletions in comparison to the non-human antibody CDR. Further, the non-human CDR can be engineered to be more "human-like" or compatible with the human body, using known techniques. A humanized antibody comprises substantially all of at least one, and typically two, variable domains (Fab, Fab', F(ab')2, F(ab')c, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, and CH3, or CH1, CH2, CH3, and CH4 of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgY, IgM, IgG, IgD, IgA and IgE, and any isotype, including without limitation IgA1, IgA2, IgG1, IgG2, IgG3 and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond exactly to either the donor antibody or the consensus framework. In a preferred embodiment, such mutations, however, will not be extensive. Usually, at least 50, 55, 60, 65, 70, 75 or 80%, preferably at least 85%, more preferably at least 90%, and most preferably at least 95%, 98% or 99% of the humanized antibody residues will correspond to those of the parental FR and CDR sequences. In one embodiment, one or more (for example 1, 2, 3 or 4) amino acid substitutions, additions and/or deletions may be present in the humanized antibody compared to the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

As used herein, the term "neutralizing" refers to neutralization of biological activity of 2-AG/aP2 complex agonism of CB1 when a compound, for example but not limited to an antibody, interferes with 2-AG/aP2 complex formation and/or 2-AG/aP2 binding to CB1 which induces CB1 stimulation. Neutralizing may be the result of different ways of interfering with 2-AG/aP2 complex stimulation of CB1. In one embodiment, the compound is an antibody, antibody fragment, or binding agent. A neutralizing antibody is an antibody where binding to aP2, 2-AG, and/or 2-AG/aP2 complex results in neutralization of a biological activity of aP2, 2-AG, and/or 2-AG/aP2 complex on CB1 agonism. Preferably the neutralizing binding protein binds aP2, 2-AG, and/or 2-AG/aP2 protein complex and decreases a biologically activity of aP2, 2-AG, and/or 2-AG/aP2 protein complex by at least about 5%, 10%, 15%, 20%, 25%, 30%, 35%, 40%, 50%, 60%, 80%, 85%, or more. Neutralization of a biological activity of aP2, 2-AG, and/or 2-AG/aP2 complex can be assessed by measuring one or more indicators of aP2, 2-AG, and/or 2-AG/aP2 complex agonism on CB1 as described herein. "Neutralizing" does not imply complete inactivation. Rather, the modulation is generally inhibition i.e. a reduction or diminution in the relevant biological activity by comparison with the activity seen in the absence of the agent.

A "neutralizing monoclonal antibody" as used herein is intended to refer to a preparation of antibody molecules, which upon binding to aP2, 2-AG, and/or 2-AG/aP2 complex are able to inhibit or reduce the biological activity of the 2-AG/aP2 complex activity, that is the ability of the 2-AG/aP2 complex to agonize the CB1 receptor, either partially or fully.

As used herein, the term "attenuation," "attenuate," and the like refers to the lessening or reduction in the severity of a symptom or condition caused by elevated blood glucose levels.

The term "epitope" or "antigenic determinant" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "Kd", as used herein, is intended to refer to the Affinity (or Affinity constant), which is a measure of the rate of binding (association and dissociation) between the antibody and antigen, determining the intrinsic binding strength of the antibody binding reaction.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and pPoteins, a Practical Approach, 2nd ea., pp. 20 1-16, Oxford University Press, New York, N.Y., (1999)."

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g. prophylactic or therapeutic agent).

2-Arachidonoylglycerol (2-AG)

2-Arachidonoylglycerol (2-AG), an endocannabinoid, is an endogenous agonist of the CB1 receptor. It is an ester formed from the omega-6 fatty acid arachidonic acid and glycerol, and has the chemical structure:

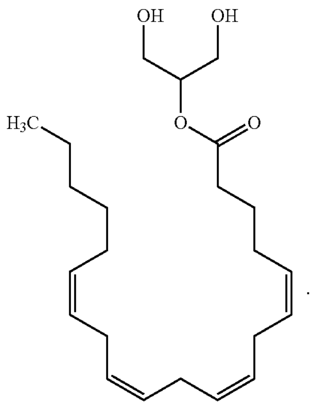 [SMILES: CCCCC/C=C\C/C=C\C/C=C\C/C=C\CCCC(=O)OC(CO)CO]

2-AG is synthesized from arachidonic acid-containing diacylglycerol (DAG). 2-AG is an endogenous lipid that exerts its metabolic effect through ligand activity against cannabinoid receptors. As described herein, 2-AG binds to CB1 in complex with aP2 to agonize CB1, which includes the stimulation of de novo lipogenesis (DNL).

Adipocyte Protein 2 (aP2)

Human adipocyte lipid binding protein (aP2), also known as fatty-acid binding protein 4 (FABP4), belongs to a family of intra-cellular lipid-binding proteins involved in the transport and storage of lipids (Banzszak et al., (1994) Adv. Protein Chem. 45, 89-151). The aP2 protein is involved in lipolysis and lipogenesis and has been indicated in diseases of lipid and energy metabolism such as diabetes, atherosclerosis, and metabolic syndromes. aP2 has also been indicated in the integration of metabolic and inflammatory response systems. (Ozcan et al., (2006) Science 313(5790):1137-40; Makowski et al., (2005) J Biol Chem. 280 (13):12888-95; and Erbay et al., (2009) Nat Med. 15(12):1383-91). More recently, aP2 has been shown to be differentially expressed in certain soft tissue tumors such as certain liposarcomas (Kashima et al., (2013) Virchows Arch. 462, 465-472).

aP2 is highly expressed in adipocytes and regulated by peroxisome-proliferator-activated receptor-gamma (PPAR-gamma) agonists, insulin, and fatty acids (Hertzel et al., (2000) Trends Endocrinol. Metab. 11, 175-180; Hunt et al., (1986) PNAS USA 83, 3786-3790; Melki et al., (1993) J. Lipid Res. 34, 1527-1534; Distel et al., (1992) J. Biol. Chem. 267, 5937-5941). Studies in aP2 deficient mice (FABP $4^{-/-}$) indicate protection against the development of insulin resistance associated with genetic or diet-induced obesity and improved lipid profile in adipose tissue with increased levels of C16:1n7-palmitoleate, reduced hepatosteatosis, and improved control of hepatic glucose production and peripheral glucose disposal (Hotamisligil et al., (1996) Science 274, 1377-1379; Uysal et al., (2000) Endocrinol. 141, 3388-3396; Cao et al., (2008) Cell 134, 933-944).

In addition, genetic deficiency or pharmacological blockade of aP2 reduces both early and advanced atherosclerotic lesions in an apolipoprotein E-deficient (ApoE $^{-/-}$) mouse model (Furuhashi et al., (2007) Nature, June 21; 447 (7147): 959-65; Makowski et al., (2001) Nature Med. 7, 699-705; Layne et al., (2001) FASEB 15, 2733-2735; Boord et al., (2002) Arteriosclerosis, Thrombosis, and Vas. Bio. 22, 1686-1691). Furthermore, aP2-deficiency leads to a marked protection against early and advanced atherosclerosis in apolipoprotein E-deficient ($ApoE^{-/-}$) mice (Makowski et al., (2001) Nature Med. 7, 699-705; Fu et al., (2000) J. Lipid Res. 41, 2017-2023). Hence, aP2 plays a critical role in many aspects of development of metabolic disease in preclinical models.

In the past two decades, the biological functions of FABPs in general and aP2 in particular have primarily been attributed to their action as intracellular proteins. Since the abundance of aP2 protein in the adipocytes is extremely high, accounting for up to a few percent of the total cellular protein (Cao et al., (2013) Cell Metab. 17 (5):768-78), therapeutically targeting aP2 with traditional approaches has been challenging, and the promising success obtained in preclinical models (Furuhashi et al., (2007) Nature 447, 959-965; Won et al., (2014) Nature Mat. 13, 1157-1164; Cai et al., (2013) Acta Pharm. *Sinica* 34, 1397-1402; Hoo et al., (2013) J. of Hepat. 58, 358-364) has been slow to progress toward clinical translation.

In addition to its presence in the cytoplasm, it has recently been shown that aP2 is actively secreted from adipose tissue through a non-classical regulated pathway (Cao et al., (2013) Cell Metab. 17(5), 768-778; Ertunc et al., (2015) J. Lipid Res. 56, 423-424). The secreted form of aP2 acts as a novel adipokine and regulates hepatic glucose production and systemic glucose homeostasis in mice in response to fasting and fasting-related signals. Serum aP2 levels are significantly elevated in obese mice, and blocking circulating aP2 improves glucose homeostasis in mice with diet-induced obesity (Cao et al., (2013) Cell Metab. 17(5):768-78). WO 2010/102171, titled Secreted aP2 and Methods of Inhibiting Same, to President and Fellows of Harvard University and WO 2016/176656, titled Anti-aP2 Antibodies and Antigen Binding Agents to Treat Metabolic Disorders, to President and Fellows of Harvard University and UCB Biopharma SPRL, describe the use of antibodies targeting circulating aP2 in order to modulate metabolic disorders.

Fatty acid-binding proteins (FABPs) are members of the superfamily of lipid-binding proteins (LBP). Nine different FABPs have to date been identified, each showing relative tissue enrichment: L (liver), I (intestinal), H (muscle and heart), A (adipocyte), E (epidermal), Il (ileal), B (brain), M (myelin) and T (testis). The primary role of all the FABP family members is regulation of fatty acid uptake and intracellular transport. The structures of all FABPs are similar—the basic motif characterizing these proteins is B-barrel, and a fatty acid ligand or ligands (e.g. a fatty acid, cholesterol, or retinoid) bound in its internal water-filled cavity.

The human aP2 protein is a 14.7 kDa intracellular and extracellular (secreted) lipid binding protein that consists of 132 amino acids comprising the amino acid sequence (Seq. ID No. 1) of Table 1. The cDNA sequence of human aP2 was previously described in Baxa, C. A., Sha, R. S., Buelt, M. K., Smith, A. J., Matarese, V., Chinander, L. L., Boundy, K. L., Bernlohr, A. Human adipocyte lipid-binding protein: purification of the protein and cloning of its complementary DNA. Biochemistry 28: 8683-8690, 1989, and is provided in Seq. ID No. 5. The human protein is registered in Swiss-Prot under the number P15090.

The mouse aP2 protein sequence comprises the amino acid sequence of Seq. ID No. 2 of Table 1. The cDNA sequence of mouse aP2 is provided in Seq. ID No. 6. The mouse protein is registered in Swiss-Prot under the number P04117.

Both the human and mouse aP2 protein include at least two major conserved domains: an 11-amino acid nuclear localization signal (aa22-32: kevgvgfatrk (Seq. ID No. 3)); and a 3-amino acid fatty acid binding region (aa127-129: rvy (Seq. ID No. 4)).

TABLE 1 aP2 Protein and cDNA Sequences

| Protein or cDNA | Seq. ID No. | Sequence |
|---|---|---|
| Fatty acid-binding protein, adipocyte (FABP4/aP2)[*H. sapiens*] | 1 | MCDAFVGTWKLVSSENFDDYMKEVGVGFATRKV AGMAKPNMIISVNGDVITIKSESTFKNTEISFILGQE FDEVTADDRKVKSTITLDGGVLVHVQKWDGKSTT IKRKREDDKLVVECVMKGVTSTRVYERA |
| Fatty acid-binding protein, adipocyte (FABP4/aP2 [*M. musculus*]) | 2 | MCDAFVGTWKLVSSENFDDYMKEVGVGFATRKV AGMAKPNMIISVNGDLVTIRSESTFKNTEISFKLGV EFDEITADDRKVKSIITLDGGALVQVQKWDGKSTTI KRKRDGDKLVVECVMKGVTSTRVYERA |

TABLE 1-continued aP2 Protein and cDNA Sequences

| Protein or cDNA | Seq. ID No. | Sequence |
|---|---|---|
| aP2 nuclear localization amino acid sequence | 3 | KEVGVGFATRK |
| aP2 fatty acid binding domain amino acid sequence | | RVY |
| Fatty acid-binding protein, adipocyte (FABP4/aP2)[*H. sapiens*] cDNA | 5 | ATGTGTGATGCTTTTGTAGGTACCTGGAAACTTG<br>TCTCCAGTGAAAACTTTGATGATTATATGAAAGA<br>AGTAGGAGTGGGCTTTGCCACCAGGAAAGTGGC<br>TGGCATGGCCAAACCTAACATGATCATCAGTGTG<br>AATGGGGATGTGATCACCATTAAATCTGAAAGT<br>ACCTTTAAAAATACTGAGATTTCCTTCATACTGG<br>GCCAGGAATTTGACGAAGTCACTGCAGATGACA<br>GGAAAGTCAAGAGCACCATAACCTTAGATGGGG<br>GTGTCCTGGTACATGTGCAGAAATGGGATGG<br>AAAATCAACCACCATAAAGAGAAAACGAGAGG<br>ATGATAAACTGGTGGTGGAATGCGTCATGAAAG<br>GCGTCACTTCCACGAGAGTTTATGAGAGAGCAT<br>AA |
| Fatty acid-binding protein, adipocyte (FABP4/aP2 [*M. musculus*]) cDNA | 6 | ATGTGTGATGCCTTTGTGGGAACCTGGAAGCTTG<br>TCTCCAGTGAAAACTTCGATGATTACATGAAAGA<br>AGTGGGAGTGGGCTTTGCCACAAGGAAAGTGGC<br>AGGCATGGCCAAGCCCAACATGATCATCAGCGT<br>AAATGGGGATTTGGTCACCATCCGGTCAGAGAG<br>TACTTTTAAAAACACCGAGATTTCCTTCAAACTG<br>GGCGTGGAATTCGATGAAATCACCGCAGACGAC<br>AGGAAGGTGAAGAGCATCATAACCCTAGATGGC<br>GGGGCCCTGGTGCAGGTGCAGAAGTGGGATGGA<br>AAGTCGACCACAATAAAGAGAAAACGAGATGGT<br>GACAAGCTGGTGGTGGAATGTGTTATGAAAGGC<br>GTGACTTCCACAAGAGTTTATGAAAGGGCATGA |

CB1 Receptor

The human cannabinoid receptor type 1 (CB1) (Uniprot P21554) is a 472-amino acid, seven-transmembrane helix, G protein-coupled cannabinoid receptor located primarily in the central and peripheral nervous system, as well as peripheral tissues such as the liver. In the liver, activation of the CB1 receptor is known to increase de novo lipogenesis. The biological effects of CB1 receptor stimulation by 2-AG/aP2 include the suppression or de-phosphorylation of AMPK and the induction of de novo lipogenesis.

Methods of Identifying Compounds That Neutralize 2-AG/aP2 Agonism of CM

One aspect of the present invention relates to a method for identifying compounds which modulate/affect, and preferably neutralize, the agonistic activity of 2-AG/aP2 on CB1 for use in a therapy described herein. In one embodiment, the compounds interact with 2-AG, aP2, and/or 2-AG/aP2, without directly antagonizing CB1. Compounds of the present invention may include, by way of non-limiting example, peptides produced by expression of an appropriate nucleic acid sequence in a host cell or using synthetic organic chemistries (e.g., antibodies, antibody fragments, or antigen binding agents), or non-peptide small molecules produced using conventional synthetic organic chemistries well known in the art. Identifying assays may be automated in order to facilitate the identification of a large number of small molecules at the same time.

Methods used for identifying compounds may be cell-based or cell-free. In one embodiment, the screen is cell free, and compounds are screened to determine their ability to interact or bind to aP2, 2-AG, and or 2-AG/aP2. For example, a compound is contacted with aP2, 2-AG, and/or 2-AG/aP2 and then an assay is performed to detect binding of the compound to aP2, 2-AG, and or 2-AG/aP2. In further embodiments, the compound can be contacted with aP2, 2-AG, and/or 2-AG/aP2 in the presence of CB1, and the binding of said 2-AG/aP2 to CB1 can be measured and compared to the binding of said 2-AG/aP2 outside of the presence of the compound.

Assays to detect binding of compounds are well known in the art, for example as described in McFedries, et al, Methods for the Elucidation of Protein-Small Molecule Interactions. Chemistry & Biology (2013); Vol. 20(5):667-673; Pollard, A Guide to Simple and Informative Binding Assays, Mol. Biol. Cell (2010) Vol. 21, 4061— 4067, both incorporated herein by reference in their entirety.

Figure 3A:
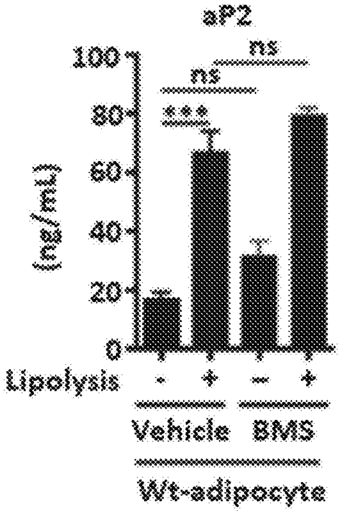
FIG. 3A is a bar graph that shows aP2 levels in the conditioned media from vehicle or 5 μM BMS-309403 pretreated 3T3L1 adipocytes before and after 1 mM IBMX stimulation. n=3 for each condition. Error bars are standard error of the mean. The x-axis is the treatment group, and the y-axis is aP2 level measured in nanograms per milliliter.
Figure 3B:
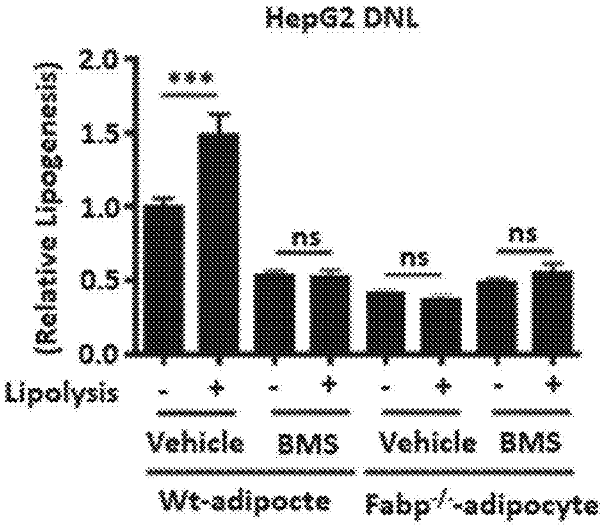
FIG. 3B is a bar graph that shows DNL levels for 3T3L1 adipocytes or Fabp4/5 double knockout (Fabp$^{-/-}$) adipocytes pretreated with vehicle or 5 μM BMS-309403 for 48 hrs and then stimulated with or without 1 μM IBMX. Conditioned media was used to treat HepG2 cells, and DNL was analyzed by scintillation count, normalized to protein concentration and expressed relative to the basal condition. n=4 in each condition. Error bars are standard error of the mean. The x-axis is the treatment group, and the y-axis is relative lipogenesis.
Figure 3C:
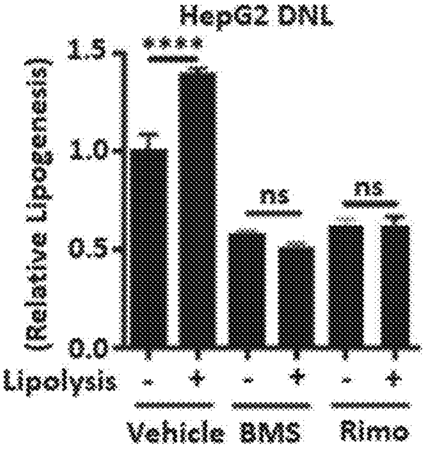
FIG. 3C is a bar graph that shows the effect of 1 μM Rimonabant on DNL in HepG2 cells treated with conditioned media from 3T3L1 adipocytes before and after 1 μM IBMX stimulation. DNL in HepG2 cells treated with conditioned media from 3T3L1 adipocytes pretreated with 5 μM BMS-309403 for 48 hrs was also analyzed in parallel. DNL was measured by scintillation count, normalized to protein concentration and expressed relative to the basal condition. n=4 in each condition. Error bars are standard error of the mean. The x-axis is the treatment group, and the y-axis is relative lipogenesis.
Figure 6A:
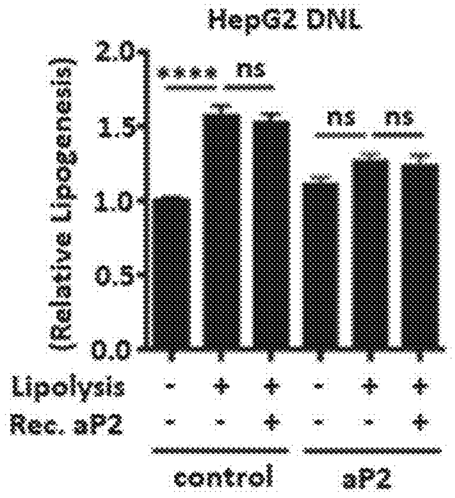
FIG. 6A is a bar graph that shows DNL analyzed by scintillation count, normalized to protein concentration and expressed relative to the basal condition. n=4 in each condition. Error bars are standard error of the mean. The x-axis is treatment group, and the y-axis is relative lipogenesis.
Figure 6B:
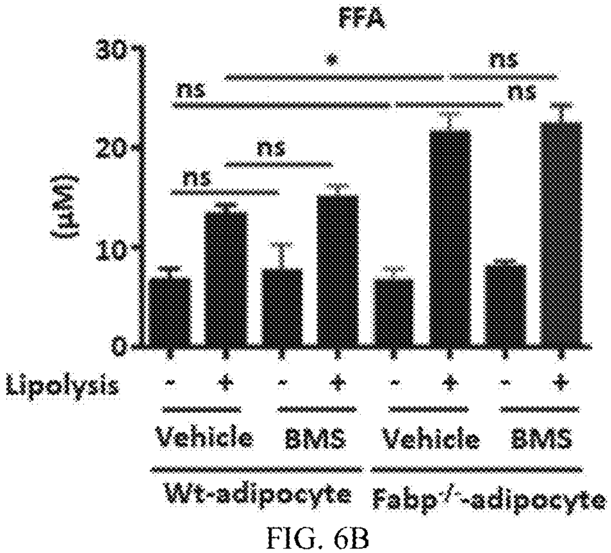
FIG. 6B is a bar graph that shows FFA release from 3T3L1 adipocytes and $Fabp^{-/-}$ adipocytes treated with or without BMS-309403. n=3 in each condition. Error bars are standard error of the mean. The x-axis is the treatment group, and the y-axis is micromolar FFA level.
Figure 6C:
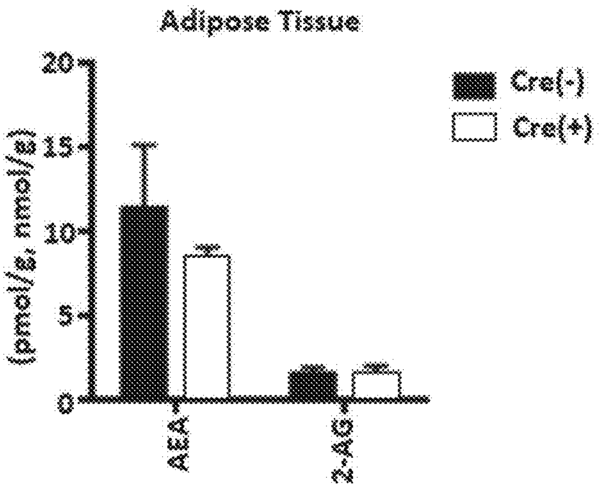
FIG. 6C is a bar graph that shows endocannabinoid level in adipose tissue of $FABP4^{f/f}$ and $FABP4^{adip-/-}$ mice fed HFD. n=8 and 6 for $FABP4^{f/f}$ and FABP $4^{adip-/-}$ mice, respectively. Error bars are standard error of the mean. The x-axis is endocannabinoid type, and the y-axis is endocannabinoid level measured in picomoles or nanomoles per gram of tissue.
Figure 6D:
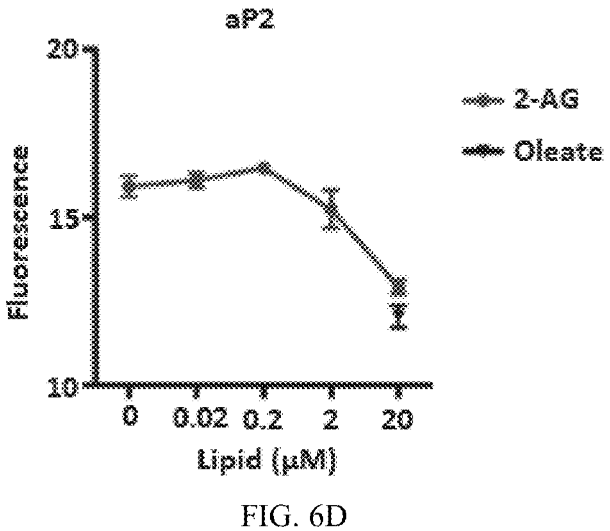
FIG. 6D is a line graph that shows the results of a parinaric acid binding assay analyzing the binding of aP2 to 2-AG or Oleate. n=3 for each data point. Error bars are standard error of the mean. The x-axis is micromolar lipid concentration, and the y-axis is fluorescence level.
Figure 6E:
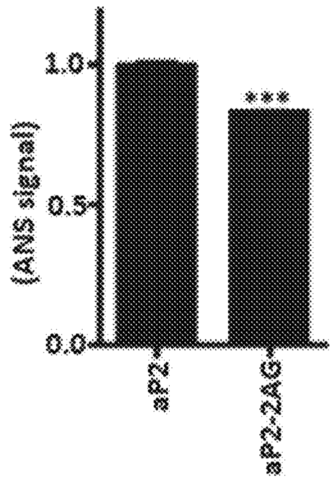
FIG. 6E is bar graph showing the results of an ANS assay after overnight incubation of aP2 alone or aP2 with 2-AG. n=3 for each condition. Fluorescence was normalized to the average fluorescence in aP2 alone.

For example, the assay may measure the formation of complexes between aP2, 2-AG, and/or 2-AG/aP2 and the compound being tested or examine the degree to which the formation of a complex between 2-AG/aP2 and CB1 is interfered with by the compound being tested. Thus, the present invention provides methods of identifying compounds comprising contacting a compound with aP2, 2-AG, and/or 2-AG/aP2 and assaying (i) for the presence of a complex between aP2, 2-AG, and/or 2-AG/aP2 and the compound or (ii) for the presence of a complex between 2-AG/aP2 and CB1. In such competitive binding assays, aP2, 2-AG, and/or 2-AG/aP2 can be labelled. Free 2-AG/aP2 is separated from that present in a complex and the amount of free (i.e. uncomplexed) label is a measure of the binding of the compound being tested to aP2, 2-AG, and/or 2-AG/aP2 or its interference with binding of the 2-AG/aP2 to CB1, respectively. Examples of competitive binding assays that can be utilized include 8-Anilinonaphthalene-1-sulfonic acid (ANS) binding assay (See Examples 9, 10, and 17; FIGS. 3*e* and 6*e*) and microscale thermophoresis (See example 17 and FIG. 3*f*).

The identification of a compound capable of neutralizing 2-AG/aP2 agonism of CB1 can further be confirmed in additional assays, for example, cell based biological assays or cell-free phosphorylation assays known in the field. A sequence for facilitating the detection or purification of bound 2-AG/aP2:CB1 complex or 2-AG/aP2:compound complex, such as the sequence containing a histidine residue or a continuous sequence thereof (poly-His), a c-Myc partial peptide (Myc-tag), a hemagglutinin partial peptide (HA-tag), a Flag partial peptide (Flag-tag), a glutathione-S-transferase (GST), a maltose-binding protein (MBP), botinylation, labeling with a fluorescent substance (such as a fluorescein), an Eu chelate, a chromophore, a luminophore, an enzyme, or a radioisotope (such as 125I or tritium); or binding of a compound having a hydroxysuccinimide residue, a vinyl pyridine residue, etc. for facilitating the binding to a solid phase (such as a container or a carrier), may be introduced into the amino terminal, the carboxy terminal, or an intermediate region of the amino acid sequence of aP2, CB1, or the compound, if the compound is an antibody or fragment thereof, and such proteins can be used during the screen.

In one embodiment, the present invention provides a method of identifying compounds capable of neutralizing 2-AG/aP2 agonism of CB1 utilizing eukaryotic cells expressing CB1 and analyzing the biological effects the compound has on 2-AG/aP2 agonism of CB1. Such cells, either in viable or fixed form, can be used for standard binding assays. For example, the assay may measure the formation of complexes between 2-AG/aP2 and CB1 in the presence of the compound or examine the degree to which biological activity of CB1 in the presence of 2-AG/aP2 is interfered with by the compound. Thus, the present invention provides methods of identifying compounds comprising contacting a compound and aP2, 2-AG, and/or 2-AG/aP2 and assaying (i) for the presence of a complex between the 2-AG/aP2 and CB1 or (ii) for inhibition of 2-AG/aP2 agonism on CB1 by measuring the biological effect of CB1. The influence of the compound on a biological activity of CB1 can be determined by methods well known in the art. In such activity assays the biological activity of CB1 is typically monitored by provision of a reporter system. For example, this may involve provision of a natural or synthetic substrate that generates a detectable signal in proportion to the degree to which it is acted upon by the biological activity of CB1 stimulation, for example, the measurement of a AMPK de-phosphorylation or phosphorylation, cyclic AMP formation, MAPK phosphorylation, DNL production, or guanosine 5'-O-(3-[$^{35}$S]thio)triphosphate([$^{35}$S]-GTPS) binding, for example as described in Janero et al., Molecular-Interaction and Signaling Profiles of AM3677, a Novel Covalent Agonist Selective for the Cannabinoid 1 Receptor. ACS Chem. Neurosci. (2015) Vol. 6(8):1400-1410.

The cell-based assay includes a cell that expresses CB1, either endogenously or recombinantly. CB1, as expressed, may be in the state of a monomer, a dimer or a multimer, as long as it is capable of eliciting a measurable biological affect upon stimulation by 2-AG/aP2 binding. CB1 may be derived from any organism such as human beings, mice, rat, cattle, pig, or rabbit. In one embodiment, the CB1 expressed is of human nature and derived from the endogenous human CB1 protein (UniProtKB-P21554 (CNR1_HUMAN)). CB1 may be extracted from a cell or tissue existing in nature, and may be extracted from a cell or tissue which expresses the subunit by a genetic engineering procedure. CB1 may be purified or unpurified. CB1 produced by a genetic engineering procedure having a reported amino acid sequence or a variant amino acid sequence obtained by genetic mutation can be used as long as it substantially maintains the activity.

In one embodiment, the assay is a cell-free assay and the compound is brought into contact with aP2, 2-AG, and/or 2-AG/aP2 in a liquid phase, or alternatively aP2, 2-AG, and/or 2-AG/aP2 is fixed to a solid phase (such as a column) and then contacted with the compound. For example, the 2-AG/aP2 may be fixed to the solid phase by biotin/streptavidin, by using a reactable amino group, such as a hydroxysuccinimide group, by using a reactive carboxyl group on a surface, such as a hydrazine group, or by using a group reactable with a thiol group on a surface, such as a vinyl pyridine group. For example, 2-AG/aP2 may be fixed to the solid phase (such as a column) by attaching to a solid phase composed of a polystyrene resin or a glass using the electrostatic attractive force or the intermolecular force, by binding 2-AG/aP2 to a solid phase obtained by immobilizing an antibody against an amino acid sequence added to aP2 and/or 2-AG/aP2 (such as poly-His, Myc-tag, HA-tag, Flag-tag, GST, or MBP), by binding 2-AG/aP2 attached with poly-His to a solid phase having on the surface a metal chelate, by binding 2-AG/aP2 attached with GST to a solid phase having on the surface a glutathione, or by binding 2-AG/aP2 attached with MBP to a solid phase having on the surface a sugar such as maltose. 2-AG/aP2 may also be fixed to the solid phase by another generally known method.

The contacting step of the compound with 2-AG/aP2 may be conducted, for example, by mixing a solution containing them. Alternatively, if, for example, 2-AG/aP2 or, alternatively the compound, is fixed to a solid phase such as a column, tube, or a multi-well plate, adding a solution containing the non-bound compound.

Compounds that are found to bind to aP2, 2-AG, and/or 2-AG/aP2 can be further tested in a cell free assay to determine the ability to prevent 2-AG/aP2 binding of CB1. For example, in one embodiment, the binding of 2-AG/aP2 contained in a liquid phase or fixed to a solid phase (such as a column, container, or a carrier) with CB1 can be measured in the presence and absence of the compound respectively, and the change of the binding depending on the addition of the compound is observed, to evaluate the inhibitory effect of the compound on the binding of 2-AG/aP2 to CB1. The binding of 2-AG/aP2 to CB1 may be measured with or without separating them. For example, 2-AG/aP2, CB1, and 2-AG/aP2 bound to CB1 (2-Ag/aP2:CB 1) may be separated by a gel filtration method, a column method using an affinity resin, an ion exchange resin, etc., a centrifugation method, or a washing method. For example, the amount of 2-AG/aP2 bound to CB1, or amount of 2-AG/aP2 unbound to CB1, may be measured after separating 2-AG/aP2 bound to CB1, CB1, and unbound 2-AG/aP2 from the liquid phase by the gel filtration method or the column method (an affinity resin, an ion exchange resin, etc.). In the case of fixing 2-AG/aP2 to the solid phase (such as a column, container or carrier), the solid phase (such as the column, container, or carrier) may be separated from a liquid phase by centrifugation, washing, distributive segregation, precipitation, etc., both in the presence and absence of the compound. In this case, the binding amount may be obtained directly by measuring the amount of CB1 bound to the separated solid phase (such as the column, container or carrier), or indirectly by measuring the amount of CB1 remaining in the liquid phase, both in the presence and absence of the compound. The CB1 in the liquid phase may be separated by an immunoprecipitation method using a protein or an antibody specifically reactable with CB1, as well as a gel filtration method, a column method using an affinity resin, an ion exchange resin, etc., a centrifugation method, or a washing method. The binding amount of 2-AG/aP2 and CB1 may be obtained directly by measuring the amount of the separated 2-AG/aP2 or CB1, or indirectly by measuring the amount of 2-AG/aP2 or CB1 contained in a fraction separated from fractions containing the bound 2-AG/aP2 and CB1.

In the methods above, the amount of 2-AG/aP2:CB1 and 2-AG/aP2:compound contained in a solution may be measured using, for example, 2-AG/aP2 labeled with biotin, a radioisotope, a fluorophore, a chromophore, or a chemiluminescent moiety. For example, the amount of the biotin-labeled 2-AG/aP2 may be measured by using a protein capable of binding to the biotin with high affinity such as avidin, streptavidin, or a variant protein thereof (hereinafter referred to as the avidins) such that avidins are labeled with the radioisotope, the fluorophore, the luminophore, or the enzyme, which can be easily detected, and bound to the biotin-labeled compound. The radioactive substance may be measured using a common radiation measuring apparatus such as a scintillation counter, a gamma counter, or a GM meter. The fluorophore, the chromophore, and the luminophore may be measured using a fluorescence measuring apparatus, an absorptiometer, and a luminescence measuring apparatus respectively. The amount of the enzyme-labeled compound can be easily measured using a compound that is converted by the enzyme to a chromogenic, fluorescent, or luminescent compound.

The amount of the 2-AG/aP2 bound or unbound contained in a solution may be measured as follows. For example, the 2-AG/aP2 labeled with the biotin, the fluorescent substance (such as the fluorescein), the Eu chelate, the chromophore, the luminophore, or the radioisotope (such as $^{125}$I or tritium) may be measured in the same manner as above. The biotinylated 2-AG/aP2 may be measured by an immunoprecipitation method, an Western blot method, a solid-phase enzyme immunoassay (an enzyme-linked immuno-sorbent assay: ELISA), or a sandwich assay such as a radioimmunoassay, by using a protein such as streptavidin; an antibody against 2-AG/aP2; an antibody against an amino acid sequence added to aP2 (such as poly-His, Myc-tag, HA-tag, Flag-tag, GST, or MBP); a molecule having a metal chelate against a poly-His-added 2-AG/aP2; a molecule having a glutathione against a GST-added 2-AG/aP2; a molecule having a sugar such as maltose against an MBP-added 2-AG/aP2; etc.

In a more specific example, 2-AG/aP2 having a Myc-tag sequence is contacted with a tritium-labeled CB1 using a 96-multi-well plate in the presence/absence of a compound in the presence of an anti-Myc antibody (a mouse-derived monoclonal antibody) and an anti-mouse immunoglobulin antibody-fixed SPA bead, and after a certain period, the binding amount of the 2-AG-aP2 and the tritium-labeled CB1 is measured using a scintillation counter, and the counted values obtained in the presence/absence of the compound are compared, whereby the inhibitory effect of the compound against the binding of 2-AG/aP2 to CB1 is measured.

The method for measuring the inhibitory activity of the compound against the binding of 2-AG/aP2 to CB1 is not particularly limited. For example, the inhibitory activity may be measured by fixing 2-AG/aP2 to the solid phase; contacting 2-AG/aP2 with CB1 in the presence or absence of a compound; and measuring the amount of the CB1 bonded to 2-AG/aP2 on the solid phase to measure the inhibitory activity of the compound against the binding of 2-AG/aP2 to CB1. Alternatively, the method comprises fixing the CB1 to the solid phase; contacting the CB1 with 2-AG/aP2 in the presence or absence of a compound; and measuring the amount of 2-AG/aP2 bonded to the solid phase to measure the inhibitory activity of the compound against the binding of 2-AG/aP2 to CB1. A further alternative includes contacting the 2-AG/aP2 with CB1 in the presence or absence of a compound; and measuring the binding amount of the 2-AG/aP2 and CB1 to measure the inhibitory activity of the compound against the binding of 2-AG/aP2 to CB1. In any of the methods above for example, the binding amount obtained by the contact in the presence of the compound may be compared with the binding amount obtained by the contact in the absence of the compound, to measure the inhibitory activity of the compound against the binding of 2-AG/aP2 to CB1.

In one embodiment, the assay is a cell-based assay, wherein the method for identifying the compound by measuring the inhibitory activity of the compound against the binding of 2-AG/aP2 to CB1 uses a cell, a tissue, or an extract thereof containing CB1. The cell or tissue substantially containing CB1 may be derived from any organism and may be any cell or tissue, although preferably a mammal cell or tissue, including a human cell or tissue. The cell or tissue may be one in which CB1 is endogenously expressed or is expressed by a genetic engineering procedure.

Figure 1B:
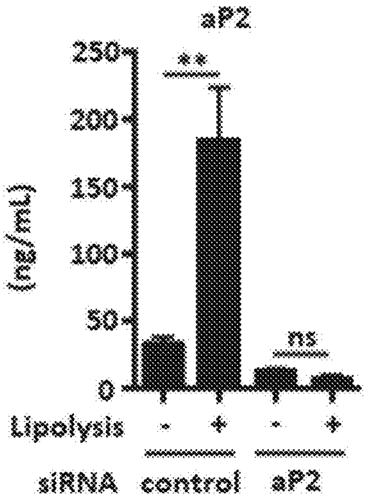
FIG. 1B is a bar graph that shows aP2 levels in the conditioned media from control or aP2 knockdown 3T3L1 adipocytes before and after 1 μM IBMX stimulation. n=3 in each condition. Error bars are standard error of the mean. The x-axis is the treatment group, and the y-axis is aP2 levels measured in nanograms per milliliter.
Figure 1C:
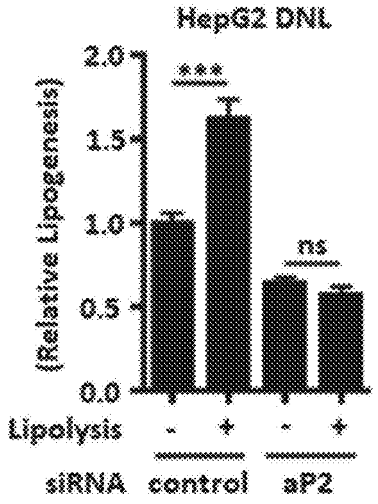
FIG. 1C is a bar graph that shows DNF in HepG2 cells were treated with conditioned media from control or aP2 knockdown 3T3L1 adipocytes before and after 1 μM IBMX stimulation. DNL was analyzed by scintillation count, normalized to protein concentration and expressed relative to the basal condition. n=4 in each condition. Error bars are standard error of the mean. The x-axis is treatment group, and the y-axis is relative lipogenesis.
Figure 1D:
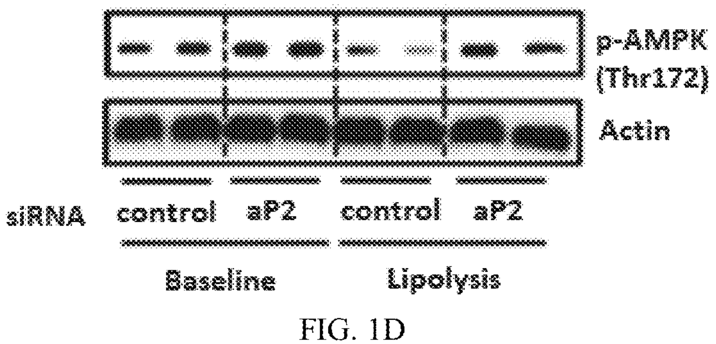
FIG. 1D shows p-AMPK as measured by western blot HepG2 cells were treated with conditioned media from control or aP2 knockdown 3T3L1 adipocytes before and after 1 μM IBMX stimulation.
Figure 1E:
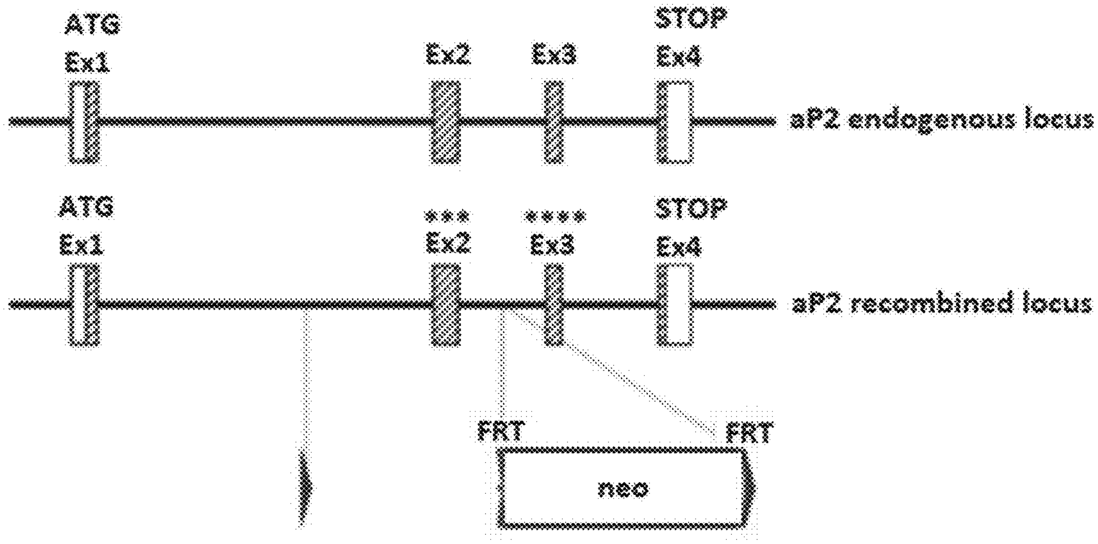
FIG. 1E shows a schematic representation of the endogenous aP2 locus and the humanized floxed allele. *: amino acid mutations for humanization. The arrow is the loxP site.
Figure 1F:
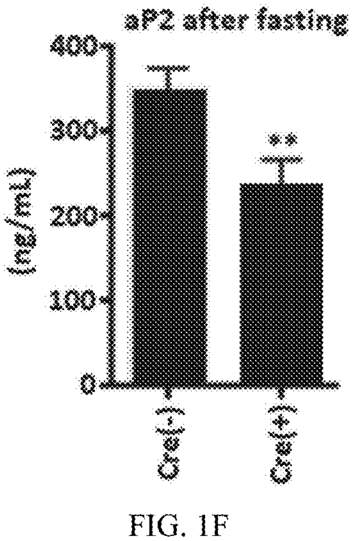
FIG. 1F is a bar graph that shows aP2 levels in the serum from FABP4$^{f/f}$ and FABP4$^{adip-/-}$ mice fasted for 22 hours. n=15 and 10 for FABP4$^{f/f}$ and FABP4$^{adip-/-}$ mice, respectively. Error bars are standard error of the mean. The x-axis is the treatment group, and the y-axis is aP2 level measured in nanograms per milliliter.
Figure 1G:
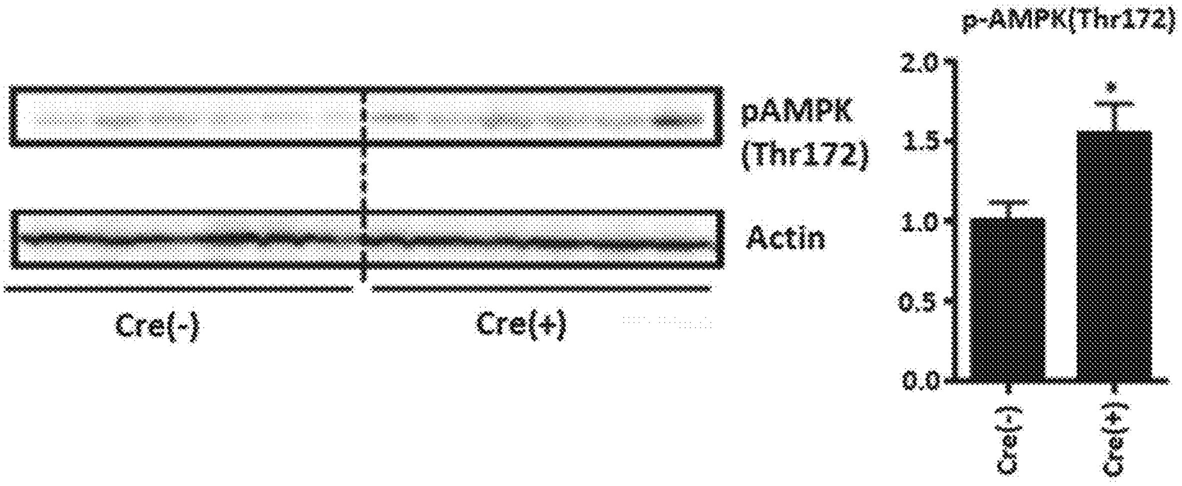
FIG. 1G shows p-AMPK levels as measured by western blot in the analysis of liver from FABP4$^{f/f}$ and FABP4$^{adip-/-}$ mice fasted for 22 hours. n=10 and 11 mice for FABP4$^{f/f}$ and FABP4$^{adip-/-}$ mice, respectively. Error bars are standard error of the mean.

In one embodiment, a cell population expressing CB1 is contacted with a solution comprising 2-AG, aP2, and/or 2-AG/aP2, and the biological activity of CB1 is measured in the presence and absence of a compound. CB1 biological activity generally refers to any observable effect resulting from the interaction between the CB1 and its agonistic binding partner 2-AG/aP2. The biological activity may be 2-AG/aP2 binding to CB 1, detection of CB1-mediated intracellular signal transduction; or determination of an end-point physiological effect. Representative, but non-limiting, examples of CB1 biological activity upon agonistic stimulation by 2-AG/aP2 include, but are not limited to, signaling and regulation of the processes discussed herein, e.g., suppression of downstream AMPK phosphorylation, phosphorylation of mitogen-activated protein kinases (MAPK), such as p42/p44 MAPK, p38 MAPK and c-Jun N-terminal kinase, increased DNL production, increased VLDL production, and/or inhibition of cyclic AMP formation. In one embodiment, the compound is a small molecule, a ligand, an antibody, antigen binding agent, or antibody fragment that binds to aP2, 2-AG, and or 2-AG/aP2 and neutralizes the ability of 2-AG/aP2 to agonize CB1. Methods of measuring biological effect of CB1 stimulation are known in the art and non-limiting examples, for example relating to AMPK phosphorylation (see Example 7 and 15; FIGS. 1*d*, 1*g*, and 3j), VLDL production (See examples 4 and 18; FIGS. 4*a*, 4*d*, 4*g*, 7*b*, and 7*c*), and DNL production (See examples 4, 16, and 17; FIGS. 3*b*, 3*i*, 3*k*, 31, and 6*a*), are described herein and in the Examples below.

In one non-limiting illustrative example, the cellular assay can be performed with varying concentrations of 2-AG/aP2, CB1, and/or compound to confirm, for example, the efficacy of the ability of the compound to interfere in 2-AG/aP2 agonizing CB1. For example, as described in the fifth aspect of the invention above, the first cellular assay of the fourth aspect of the present invention may be conducted as follows. 1 equivalent of the compound of interest is added to a solution of cells expressing CB1 in the presence of 1 equivalent of AP2 and 1 equivalent of 2-AG. The activity of CB1 is then measured using any method described herein or known in the art. In a typical embodiment, the concentration of the compound of interest is equal to or higher than that of AP2 and 2-AG in the cellular assay. In one embodiment, the concentration of the compound of interest is about 1, 2, 3, 4, 5, 10, 15, or 20 equivalents and the concentration of AP2 and 2-AG is about 1 equivalent. Methods to measure the activity of CB1 in the presence of the compound of interest include those described herein and discussed in the paper by Thomas D. Pollard "A Guide to Simple and Informative Binding Assays", MBOC; 2010; vol. 21 no. 23 4061.

In one non-limiting illustrative example, the second cellular assay of the fifth aspect of the present invention may be conducted as follows. 1 equivalent of the compound of interest is added to a solution of cells expressing CB1 in the presence of 20 equivalents of AP2 and 20 equivalents of 2-AG. The activity of CB1 is then measured using any method described herein or known in the art. In a typical embodiment, the concentration of the compound of interest is less than that of AP2 and 2-AG in the cellular assay (i.e. AP2 and 2-AG are saturated with respect to the compound of interest). In one embodiment, the concentration of the AP2 and 2-AG is about 5, 10, 15, 20, 25, 30, 35, or 40 equivalents and the concentration of the compound of interest is 1 equivalent.

In one embodiment, the equivalency of the compound of interest to 2-AG and AP2 is not known and instead a concentration of compound is used.

In one non-limiting illustrative example, the cellular assays of the sixth aspect of the present invention may be conducted as follows. 0.5 equivalent of the compound of interest is added to a solution of cells expressing CB1 in the presence of 1 equivalent of AP2 and 1 equivalent of 2-AG. The activity of CB1 is then measured using any method described herein or known in the art. Then the assay is serially repeated using 1 equivalent of the compound of interest, followed by 1.5 equivalents, 2 equivalents, etc. In one embodiment, the above procedure is conducted via serial dilution, starting with the highest concentration of compound and diluting it repeatedly to attain the lowest concentration. Methods to measure the activity of CB1 in the presence of the compound of interest include those described herein and discussed in the paper by Thomas D. Pollard "A Guide to Simple and Informative Binding Assays", MBOC; 2010; vol. 21 no. 23 4061. In one embodiment, the concentration of the compound of interest is varied logarithmically for example 100 equivalents, 10 equivalents, 1 equivalent, and 0.1 equivalents of compound. In another embodiment, the equivalents of compound is not known and instead a concentration of the compound is varied, for example 100 mM, 10 mM, 1 mM, 100 nM, 10 nM, and 1 nM could be the concentrations used.

Methods for selecting a compound, for example an antibody, that selectively bind to 2-AG/aP2 over aP2 alone are also provided. Methods for identifying preferably binding antibodies are generally known in the field. In one embodiment, provided herein is a method of identifying an antibody that selectively binds 2-AG/aP2 over aP2 generally comprising administering to a non-human animal, for example a rabbit, mouse, rat, or goat, a heterologous 2-AG/aP2 protein complex, for example human 2-AG/aP2, in order to raise antibodies against the heterologous 2-AG/aP2 in complex, isolating said antibodies, subjecting said antibodies to one or more binding assays measuring the binding affinity to 2-AG/aP2 and aP2 alone, for example a competitive binding assay, wherein antibodies that preferably bind 2-AG/aP2 over aP2 are isolated for use to neutralize 2-AG/aP2 agonism of CB1. For example, antibodies to 2-AG/aP2 can be raised using hybridomas accomplished by standard procedures well known to those skilled in the field of immunology. Preferred methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference.

Fusion partner cell lines and methods for fusing and selecting hybridomas and screening for mAbs are well known in the art. The 2-AG/aP2 specific mAb can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

It should be noted that the methods for identifying the compounds above are considered to be illustrative and not restrictive.

aP2 and/or 2-AG/aP2 complex Neutralizing Compounds

In one aspect of the invention, methods for modulating CB1 signaling are provided which include administering to a subject a compound that neutralizes the agonism of CB1 by 2-AG/aP2 by inhibiting the formation of the 2-AG/aP2 complex or the interaction of the 2-AG/aP2 complex with CB1 by directly targeting 2-AG/aP2, 2-AG, or aP2, effectively neutralizing 2-AG/aP2's ability to stimulate CB1. In one embodiment, the compound is an anti-aP2 and/or anti-2-AG/aP2 complex antibody, antibody fragment, or antigen binding agent, including, for example a polyclonal antibody, a monoclonal antibody, antibody fragment, or antigen binding agent. In one embodiment, the compound is a humanized monoclonal antibody or antigen binding agent.

In one aspect of the present invention, an antibody or antigen binding agent is administered to a subject wherein the antibody comprises at least one, or more than one, of the CDR regions provided in Table 2.

TABLE 2

Anti-aP2 Antibody Complementarity Determining Regions

| Protein | Seq. ID No. | Sequence |
|---|---|---|
| CDRL1 | 7 | QASEDISRYLV |
| CDRL1 variant 1 | 22 | SVSSSISSSNLH |
| CDRL2 | 8 | KASTLAS |
| CDRL2 variant 1 | 23 | GTSNLAS |
| CDRL3 | 9 | QCTYGTYAGSFFYS |
| CDRL3 variant 1 | 10 | QATYGTYAGSFFYS |
| CDRL3 variant 2 | 11 | QQTYGTYAGSFFYS |
| CDRL3 variant 3 | 12 | QHTYGTYAGSFFYS |
| CDRL3 variant 4 | 13 | QQASHYPLT |
| CDRL3 variant 5 | 24 | QQWSHYPLT |
| CDRH1 | 14 | GFSLSTYYMS |

TABLE 2-continued

| Anti-aP2 Antibody Complementarity Determining Regions | | |
|---|---|---|
| Protein | Seq. ID No. | Sequence |
| CDRH1 variant 1 | 15 | GYTFTSNAIT |
| CDRH1 variant 2 | 25 | GYTFTSNWIT |
| CDRH2 | 16 | IIYPSGSTYCASWAKG |
| CDRH2 variant 1 | 17 | IIYPSGSTYSASWAKG |
| CDRH2 variant 2 | 18 | DISPGSGSTTNNEKFKS |
| CDRH2 variant 3 | 26 | DIYPGSGSTTNNEKFKS |
| CDRH3 | 19 | PDNDGTSGYLSGFGL |
| CDRH3 variant 1 | 20 | PDNEGTSGYLSGFGL |
| CDRH3 variant 2 | 21 | LRGFYDYFDF |
| CDRH3 variant 3 | 27 | LRGYYDYFDF |

In one embodiment, the 2-AG/aP2 neutralizing antibody or antigen binding fragment is a monoclonal antibody or antigen binding fragment comprising a light chain wherein the variable domain comprises one, two, or three CDRs independently selected from CDRL1 (QASEDISRYLV) (Seq. ID No. 7), CDRL1 variant 1 (SVSSSISSSNLH) (Seq. ID No. 22), CDRL2 (KASTLAS) (Seq. ID No. 8), CDRL2 variant 1 (GTSNLAS) (Seq. ID No. 23), CDRL3 (QCTYGTYAGSFFYS) (Seq. ID. No. 9), CDRL3 variant 1 (QATYGTYAGSFFYS) (Seq. ID No. 10), CDRL3 variant 2 (QQTYGTYAGSFFYS) (Seq. ID No. 11), CDRL3 variant 3 (QHTYGTYAGSFFYS) (Seq. ID No. 12), CDRL3 variant 4 (QQASHYPLT) (Seq. ID No. 13), or CDRL3 variant 5 (QQWSHYPLT) (Seq. ID No. 24). In one embodiment, the antibody or antigen binding agent comprises a light chain variable region comprising CDRL1 (Seq. ID No. 7), CDRL2 (Seq. ID No. 8), and CDRL3 (Seq. ID No. 9). In one embodiment, the antibody or antigen binding agent comprises a light chain variable region comprising CDRL1 (Seq. ID No. 7), CDRL2 (Seq. ID No. 8), and CDRL3 variant 1 (Seq. ID No. 10). In one embodiment, the antibody or antigen binding agent comprises a light chain variable region comprising CDRL1 (Seq. ID No. 7), CDRL2 (Seq. ID No. 8), and CDRL3 variant 2 (Seq. ID No. 11). In one embodiment, the antibody or antigen binding agent comprises a light chain variable region comprising CDRL1 (Seq. ID No. 7), CDRL2 (Seq. ID No. 8), and CDRL3 variant 3 (Seq. ID No. 12).

In one embodiment, the 2-AG/aP2 neutralizing antibody or antigen binding fragment comprises a light chain variable region comprising CDRL3 variant 4 (Seq. ID No. 13), wherein the antibody has a KD of about $\geq 10^{-7}$ M. In one embodiment, the antibody or antigen binding agent comprises a light chain variable region comprising CDRL1 variant 1 (Seq. ID No. 22), CDRL2 variant 1 (Seq. ID No. 23), and CDRL3 variant 4 (Seq. ID No. 13). In one embodiment, the antibody or antigen binding agent comprises a light chain variable region comprising CDRL3 variant 4 (Seq. ID No. 13) and a heavy chain variable region comprising CDHR1 variant 1 (GYTFTSNAIT) (Seq. ID No. 15), CDRH2 variant 2 (DISPGSGSTTNNEKFKS) (Seq. ID No. 18), and, in one embodiment, CDRH3 variant 2 (LRGFYDYFDF) (Seq. ID No. 21).

In one embodiment, the 2-AG/aP2 neutralizing antibody or antigen binding fragment comprises one, two, or three CDRs selected from CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), and CDRL3 variant 4 (Seq. ID No. 13), and has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

In one embodiment, the 2-AG/aP2 neutralizing antibody or antigen binding fragment comprises a light chain wherein the variable domain comprises one, two, or three CDRs independently selected from an amino acid sequence that is at least 80%, 85%, 90%, or 95% homologous with CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13). In one embodiment, the antibody or antigen binding agent has a Kd of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region. In one embodiment, the antibody or antigen binding agent comprises a light chain wherein the variable domain comprises one, two, or three CDRs independently selected from an amino acid sequence that has one or more (for example, 1, 2, 3, or 4) amino acid substitutions, additions, or deletions as compared with CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13).

In one embodiment the 2-AG/aP2 neutralizing antibody or antigen binding fragment comprises a light chain wherein the variable domain comprises one, two, or three CDRs selected from CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13), and one, two, or three CDRs selected from CDRH1 (GFSLSTYYMS) (Seq. ID NO. 14), CDRH1 variant 1 (Seq. ID No. 15), CDRH1 variant 2 (GYTFTSNWIT) (Seq. ID No. 25), CDRH2 (IIYPSGSTYCASWAKG) (Seq. ID No. 16), CDRH2 variant 1 (IIYPSGSTYSASWAKG) (Seq. ID No. 17), CDRH2 variant 2 (Seq. ID No. 18), CDRH2 variant 3 (DIYPGSGSTTNNEKFKS) (Seq. ID No. 26), CDHR3 (PDNDGTSGYLSGFGL) (Seq. ID No. 19), CDRH3 variant 1 (PDNEGTSGYLSGFGL) (Seq. ID No. 20), CDRH3 variant 2 (Seq. ID No. 21), or CDRH3 variant 3 (LRGYYDYFDFW) (Seq. ID No. 27). In one embodiment, the antibody or antigen binding agent comprises a heavy chain variable region comprising CDRH1 variant 1 (Seq. ID No. 15), CDRH2 variant 2 (Seq. ID No. 18), and CDRH3 variant 3 (Seq. ID No. 27). In one embodiment, the antibody or antigen binding agent comprises a heavy chain variable region comprising CDRH1 variant 1 (Seq. ID No. 15), CDRH2 variant 2 (Seq. ID No. 18), and CDRH3 variant 2 (Seq. ID No. 21). In one embodiment, the antibody or antigen binding agent has a Kd of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

In one embodiment, the 2-AG/aP2 neutralizing antibody or antigen binding fragment comprises one, two, or three CDRs selected from CDRH1 (Seq. ID NO. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21), and has a KD of about $\geq 10^{-7}$ M. In one embodiment, the antibody or antigen binding agent comprises CDRs CDRH1 (Seq. ID No. 14), CDRH2 (Seq. ID No. 16), and CDRH3 (Seq. ID No. 19). In one embodiment, the antibody or antigen binding agent comprises CDRs CDRH1 (Seq. ID No. 14), CDRH2 variant 1 (Seq. ID No. 17), and CDHR3 variant 1 (Seq. ID No. 20). In one embodiment, the antibody comprises CDRs CDRH1 variant 1 (Seq. ID No. 15) and CDRH2 variant 2 (Seq. ID No. 18). In one embodiment, the antibody comprises CDRs CDRH1 variant 1 (Seq. ID No. 15), and CDRH2 variant 2 (Seq. ID No. 18), and CDRH3 variant 2 (Seq. ID No. 21). In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region. In one embodiment, the antibody or antigen binding agent comprises one, two, or three CDRs selected from an amino acid sequence that has one or more (for example, 1, 2, 3, or 4) amino acid substitutions, additions, or deletions as compared to CDRH1 (Seq. ID NO. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21).

In one embodiment, the 2-AG/aP2 neutralizing antibody or antigen binding fragment comprises a heavy chain wherein the variable domain comprises one, two, or three CDRs selected from an amino acid sequence that is at least 80%, 85%, 90%, or 95% homologous with CDRH1 (Seq. ID No. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21). In one embodiment, the antibody or antigen binding agent has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

CDRs can be altered or modified to provide for improved binding affinity, minimize loss of binding affinity when grafted into a different backbone, or to decrease unwanted interactions between the CDR and the hybrid framework as described further below.

In one aspect of the present invention, the antibodies and fragments for administration are humanized.

Construction of CDR-grafted antibodies is generally described in European Patent Application EP-A-0239400, which discloses a process in which the CDRs of a mouse monoclonal antibody are grafted onto the framework regions of the variable domains of a human immunoglobulin by site directed mutagenesis using long oligonucleotides, and is incorporated herein. The CDRs determine the antigen binding specificity of antibodies and are relatively short peptide sequences carried on the framework regions of the variable domains.

The human variable heavy and light chain germline subfamily classification can be derived from the Kabat germline subgroup designations: VH1, VH2, VH3, VH4, VH5, VH6 or VH7 for a particular VH sequence and JH1, JH2, JH3, JH4, JH5, and JH6 for a for a particular variable heavy joining group for framework 4; VK1, VK2, VK3, VK4, VK5 or VK6 for a particular VL kappa sequence for framework 1, 2, and 3, and JK1, JK2, JK3, JK4, or JK5 for a particular kappa joining group for framework 4; or VL1, VL2, VL3, VL4, VL5, VL6, VL7, VL8, VL9, or VL10 for a particular VL lambda sequence for framework 1, 2, and 3, and JL1, JL2, JL3, or JL7 for a particular lambda joining group for framework 4.

The general framework of the light chain comprises the structures selected from FR1-CDRL1-FR2-CDRL2-FR3-CDRL3-FR4 and FR1-CDRL1-FR2-CDRL2-FR3-CDRL3-FR4-CL, and variations thereof, wherein the CDR regions are selected from at least one variable light chain CDR selected from Seq. ID Nos. 7-13 or Seq. ID Nos. 22-24, the framework regions are selected from either an immunoglobulin kappa light chain variable framework region, or an immunoglobulin lambda light chain variable framework region, and an immunoglobulin light chain constant region from either a kappa light chain constant region when the framework region is a kappa light chain variable framework region, or a lambda light chain constant region when the framework region is a lambda light chain variable framework region.

In one embodiment, the general framework of the heavy chain regions contemplated herein comprises the structures selected from FR1-CDRH1-FR2-CDRH2-FR3-CDRH3-FR4, FR1-CDRH1-FR2-CDRH2-FR3-CDRH3-FR4-CH1, FR1-CDRH1-FR2-CDRH2-FR3-CDRH3-FR4-CH1-Hinge-CH2 for IgG, IgD, and IgA immunoglobulin classes and FR1-CDRH1-FR2-CDRH2-FR3-CDRH3-FR4-CH1-CH2 for IgM and IgE immunoglobulin classes, FR1-CDRH1-FR2-CDRH2-FR3-CDRH3-FR4-CH1-Hinge-CH2-CH3 for IgG, IgD, and IgA immunoglobulin classes, FR1-CDRH1-FR2-CDRH2-FR3-CDRH3-FR4-CH1-CH2-CH3 for IgM and IgE immunoglobulin classes, and FR1-CDRH1-FR2-CDRH2-FR3-CDRH3-FR4-CH1-CH2-CH3-CH4 for IgM and IgE immunoglobulin classes, and variations thereof, wherein the CDR regions are selected from at least one variable heavy chain CDR selected from Seq. ID Nos. 14-21 and 27, and the framework regions are selected from heavy chain variable framework regions, and the heavy chain constant regions. IgA and IgM classes can further comprise a joining polypeptide that serves to link two monomer units of IgM or IgA together, respectively. In the case of IgM, the J chain-joined dimer is a nucleating unit for the IgM pentamer, and in the case of IgA it induces larger polymers.

The constant region domains of the antibody molecule for administration, if present, may be selected having regard to the proposed function of the antibody molecule, and in particular the effector functions which may be required. For example, the constant region domains may be human IgA, IgD, IgE, IgG or IgM domains. In particular embodiments, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

In one embodiment, the antibody administered comprises a variable light chain selected from Seq. ID. Nos. 28-36 or 37-40 (Table 3 below). In one embodiment, the antibody administered comprises a variable heavy chain selected from Seq. ID. Nos. 4, or 41-50 (Table 4 below). In one embodiment, the antibody administered comprises a variable light chain selected from Seq. ID. Nos. 28-40 and a variable heavy chain selected from Seq. ID. Nos. 4, or 41-50 or an antibody sequence which is 80% similar or more identical to Seq. ID. Nos. 28-40 and/or a variable heavy chain selected from Seq. ID. Nos. 4 or 41-50, for example 85%, 90%, 91%, 92%, 93%, 94%, 95% 96%, 97%, 98% or 99% over part or whole of the relevant sequence, for example a variable domain sequence, a CDR sequence or a variable domain sequence excluding the CDRs.

TABLE 3

Sequences of Humanized Anti-aP2 protein complex Light Chain Regions

| Protein | Seq. ID No. | Sequence |
|---|---|---|
| Rabbit Ab 909 VL-region | 28 | DVVMTQTPASVSEPVGGTVTIKCQASEDISRYLVWYQQKPGQPPK RLIYKASTLASGVPSRFKGSGSGTDFTLTISDLECDDAATYYCQCT YGTYAGSFFYSFGGGTEVVVE |
| 909 gL1 VL-region | 29 | DVVMTQSPSSLSASVGDRVTITCQASEDISRYLVWYQQKPGKAPK RLIYKASTLASGVPSRFKGSGSGTDFTLTISSLQPEDFATYYCQCTY GTYAGSFFYSFGGGTKVEIK |
| 909 gL1 VL + CL-region | 30 | DVVMTQSPSSLSASVGDRVTITCQASEDISRYLVWYQQKPGKAPK RLIYKASTLASGVPSRFKGSGSGTDFTLTISSLQPEDFATYYCQCTY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 909 gL10 VL-region | 31 | DVVMTQSPSSLSASVGDRVTITCQASEDISRYLVWYQQKPGKAPK RLIYKASTLASGVPSRFKGSGSGTDFTLTISSLQPEDFATYYCQATY GTYAGSFFYSFGGGTKVEIK |
| 909 gL10 VL + CL-region | 32 | DVVMTQSPSSLSASVGDRVTITCQASEDISRYLVWYQQKPGKAPK RLIYKASTLASGVPSRFKGSGSGTDFTLTISSLQPEDFATYYCQATY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 909 gL54 VL-region | 33 | DVVMTQSPSSLSASVGDRVTITCQASEDISRYLVWYQQKPGKAPK RLIYKASTLASGVPSRFKGSGSGTDFTLTISSLQPEDFATYYCQQTY GTYAGSFFYSFGGGTKVEIK |
| 909 gL54 VL + CL-region | 34 | DVVMTQSPSSLSASVGDRVTITCQASEDISRYLVWYQQKPGKAPK RLIYKASTLASGVPSRFKGSGSGTDFTLTISSLQPEDFATYYCQQTY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 909 gL55 VL-region | 35 | DVVMTQSPSSLSASVGDRVTITCQASEDISRYLVWYQQKPGKAPK RLIYKASTLASGVPSRFKGSGSGTDFTLTISSLQPEDFATYYCQHTY GTYAGSFFYSFGGGTKVEIK |
| 909 gL55 VL + CL-region | 36 | DVVMTQSPSSLSASVGDRVTITCQASEDISRYLVWYQQKPGKAPK RLIYKASTLASGVPSRFKGSGSGTDFTLTISSLQPEDFATYYCQHTY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 909 gL13 VL-region | 37 | DIQMTQSPSSLSASVGDRVTITCQASEDISRYLVWYQQKPGKAPK RLIYKASTLASGVPSRFSGSGSGTEFTLTISSLQPEDFATYYCQATY GTYAGSFFYSFGGGTKVEIK |
| 909 gL13 VL + CL-region | 38 | DIQMTQSPSSLSASVGDRVTITCQASEDISRYLVWYQQKPGKAPK RLIYKASTLASGVPSRFSGSGSGTEFTLTISSLQPEDFATYYCQATY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| 909 gL50 VL-region | 39 | DVVMTQSPSSLSASVGDRVTITCQASEDISRYLVWYQQKPGKAPK RLIYKASTLASGVPSRFKGSGSGTDFTLTISSLQPEDFATYYAQATY GTYAGSFFYSFGGGTKVEIK |
| 909 gL50 VL + CL-region | 40 | DVVMTQSPSSLSASVGDRVTITCQASEDISRYLVWYQQKPGKAPK RLIYKASTLASGVPSRFKGSGSGTDFTLTISSLQPEDFATYYAQATY GTYAGSFFYSFGGGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |

TABLE 4

Sequences of Humanized aP2/2-AG/aP2 protein complex Heavy Chain Regions

| Protein | Seq. ID No. | Sequence |
|---|---|---|
| Rabbit Ab 909 VH region | 41 | QSVEESGGRLVTPGTPLTLTCTVSGFSLSTYYMSWVRQAPGKGLE WIGIIYPSGSTYCASWAKGRFTISKASTTVDLKITSPTTEDTATYFC ARPDNDGTSGYLSGFGLWGQGTLVTVSS |
| 909gH1 VH region | 42 | EVQLQESGPGLVKPSGTLSLTCTVSGFSLSTYYMSWVRQPPGKGL EWIGIIYPSGSTYCASWAKGRFTISKASTTVDLKLSSVTAADTATY FCARPDNDGTSGYLSGFGLWGQGTLVTVSS |
| 909gH1 IgG4 VH + human γ-4P constant | 43 | EVQLQESGPGLVKPSGTLSLTCTVSGFSLSTYYMSWVRQPPGKGL EWIGIIYPSGSTYCASWAKGRFTISKASTTVDLKLSSVTAADTATY FCARPDNDGTSGYLSGFGLWGQGTLVTVSSASTKGPSVFPLAPCS RSTSESTAALGCLVKDYFPEPVTVSWNSGALTSGVHTFPAVLQSS GLYSLSSVVTVPSSSLGTKTYTCNVDHKPSNTKVDKRVESKYGPP CPPCPAPEFLGGPSVFLFPPKPKDTLMISRTPEVTCVVVDVSQEDPE VQFNWYVDGVEVHNAKTKPREEQFNSTYRVVSVLTVLHQDWLN GKEYKCKVSNKGLPSSIEKTISKAKGQPREPQVYTLPPSQEEMTKN QVSLTCLVKGFYPSDIAVEWESNGQPENNYKTTPPVLDSDGSFFL YSRLTVDKSRWQEGNVFSCSVMHEALHNHYTQK SLSLSLGK |
| 909gH14 VH region | 44 | EVQLQESGPG LVKPSGTLSLTCAVSGFSLSTYYMSWVRQP PGKGLEWIGIIYPSGSTYCASWAKGRFTISKASTKNTVDLKLSSVT AADTATYFCARPDNDGTSGYLSGFGLWGQGTLVTVSS |
| 909gH14 IgG4 VH + human γ-4P constant | 45 | EVQLQESGPGLVKPSGTLSLTCAVSGFSLSTYYMSWVRQPPGKGL EWIGIIYPSGSTYCASWAKGRFTISKASTKNTVDLKLSSVTAADTA TYFCARPDNDGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH15 VH region | 46 | EVQLQESGPGLVKPSGTLSLTCTVSGFSLSTYYMSWVRQPPGKGL EWIGIIYPSGSTYSASWAKGRFTISKASTKNTVDLKLSSVTAADTA TYFCARPDNEGTSGYLSGFGLWGQGTLVTVSS |
| 909gH15 IgG4 VH + human γ-4P constant | 47 | EVQLQESGPGLVKPSGTLSLTCTVSGFSLSTYYMSWVRQPPGKGL EWIGIIYPSGSTYSASWAKGRFTISKASTKNTVDLKLSSVTAADTA TYFCARPDNEGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH61 VH region | 48 | EVQLQESGPGLVKPSGTLSLTCAVSGFSLSTYYMSWVRQPPGKGL EWIGIIYPSGSTYCASWAKGRVTISKDSSKNQVSLKLSSVTAADTA VYYCARPDNDGTSGYLSGFGLWGQGTLVTVSS |
| 909gH61 IgG4 VH + human γ-4P constant | 49 | EVQLQESGPGLVKPSGTLSLTCAVSGFSLSTYYMSWVRQPPGKGL EWIGIIYPSGSTYCASWAKGRVTISKDSSKNQVSLKLSSVTAADTA VYYCARPDNDGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH62 VH region | 50 | EVQLQESGPGLVKPSGTLSLTCAVSGFSLSTYYMSWVRQPPGKGL EWIGIIYPSGSTYSASWAKGRVTISKDSSKNQVSLKLSSVTAADTA VYYCARPDNEGTSGYLSGFGLWGQGTLVTVSS |
| 909gH62 IgG4 VH + human γ-4P constant | 4 | EVQLQESGPGLVKPSGTLSLTCAVSGFSLSTYYMSWVRQPPGKGL EWIGIIYPSGSTYSASWAKGRVTISKDSSKNQVSLKLSSVTAADTA VYYCARPDNEGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW |

TABLE 4-continued

| Sequences of Humanized aP2/2-AG/aP2 protein complex Heavy Chain Regions | | |
|---|---|---|
| Protein | Seq. ID No. | Sequence |
| | | LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |

In one embodiment, the 2-AG/aP2 neutralizing antibody or antigen binding fragment is a Fab, Fab', or F(ab')2 antibody fragment comprising a light chain variable region selected from Seq. ID Nos. 29, 31, 33, 35, 37, or 38, and a heavy chain variable region selected from Seq. ID Nos. 42, 44, 46, 48, or 50.

In one embodiment, the 2-AG/aP2 neutralizing antibody or antigen binding fragment is a full length IgG1 antibody comprising the variable regions shown in Seq. ID Nos. 29, 31, 33, 35 37, or 38, for the light chain and Seq. ID Nos. 42, 44, 46, 48, or 50 for the heavy chain.

In one embodiment, the 2-AG/aP2 neutralizing antibody or antigen binding fragment is a full length IgG4 antibody comprising the variable regions shown in Seq. ID Nos. 29, 31, 37, 38, 33, or 35 for the light chain and Seq. ID Nos. 42, 44, 46, 48, or 50 for the heavy chain.

In one embodiment, the 2-AG/aP2 neutralizing antibody or antigen binding fragment is a full length IgG4P antibody comprising the variable regions shown in Seq. ID Nos. 29, 31, 33, 35, 37, or 38 for the light chain and Seq. ID Nos. 42, 44, 46, 48, or 50 for the heavy chain.

In one embodiment, the 2-AG/aP2 neutralizing antibody or antigen binding fragment comprises a light variable region of Seq. ID. No. 29, and a heavy variable region of Seq. ID. No. 42, 44, 46, 48, or 50; a light variable region of Seq. ID. No. 31, and a heavy variable region of Seq. ID. No. 42, 44, 46, 48, or 50; a light variable region of Seq. ID. No. 33, and a heavy variable region of Seq. ID. No. 42, 44, 46, 48, or 50; a light variable region of Seq. ID. No. 35, and a heavy variable region of Seq. ID. No. 42, 44, 46, 48, or 50; a light variable region of Seq. ID. No. 37, and a heavy variable region of Seq. ID. No. 42, 44, 46, 48, or 50; or a light variable region of Seq. ID. No. 38, and a heavy variable region of Seq. ID. No. 42, 44, 46, 48, or 50; a light variable region of Seq. ID. No. 29, 31, 33, 35, 37, or 38, and a heavy variable region of Seq. ID. No. 42; a light variable region of Seq. ID. No. 29, 31, 33, 35, 37, or 38, and a heavy variable region of Seq. ID. No. 44; a light variable region of Seq. ID. No. 29, 31, 33, 35, 37, or 38, and a heavy variable region of Seq. ID. No. 46; a light variable region of Seq. ID. No. 29, 31, 33, 35, 37, or 38, and a heavy variable region of Seq. ID. No. 48; or a light variable region of Seq. ID. No. 29, 31, 33, 35, 37, or 38, and a heavy variable region of Seq. ID. No. 50.

In one embodiment, the fusion protein administered comprises two domain antibodies, for example as a variable heavy (VH) and variable light (VL) pairing, optionally linked by a disulphide bond.

The antibody fragment administered may include Fab, Fab', F(ab')2, scFv, diabody, scFAb, dFv, single domain light chain antibodies, dsFv, a peptide comprising CDR, and the like.

In one aspect, provided herein is an antibody, for example a polyclonal or monoclonal antibody, an antibody fragment, or antigen binding agent that binds to the 2-AG/aP2 complex. In one embodiment, the antibody, antibody fragment, or antigen binding agent binds to the 2-AG/aP2 complex preferentially over aP2 and/or 2-AG alone. In one embodiment, the antibody, antibody fragment, or antigen binding agent binds to the 2-AG/aP2 complex and does not bind to aP2 and/or 2-AG alone. In one embodiment, the antibody, antibody fragment, or antigen binding agent binds to the 2-AG/aP2 complex with a KD≤$10^{-9}$ M.

Methods of producing antibodies, antibody fragments, or antigen binding agents are known in the art. See, e.g., US2011/0129464, incorporated herein by reference. For example, polyclonal antibodies are preferably raised in animals by multiple subcutaneous (SC) or intraperitoneal (IP) injections of the relevant antigen and an adjuvant, for example, 2-AG in complex with aP2. It may be useful to conjugate the relevant antigen, that is 2-AG/aP2 in complex, to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or R1N═C═NR, where R and R1 are different alkyl groups.

For example, animals are immunized against the 2-AG/aP2 complex antigen, by combining, e.g., 100 μg of the human aP2 in complex with 2-AG or 5 μg conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567), both incorporated herein by reference. In the hybridoma method, a mouse or other appropriate host animal, such as a hamster, is immunized as hereinabove described to elicit lymphocytes that produce or are capable of producing antibodies that will specifically bind to the protein used for immunization.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986) incorporated herein by reference).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et. al., Monoclonal Antibody Production Techniques and Applications, pp. 51-63 (Marcel Dekker, Inc., New York, 1987), both incorporated herein by reference).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (MA) or enzyme-linked immunosorbent assay (ELISA).

The binding affinity of the monoclonal antibody can, for example, be determined by the Scatchard analysis of Munson et al., Anal. Biochem., 107:220 (1980), incorporated herein by reference.

After hybridoma cells are identified that produce antibodies of the desired specificity, affinity, and/or activity, the clones may be sub-cloned by limiting dilution procedures and grown by standard methods (Goding, Monoclonal Antibodies: Principles and Practice, pp. 59-103 (Academic Press, 1986), incorporated herein by reference). Suitable culture media for this purpose include, for example, D-MEM or RPMI-1640 medium. In addition, the hybridoma cells may be grown in vivo as ascites tumors in an animal.

The monoclonal antibodies secreted by the sub-clones are suitably separated from the culture medium, ascites fluid, or serum by conventional antibody purification procedures such as, for example, protein A-Sepharose, hydroxyapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130:151-188 (1992) incorporated herein by reference.

In a further embodiment, monoclonal antibodies or antibody fragments can be isolated from antibody phage libraries generated using the techniques described in McCafferty et al., Nature, 348:552-554 (1990), incorporated herein by reference. Clackson et al., Nature, 352:624-628 (1991) and Marks et al., J. Mol. Biol., 222:581-597 (1991) incorporated herein by reference describe the isolation of murine and human antibodies, respectively, using phage libraries. Subsequent publications describe the production of high affinity (nM range) human antibodies by chain shuffling (Marks et al., Bio/Technology, 10:779-783 (1992) incorporated herein by reference), as well as combinatorial infection and in vivo recombination as a strategy for constructing very large phage libraries (Waterhouse et al., Nuc. Acids. Res., 21:2265-2266 (1993) incorporated herein by reference). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., Proc. Natl. Acad. Sci. USA, 81:6851(1984) incorporated herein by reference), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Methods for humanizing non-human antibodies have been described in the art, for example, methods to prepare human and humanized antibodies are provided in a number of publications, including U.S. Pat. Nos. 7,223,392, 6,090,382, 5,859,205, 6,090,382, 6,054,297, 6,881,557, 6,284,471, and 7,070,775 all incorporated herein by reference. Preferably, a humanized antibody has one or more amino acid residues introduced into it from a source which is non-human.

These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988) all incorporated herein by reference), by substituting hypervariable region sequences for the corresponding sequences of a human antibody. Accordingly, such "humanized" antibodies are chimeric antibodies (U.S. Pat. No. 4,816,567, incorporated herein by reference) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151:2296 (1993); Chothia et al., J. Mol. Biol., 196:901 (1987), both incorporated herein by reference). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), incorporated herein by reference).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding. Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and U.S. Pat. Nos. 5,591,669, 5,589,369 and 5,545,807, all incorporated herein by reference.

Alternatively, phage display technology (McCafferty et al., Nature 348:552-553 (1990) incorporated herein by reference) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., Current Opinion in Structural Biology 3:564-571(1993) incorporated herein by reference. Several sources of V-gene segments can be used for phage display. Clackson et al., Nature, 352:624-628 (1991) incorporated herein by reference isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905, all incorporated herein by reference.

As discussed above, human antibodies may also be generated by in vitro activated B cells (see U.S. Pat. Nos. 5,567,610 and 5,229,275, incorporated herein by reference).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985) incorporated herein by reference). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992) incorporated herein by reference). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458, all incorporated herein by reference. The antibody fragment may also be a "linear antibody", e.g., as described in U.S. Pat. No. 5,641,870 for example and incorporated herein by reference. Such linear antibody fragments may be monospecific or bispecific.

Techniques for generating antibodies have been described above. One may further select antibodies with certain biological characteristics, as desired, for example, preferential binding to the 2-AG/aP2 complex over aP2 and/or 2-AG.

Construction of CDR-grafted antibodies is generally described in European Patent Application EP-A-0239400, which discloses a process in which the CDRs of a mouse monoclonal antibody are grafted onto the framework regions of the variable domains of a human immunoglobulin by site directed mutagenesis using long oligonucleotides, and is incorporated herein. The CDRs determine the antigen binding specificity of antibodies and are relatively short peptide sequences carried on the framework regions of the variable domains.

The human variable heavy and light chain germline subfamily classification can be derived from the Kabat germline subgroup designations: VH1, VH2, VH3, VH4, VHS, VH6 or VH7 for a particular VH sequence and JH1, JH2, JH3, JH4, JHS, and JH6 for a for a particular variable heavy joining group for framework 4; VK 1, VK2, VK3, VK4, VK5 or VK6 for a particular VL kappa sequence for framework 1, 2, and 3, and JK1, JK2, JK3, JK4, or JK5 for a particular kappa joining group for framework 4; or VL1, VL2, VL3, VL4, VL5, VL6, VL7, VL8, VL9, or VL10 for a particular VL lambda sequence for framework 1, 2, and 3, and JL1, JL2, JL3, or JL7 for a particular lambda joining group for framework 4.

The general framework of the light chain comprises the structures selected from FR1-CDRL1-FR2-CDRL2-FR3-CDRL3-FR4 and FR1-CDRL1-FR2-CDRL2-FR3-CDRL3-FR4-CL, and variations thereof, wherein the framework regions are selected from either an immunoglobulin kappa light chain variable framework region, or an immunoglobulin lambda light chain variable framework region, and an immunoglobulin light chain constant region from either a kappa light chain constant region when the framework region is a kappa light chain variable framework region, or a lambda light chain constant region when the framework region is a lambda light chain variable framework region.

In one embodiment, the general framework of the heavy chain regions contemplated herein comprises the structures selected from FR1-CDRH1-FR2-CDRH2-FR3-CDRH3-FR4, FR1-CDRH1-FR2-CDRH2-FR3-CDRH3-FR4-CH1, FR1-CDRH1-FR2-CDRH2-FR3-CDRH3-FR4-CH1-Hinge-CH2 for IgG, IgD, and IgA immunoglobulin classes and FR1-CDRH1-FR2-CDRH2-FR3-CDRH3-FR4-CH1-CH2 for IgM and IgE immunoglobulin classes, FR1-CDRH1-FR2-CDRH2-FR3-CDRH3-FR4-CH1-Hinge-CH2-CH3 for IgG, IgD, and IgA immunoglobulin classes, FR1-CDRH1-FR2-CDRH2-FR3-CDRH3-FR4-CH1-CH2-CH3 for IgM and IgE immunoglobulin classes, and FR1-CDRH1-FR2-CDRH2-FR3-CDRH3-FR4-CH1-CH2-CH3-CH4 for IgM and IgE immunoglobulin classes, and variations thereof, wherein the framework regions are selected from heavy chain variable framework regions, and the heavy chain constant regions. IgA and IgM classes can further comprise a joining polypeptide that serves to link two monomer units of IgM or IgA together, respectively. In the case of IgM, the J chain-joined dimer is a nucleating unit for the IgM pentamer, and in the case of IgA it induces larger polymers.

The constant region domains of the antibody molecule for administration, if present, may be selected having regard to the proposed function of the antibody molecule, and in particular the effector functions which may be required. For example, the constant region domains may be human IgA, IgD, IgE, IgG or IgM domains. In particular embodiments, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

The antibody fragment administered may include Fab, Fab', F(ab')2, scFv, diabody, scFAb, dFv, single domain light chain antibodies, dsFv, a peptide comprising CDR, and the like.

In one embodiment, the human acceptor light chain framework is derived from an amino acid sequence encoded by a human IGKV (VL kappa) gene for framework 1, 2, and 3, and an IGKJ gene for framework 4. In one embodiment, the human acceptor light chain framework is derived from an amino acid sequence encoded by a human IGLV (VL lambda) gene for framework 1, 2, and 3, and an IGLJ gene for framework 4. Non-limiting examples of human light chain IGKV and IGKJ acceptor framework regions and non-limiting examples of human light chain IGLV and IGLJ acceptor framework regions are provide, for example, in WO2016/176656, incorporated herein by reference.

The immunoglobulin constant light chain region for use in the present invention is determined by the variable light chain the CDRs are grafted into. For example, if the variable light chain FR regions are derived from the immunoglobulin kappa light chain variable region, then a constant light chain region from an immunoglobulin kappa light chain constant region (IGKC) can be used to produce a light chain VL-CL chain. An IGKC that may be used in the present invention are provide, for example, in WO2016/176656, incorporated herein by reference. Conversely, when the framework region is immunoglobulin lambda light chain variable region, then an immunoglobulin lambda light chain constant region (IGLC) may be used to produce a lambda VL-CL light chain. An immunoglobulin lambda light chain constant region that may be used in the present invention are provide, for example, in WO2016/176656, incorporated herein by reference, and allelic variants thereof, which are generally known in the art, for example as identified in OMIM entry 147200 for IGKC variants and 147220 for IGLC variants.

In one embodiment, the human acceptor heavy chain framework is derived from an amino acid sequence encoded by a human IGHV gene for framework 1, 2, and 3, and an IGHJ gene for framework 4. Non-limiting examples of human heavy chain IGHV and IGHJ acceptor framework regions are provided, for example, in WO2016/176656, incorporated herein by reference.

The immunoglobulin heavy chain constant region for use in the present invention is determinant on the immunoglobulin class desired. All classes of immunoglobulins—IgG, IgD, IgA, IgM and IgE—are herein contemplated. For example, if the desired immunoglobulin is IgG, then the amino acid sequence encoding the IgG heavy chain constant region (IGGH) may be used.

Immunoglobulin heavy chain constant regions that may be used in the present invention include those of IGGH, IGDH, IGAH, IGMH, and IGEH described, for example, in WO2016/176656, incorporated by referenced, and allelic variants thereof, which are generally known in the art, for example as identified in OMIM entry 147100 for IGGH1 variants, 147110 for IGGH2 variants, 147120 for IGGH3 variants, 147130 for IGGH4 variants, 146900 for IGAH1 variants, 147000 for IGAH2 variants, 147180 for IGEH variants, 147020 for IGMH variants, 147170 for IGDH variants, all of which are incorporated herein by reference herein. In certain embodiment, the hinge region of a particular immunoglobulin class may be used in constructing the antibody contemplated herein. In one embodiment, the hinge region can be derived from a natural hinge region amino acid sequence as described in, for example, in WO2016/176656, incorporated herein by referenced, or a variant thereof. In one embodiment, the hinge region can be synthetically generated. Further contemplated herein are antibodies of immunoglobulin class IgA and IgM, which, in one embodiment, may be complexed with a joining polypeptide described in, for example, in WO2016/176656, incorporated herein by reference.

Methods of Treating Disorders Associated with CB1 Agonism

Methods are provided for neutralizing CB1 agonism by the 2-AG/aP2 complex (2-AG/aP2) within non-CNS peripheral tissues, for example, liver, kidney, and lung tissues. Because of the prominent role 2-AG/aP2 complex plays in inducing de novo lipogenesis by agonizing CB1, neutralizing, either fully or partially, CB1 agonism has the ability to modulate the severity of underlying conditions and disorders associated with CB1 stimulation. In one embodiment, a compound which interferes with the formation of the 2-AG/aP2 complex or the ability of the 2-AG/aP2 complex to agonize CB1 is administered to a subject having an underlying condition or disorder associated with excessive or dysregulated CB1 stimulation. In one embodiment, a monoclonal antibody as described herein is used to neutralize 2-AG/aP2's ability to agonize CB1.

In certain embodiments, methods are provided that preferentially target 2-AG/aP2 agonism of non-CNS peripheral, CB1 receptors. Peripheral CB1 receptors, as defined herein, are those CB1 receptors that are not localized to the brain or central nervous system (CNS). In contrast, the term global CB1 receptors refers to CB1 receptors anywhere in the body, including the brain and CNS.

In one embodiment, provided herein are method of treating a disorder in a subject mediated by 2-AG/aP2 agonism of CB1 by administering to the subject a compound that neutralizes the ability of 2-AG/aP2 from agonizing CB1. In one embodiment, the neutralization of CB1 agonism results in a reduction in hepatic de novo lipogenesis. In one embodiment, the neutralization of CB1 agonism results in a reduction in hepatic selective insulin resistance.

In one embodiment, the underlying condition or disorder associated with excessive or dysregulated CB1 stimulation is selected from obesity, diabetes, dyslipidemia, fibrosis, including liver and lung, non-alcoholic steatohepatitis (NASH), liver diseases, primary biliary cirrhosis, cardiovascular disease, cancer, pain, multiple sclerosis (MS) spasticity, glaucoma, inflammatory diseases, nephropathies, osteoporosis, metabolic disorders, psychiatric disorders, neurological disorders, neurodegenerative disorders, reproductive disorders, renal disease, kidney fibrosis, chronic kidney disease, atherosclerosis, cancer, and skin disorders, among others.

CB1 receptor signaling has been shown to exhibit detrimental activity in, for example, obesity, diabetes, fibrosis, liver diseases, cardiovascular disease, and cancer (Kunos et al., (2009), Trends Pharmacol. Sci. 30:1-7). In one aspect, the resultant neutralizers of 2-AG/aP2 are useful for reducing 2-AG/aP2 agonism of the CB1 receptor. Accordingly, in another aspect, the invention provides methods for treating disorders associated with CB1 agonism by administering to a subject in need of thereof a pharmaceutical composition comprising one or more compounds capable of interfering with 2-AG/aP2 agonism of CB1. In some embodiments, the compound capable of interfering with 2-AG/aP2 agonism of CB1 provides a beneficial effect when used for, or prevention of, obesity, diabetes, fibrosis, liver diseases, cardiovascular diseases, addictions such as nicotine addiction, or cancers.

Nonalcoholic steatohepatitis (NASH), also known as non-alcoholic fatty liver disease (NAFLD), refers to the accumulation of hepatic steatosis not due to excess alcohol consumption. NASH is a liver disease characterized by inflammation of the liver with concurrent fat accumulation. NASH is also frequently found in people with diabetes and obesity and is related to metabolic syndrome. NASH is the progressive form of the relatively benign non-alcoholic fatty liver disease, for it can slowly worsen causing fibrosis accumulation in the liver, which leads to cirrhosis (reviewed in Smith et al., (2011), Crit. Rev. Clin. Lab. Sci., 48(3):97-113). Currently, no approved therapies for NASH exist.

In one aspect, the compound capable of interfering with 2-AG/aP2 agonism of CB1 is used in the treatment, prevention, detection, or study of fibrosis. Several studies in mouse models have confirmed the role of CB1 receptor signaling in fibrosis, including liver fibrosis (Wei et al., (2014) Exp. Biol. Med. 239(2):183-192; Tam et al., (2010), J. Clin. Invest. 120(8):2953-2966; Wan et al., (2014), Cell Metabolism 19(6):900-901; Takano et al., (2014), Synapse, 68:89-97). Peripheral CB1 has been implicated in several mechanisms contributing to NASH and liver fibrosis, including steatosis (fatty liver), inflammation, and liver injury (Mallat et al., (2013) J. Hepatology, 59(4):891-896). CB1 has been demonstrated to be up-regulated in activated hepatic stellate cells (HSC), which mediate fibrosis by transitioning into myofibroblasts (Teixeira-Clerc et al., (2006) Nature Med. 12(6): 671-676). CB1 has also been implicated in diabetic nephropathy (Lin et al., (2014) J. Mol. Med. 92(7):779-792). CB1 has also been implicated in lung fibrosis (Cinar et al., Cannabinoid CB1 receptor overactivity contributes to the pathogenesis of idiopathic pulmonary fibrosis. JCI Insight, (2017) April 20;2(8) doi: 10.1172/j ci.insight.922810).

Studies in hepatocyte-specific and global CB1-knockout mice have implicated a major role of CB1 in peripheral cell type (hepatocytes) relevant to several metabolic diseases and disorders. In a mouse model of diet-induced obesity, both global CB1 knockout ($CB1^{-/-}$) and hepatocyte-specific CB1 knockout ($LCB1^{-/-}$) demonstrated reduced steatosis (fatty liver) and increased liver function, thus demonstrating a role of CB1 in peripheral cell types (hepatocytes) relevant to non-alcoholic steatohepatitis (NASH), diabetes, metabolic syndrome disease pathologies (Osei-Hyiaman et al., (2008) J. Clin. Invest. 118(9):3160-3169; Liu et al., (2012) Gastroenterology, 142:1218-1228). Selective knockdown of CB1 using a macrophage-specific CB1 knockdown siRNA (CB1R-GeRPs) prevents progressive hyperglycemia and decline in plasma insulin and C-peptide in Zucker diabetic fatty (ZDF) rats, which are a common model for T2D insulin resistance, hyperglycemia, and beta cell failure (Jourdan et al., (2013) Nature Med. 19(9):1132-1140). In a mouse model of alcohol-induced liver steatosis, both global CB1 knockout ($CB\ 1^{-/-}$) and hepatocyte-specific CB1 knockout ($LCB1^{-/-}$) have reduced steatosis and increased liver function, thus demonstrating a role for CB1 in peripheral cell types (hepatocytes) relevant to steatosis disease pathology (Jeong et al., (2008), Cell Metabolism 7:227-235). Lipid accumulation was shown to be reduced in epididymal white adipose cell lines generated from CB1 knockout mice relative to wild-type control (Wagner et al., (2011) Nutrition and Diabetes, 1:e16).

Studies in different models of disease in mouse have shown that peripherally-restricted CB1 receptor small molecule antagonists can effectively inhibit liver fibrosis progression (Wei et al., (2014) Exp. Biol. Med. 239(2):183-192; Tam et al., (2010), J. Clin. Invest. 120(8):2953-2966; Wan et al., (2014) Cell Metabolism 19(6):900-901; Takano et al., (2014) Synapse 68:89-97). Non-limiting examples of known CB1 antagonists include rimonabant, taranabant, VD60, Ionis-414930 antisense CB1, JD5037, AM6545, and TM38837. CB1 antagonists such as rimonabant have been shown to inhibit cell proliferation and down-regulate pro-fibrotic gene expression in primary human hepatic stellate cells (HSC), which mediate fibrosis by transitioning into myofibroblasts (Patsenker et al., (2011) Mol. Med. 17 (11-12):1285-1294). In the CC14-induced liver fibrosis mouse model, CB1 antagonist VD60 (3,4,22-3-demethoxycarbonyl-3-hydroxylmethyl-4-deacetyl-vindoline 3,4-thionocarbonate) was demonstrated to inhibit production of pro-fibrotic gene expression (alpha collagen) and proliferation in hepatic stellate cells (HSC line LX-2), while selective CB1 agonist ACEA (N-(2-chloroethyl)-5Z, 8Z, 11Z, 14Z-eicosatetraenamide) prevented this effect (Wei et al., (2014) Exp. Biol. Med. 239(2):183-192). CB1 antagonist JD5037 has been shown to reverse endocannabinoid-induced inhibition of insulin signaling (Cinar et al., (2014) Hepatology 59(1): 143-153). CB1 blockade using rimonabant reverses inflammation-induced impairment of glucose uptake in adipocytes isolated from high-fat diet rats (Miranville et al., (2010) Obesity 18:2247-2254).

Human studies also link peripheral CB1 receptors to disease etiology and progression. For example, up-regulation of CB1 in liver of NASH and HCV patients correlated with severity of liver steatosis and fibrosis (Auguet et al., (2014) BioMed Res. Intl. Vol. 2014, Article ID 502542). In addition, chronic CB1 agonism (via *cannabis* use) correlated with increased severity of liver steatosis and fibrosis in HCV patients (Van der Poorten et al., (2010) PlosOne 5, e12841). Furthermore, it has been shown that CB1 blockade in obese patients improves liver steatosis (Despres et al., (2009) ATVB 29:416-423).

It has also been recognized that the effect of CB1 antagonism differs depending on the location of the receptor. For instance, it is known that the effects of CB1 antagonism are tissue specific, as beneficial cardiometabolic effects of rimonabant observed in patients are independent of weight loss (Pi-Sunyeret et al., (2006) JACC 147:362A). Furthermore, it is known that rimonabant improves glycemic control in type 2 diabetes patients (Hollander et al., (2010) Diabetes Care 33(3):605-607) but that this effect is accompanied by significant psychiatric side effects imparted by CB1 receptors located in the CNS (Kunos et al., (2009) Trends Pharmacol. Sci. 30:1-7; Moreira et al., (2009) Rev. Bras. Psiquiatr. 31(2):145-153; Pacher et al., (2013) FEBS J. 280(9):1918-1943). The CB1 receptor antagonist rimonabant was shown to improve the profile of several metabolic risk factors (including adiponectin levels) in overweight patients according to the Rimonabant in Obesity (RIO-Lipids) study (Depres et al., (2005) NEJM 353:2121-2134).

In some embodiments, the compound capable of interfering with 2-AG/aP2 agonism of CB1 provides a beneficial effect when used as a treatment for, or for prevention of, pain, MS spasticity, or glaucoma. Multiple Sclerosis (MS) spasticity refers to feelings of stiffness and a wide range of involuntary muscle spasms (sustained muscle contractions or sudden movements). Spasticity is one of the more common symptoms of MS, and can vary in degree from mild tightness to painful, uncontrollable spasms of extremities. Left untreated, spasticity can lead to serious complications, including contractures (frozen or immobilized joints) and pressure sores. Current treatment options for MS spasticity include baclofen, tizandine, diazepam, Dantrolene, phenol, among others. CB1 receptors have been shown to mediate control of spasticity in a mouse model of MS (Pryce et al., (2007), Br. J. Pharmacol. 150(4):519-525).

Activation of CB1 receptors produces analgesic effects in several experimental pain models, including visceral pain arising from the gastrointestinal tract. CB1 agonists such as WIN55, 212-2, and SAB-378 have also been shown to inhibit pain-related responses to repetitive noxious stimuli (Brusberg et al., (2009) J. Neuroscience 29(5):1554-1564; Talwar et al., (2011) CNS Neurol. Disord. Drug Targets 10(5):536-544).

One skilled in the art would be able, by routine experimentation, to determine what an effective, non-toxic amount of therapeutic agent would be for the purpose of treating a CB1 associated disease or disorder. For example, a therapeutically active amount of a neutralizing compound may vary according to factors such as disease stage (e.g., stage 1 versus stage IV), age, sex, medical complications (e.g., immunosuppressed conditions or diseases) and weight of the subject, and the ability of the neutralizing compound to elicit a desired response in the subject. The dosage regimen may be adjusted to provide the optimum therapeutic response. For example, several divided doses may be administered daily, or the dose may be proportionally reduced as indicated by the exigencies of the therapeutic situation.

The neutralizing compounds discovered with the disclosed methods of identification described herein can be administered in combination with any desired therapeutic agent, including other agents that bind directly to the CB1 receptor.

In one embodiment, a monoclonal antibody as described herein is used to neutralize 2-AG/aP2's ability to agonize CB1.

Combination Therapies

A compound capable of interfering with 2-AG/aP2 agonism of CB1 can be used to treat an underlying disorder mediated through excessive CB1 agonism. In one embodiment, the compound is administered to a subject in need thereof in combination or alternation with an additional active ingredient.

In some embodiments, provided herein are methods utilizing combination therapy wherein a compound capable of interfering with 2-AG/aP2 agonism of CB1 are administered to a subject with another therapeutic agent. Examples of additional therapeutic agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, 0C29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL- 73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH2) exenatide/Exendin-4, Exenatide LAR, Linaglutide, AVE0010, CJC 1131, BIM51077, CS 872, THCB18, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 125I , T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]-isothiazole-3-ol 1-oxide, 5-(4-((3-(2,6-dimethyl-4-(3-(methyl sulfonyl)propoxy)-phenyl)phenyl)-methoxy)phenyl)i so, 5-(4-((3-(2-methyl-6-(3-hydroxypropoxyl)pyridine-3-yl)-2-methylphenyl) methoxy)phenyl)isothiazol e-3-ol 1-oxide, and 5-[4-[ [3-[4-(3-aminopropoxy)-2,6-dimethylphenyl]phenyl]methoxy] phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211;

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, 58921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPAR agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-Al Milano/ETC216 (Pfizer), ETC-642 (Pfizer), ISIS301012, D4F (Bruin Pharma), synthetic trimeric ApoA1, Bioral Apo Al targeted to foam cells, and the like; (29) IBAT inhibitors such as BARI143/HMR145A/HMR1453 (Sanofi-Aventis, PHA384640E (Pfizer), 58921 (Shionogi) AZD7806 (AstraZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCO1VIPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (*Vernalis*), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithKline), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, MO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, 52367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (*Vernalis*/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) f33 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone f3 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahy dro-5,5, 8,8-tetram ethyl-2-napthal enyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11f3 HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4, 5,6,7,8,9,10, 11,12,3 a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/1(364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512, 565, 5,391,571, 5,602,151, 4,405,644, 4,189,438, and 4,242, 453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Technologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mclr (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55)C-terminal growth hormone fragments such as A0D9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof;

(f) CB1 (cannabinoid-1 receptor) antagonist/inverse agonists such as rimonabant (Acomplia; Sanofi), SR-147778 (Sanofi), SR-141 716 (Sanofi), BAY 65-2520 (Bayer), and SLV 319 (Solvay), and those disclosed in patent publications U.S. Pat. Nos. 4,973,587, 5,013,837, 5,081,122, 5,112,820, 5,292,736, 5,532,237, 5,624,941, 6,028,084, 6,509,367, 6,509,367, WO96/33159, WO97/29079, WO98/31227, WO98/33765, WO98/37061, WO98/41519, WO98/43635, WO98/43636, WO99/02499, WO00/10967, WO00/10968, WO01/09120, WO01/58869, WO01/64632, WO01/64633, WO01/64634, WO01/70700, WO01/96330, WO02/076949, WO03/006007, WO03/007887, WO03/020217, WO03/026647, WO03/026648, WO03/027069, WO03/027076, WO03/0271 14, WO03/037332, WO03/040107, WO03/086940, WO03/084943 and EP658546;

(g) CB1 receptor antagonists such as 1,5-diarylpyrazole analogues such as rimonabant (SR141716, Acomplia®, Bethin®, Monaslim®, Remonabent®, Riobant®, Slimona®, Rimoslim®, Zimulti® and Riomont®), surinabant (SR147778) and AM251; 3,4-diarylpyrazolines such as SLV-319 (ibipinabant); 4,5-diarylimidazoles; 1,5-diarylpyrrole-3-carboxamides, bicyclic derivatives of diaryl-pyrazole and imidazoles such as CP-945,598 (otenabant); methylsulfonamide azetidine derivatives; TM38837; beta-lactam cannabinoid modulators; benzofuran derivatives. CB1 receptor antagonists can include or exclude 1,5-diarylpyrazole analogues such as rimonabant (SR141716, Acomplia®, Bethin®, Monaslim®, Remonabent®, Riobant®, Slimona®, Rimoslim®, Zimulti® and Riomont®), surinabant (SR147778) and AM251; 3,4-diarylpyrazolines such as SLV-319 (ibipinabant); 4,5-diarylimidazoles; 1,5-diarylpyrrole-3-carboxamides, bicyclic derivatives of diaryl-pyrazole and imidazoles such as CP-945,598 (otenabant); methylsulfonamide azetidine derivatives; TM38837; beta-lactam cannabinoid modulators; and benzofuran derivatives Pharmaceutical Compositions A compound, for example, a small molecule, ligand, antibody, antigen-binding agent, or antibody-binding fragment that inhibits the 2-AG/aP2 complex from agonizing CB1 useful in the treatment and/or prophylaxis of a pathological condition can be administered in an effective amount as a pharmaceutical composition comprising the compound in combination with one or more of a pharmaceutically acceptable excipient, diluent, or carrier. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The compound disrupting the 2-AG/aP2 complex agonism of CB1 may be the sole active ingredient in the pharmaceutical composition or may be accompanied by other active ingredients including other ingredients.

The pharmaceutical compositions suitably comprise a therapeutically effective amount of the compound that interrupts 2-AG/aP2 complex agonism of CB1. The term "therapeutically effective amount" as used herein refers to an amount of a therapeutic agent needed to inhibit 2-AG/aP2 complex agonism of CB1 in such a way so as to treat, ameliorate, or prevent a targeted disease or condition, or to exhibit a detectable therapeutic or preventative effect mediated by CB1.

For any suitable compound, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. As a non-limiting example, treatment of CB-1 mediated pathologies in humans or animals can be provided as a daily dosage of anti-2-AG/aP2 monoclonal antibodies of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof.

The pharmaceutical composition may also include a molar ratio of the active compound and an additional active agent. For example, the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof. Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6): 318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung. dose forms containing a predetermined amount of an active agent of the invention per dose.

Advantageously, the levels of 2-AG/aP2 agonism of CB1 in vivo may be maintained at an appropriately reduced level by administration of sequential doses of a compound that interferes with the 2-AG/aP2 agonism of CB1 according to the disclosure.

Compositions may be administered individually to a patient or may be administered in combination (e.g. simultaneously, sequentially, or separately) with other agents, drugs or hormones.

In one embodiment, compound is administered continuously, for example, the compound can be administered with a needleless hypodermic injection device, such as the devices disclosed in, e.g., U.S. Pat. Nos. 5,399,163, 5,383,851, 5,312,335, 5,064,413, 4,941,880, 4,790,824, or 4,596,556. Examples of implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

EXAMPLES

Example 1

Animals

Wild-type C57BL/6J mice, B6.129-Tg(Adipoq-cre/Esr1*)1Evdr/J, and ApoE$^{-/-}$ mice were purchased from Jackson Laboratories. Mice were maintained on a 12-hour light/dark cycle, with ad lib access to food. Mice were maintained on regular chow diet (RD; PicoLab 5058 LabDiet). High-fat diet (HFD) (60% kcal fat; Research Diets Inc., D12492i) and western diet (1.5% cholesterol); Research Diets Inc., D12079Bi) was used for HFD studies and ApoE$^{-/-}$ mice studies. All experimental procedures involving animals were approved by the Harvard T.H. Chan School of Public Health (HSPH) institutional Animal Care and Use Committee.

Example 2

Generation of humanized aP2-floxed mice

Because human and mouse aP2 protein are highly similar with only 11 amino acid differences in exon 2 and 3, an aP2 fragment containing exon 1 to 4 with point mutations in exon 2 and 3 to humanize the protein was used to construct a targeting vector. The scheme for construction of the targeting vector is shown in FIG. 1E. The targeting construct was introduced into ES cells by electroporation, and G418-resistant clones were examined for homologous recombination using Southern blot. Two ES clones that contained the correctly targeted FABP4 locus were injected into C57BL/6J blastocysts to obtain chimeric mice. Male chimeras were bred with C57BL/6J female transgenic mice expressing the enhanced site-specific recombinase FLP to remove the FRT-flanked neomycin cassette to generate heterozygous floxed humanized FABP4$^{fl/+}$ mice. After generating the homozygous floxed humanized FABP4$^{fl/fl}$ mice, these mice were crossed with hemizygous transgenic mice expressing tamoxifen-inducible Cre recombinase under Adiponectin promoter (Adipoq-CreER) (FABP4$^{adip-/-}$). FABP4$^{adip-/-}$) mice were crossed with ApoE$^{-/-}$ mice to generate ApoE$^{-/-}$ FABP4$^{f/f}$ and ApoE$^{-/-}$FABP4$^{adip-/-}$ mice. Deletion of adipocyte aP2 was induced by intraperitoneal injection of 50 mg/kg tamoxifen solubilized in corn oil at 10 mg/ml daily for 6 days. For the analysis of lean FABP4$^{fl/fl}$ and FABP4$^{adip-/-}$ mice, deletion of adipocyte aP2 was induced at the age of 7-9 weeks and phenotype analysis was performed in 12-16 weeks old mice. For the analysis of effect of adipose tissue specific deletion of aP2 in obese mice, deletion of adipocyte aP2 was induced in mice fed HFD for 12 weeks beginning 6-8 weeks old. The analysis of the phenotype of FABP4$^{fl/fl}$ and FABP4$^{adip-/-}$ fed HFD was performed at 4 weeks after the tamoxifen administration. For the analysis of effect of adipose tissue specific deletion of aP2 in ApoE$^{-/-}$ mice, tamoxifen administration was started at 6-7 weeks old at the same time of starting western diet feeding.

Example 3

Metabolic Studies

For insulin tolerance tests (ITTs), mice were fasted for 6 h, after which blood glucose concentrations were assessed before intraperitoneal injection of 1U/kg of insulin (Eli Lilly Humulin) in 0.2% w/v BSA in PBS into C57BL/6 mice fed HFD, and then 15,30, 60, 90 and 120 min after injection. At each time point, a 5 μl blood sample was collected via a tail nick, and glucose was assessed using an automatic blood glucose meter. For intra peritoneal glucose tolerance tests (ipGTTs), mice were fasted for 16 h, after which blood glucose concentrations were assayed before intra peritoneal administration of 1 g/kg glucose. Glucose levels were then assessed 15, 30, 60, 90 and 120 min after the glucose administration.

Example 4

Hepatic de novo lipogenesis (DNL) and very low-density lipoprotein (VLDL) production For quantification of hepatic DNL, 150 μCi$^3$H2O was intraperitoneally injected. The mice were sacrificed 1 hour after the injection and 4 pieces of liver were collected (~100m each). The liver pieces were lysed with 200 μl PBS and total lipids were extracted utilizing the Dole's extraction method (Dole et al., (1960) J. Biol. Chem. 235, 2595-2599) and $^3$H incorporation into de novo synthesized lipids were analyzed by scintillation count and calculated relative to tissue weight. VLDL production was determined by measuring plasma triglyceride (TG) levels after various time points after tail vein injection of Triton WR-1339 (Tyloxapol from Sigma; 0.5 mg per g body weight as 10% wt./vol. solution in PBS).

Example 5

Lipoprotein Clearance Analysis

For turnover studies, mice were tail vein—injected with 200p1 radiolabeled triglyceride rich lipoproteins (TRLs), which were prepared as described previously (Bartelt, NatMed2011). Lipoprotein turnover was determined from scintillation count of 10 μl plasma 2, 5, 10 and 20 min after injection.

Example 6

Cold Tolerance Test

For cold tolerance test mice were fasted for 18 hrs and then transferred to a cold room, maintained at 4° C. and housed in single cages. Core body temperature was determined by rectal-probe measurement every hour, and mice with body temperature of less than 30° C. were excluded during the experiment.

Example 7

3T3L1 adipocyte and Adipose tissue explants for HepG2 cells treatment

Murine 3T3L1 adipocytes and human HepG2 cells were obtained from the ATCC. 3T3L1 adipocytes were maintained in Dulbecco Modified Eagle Medium (DMEM) containing 25 mM glucose (Gibco) supplemented with 10% cosmic calf serum (CCS), and adipocyte differentiation was induced as previously described (Ntambi et al., (1988) J. Biol. Chem. 263, 17291-17300). Briefly, preadipocytes were grown in 10 cm dishes until they are fully confluent. At confluent state, 10% bovine calf serum (BCS) containing DMEM medium was replaced with 10% fetal bovine serum (FBS) containing DMEM for two days. Differentiation was induced by FBS medium containing 5 μg/ml Insulin (Sigma, 15500), 0.5 mM IBMX (Sigma, 15879), 1 μM Dexamethasone (Sigma, D4902), and 1 μM Rosiglitazone (Cayman Chemical, 71740). After two days, medium was replaced with FBS medium containing 5 μg/ml Insulin every other day until the cells were completely differentiated at day 10. For siRNA experiment, differentiated 3T3-L1 adipocytes were transfected using Amaxa Nucleofector Kit L (Lonza, VCA-1005) according to the manufacturer's protocol. Briefly, differentiated adipocytes were trypsinized and centrifuged at 100 g for 10 minutes. 3×106 cells per 6-well were transfected with 120 pmol/sample Control siRNA (Dharmacon, D-001810-10) or mouse aP2 siRNA (Dharmacon, L-042923-01) using Nucleofector Program A-33. Transfected cells were seeded in Collagen I coated 6-well plates (Corning, 356400). Conditioned media for stimulation of HepG2 cells were prepared in DMDM 3.3 mM glucose supplemented with 0.5% FBS before (basal) and after (lipolysis stimulated) the lipolysis stimulation with 1 mM IBMX. For explant studies, adipose tissue was removed from 8-12 weeks-old littermate mice, minced and washed 5× with DMEM high glucose supplemented with 10% CCS. Twenty pieces of adipose tissue were placed into 6-well plates in 2 ml DMEM high glucose with 10% CCS and incubated for 1 hr. Then conditioned media for stimulation of HepG2 cells were prepared in 3'-demethoxy-30-demethylmatairesinol (DMDM) 3.3 mM glucose supplemented with 0.5% FBS before (basal) and after (lipolysis stimulated) the lipolysis stimulation with 1 mM 3-isobutyl-1-methylxanthine (IBMX). For antibody neutralization, 10 nM (for 3T3L1 cells) or 20 nM (for adipose tissue explant) of IgG, CA33, or CA15 antibody was added to DMDM 3.3 mM glucose supplemented with 0.5% FBS was used for the preparation of "basal" and "lipolysis stimulated" conditioned media.

For maintenance, HepG2 cells were cultured in DMEM containing 5.5 mM glucose (Gibco) supplemented with 10% FBS. For DNL and p-AMPK analysis, HepG2 cells were cultured in DMDM 3.3 mM glucose supplemented with 0.5% FBS, seeded 2×105 cells in 12 well plate or 4×105 cells in 6 well plate for DNL analysis and p-AMPK analysis, respectively.

For DNL analysis, after overnight culture, the cells were stimulated with conditioned media or 2-AG/aP2 complex and 40Ci of $^3$H2O were added 30 min after the stimulation (Gnoni et al., (1985) Biochem. & Biophysical Res. Comm. 128, 525-530; Lowenstein et al., Meth. Enzym. 35, 279-287). After 2 hours of incubation with $^3$H2O, cells were washed with PBS and lysed with 0.1N NaOH. The cell lysate was analyzed for protein concentration and total lipid was extracted by Dole's extraction method (Dole et al., (1960) J. Biol. Chem. 235, 2595-2599). $^3$H incorporation into de novo synthesized lipids were analyzed by scintillation count and calculated as count per μg protein. For p-AMPK analysis, after overnight culture, cells were stimulated with conditioned media or 2-AG/aP2 complex for 30 min. The cells were washed twice with ice cold PBS and lysed with ice cold RIPA buffer (Cell Signaling) supplemented with 1 mM PMSF. AMPK phosphorylation was determined by western blot (see below).

Example 8

Recombinant mouse FABP4 expression and purification

Mouse FABP4 cloned into the Pet28a plasmid was used to overexpress the protein in *Escherichia coli* strain $BL21_{DE3}$ (Burak et al., (2015) Sci. Trans. Med. 7, 319ra205). 10 ml of LB medium containing 30 mg/L kanamycin was inoculated with the transformant. The cells were grown overnight at 37° C. The activated culture was transferred into 1 L LB medium containing 30 mg/L kanamycin. The cells were grown until $OD_{600}$ reached 0.6-0.8. The culture was induced with isopropyl β-D-1-thiogalactopyranoside (IPTG) at a final concentration of 1 mM. After induction, the culture was incubated 4 hours at 37° C. The cell paste was harvested and stored at −80° C. The pelleted cells were resuspended in lysis buffer containing 20 mM Tris pH 7.5, 500 mM NaCl, 20 mM Imidazole and a Complete EDTA-free protease inhibitor cocktail (Roche) and lysed by sonication. Cell debris was removed by centrifugation (15,000 rpm for 30 min at 4° C., Beckman Coulter JA-17 rotor). The supernatant was applied to the equilibrated HisTrap FF crude (1 ml) purification column (GE Healthcare) at 1 ml/min flow rate by using peristaltic pump. The column was washed with the 10-15 ml of the lysis buffer and the bound proteins were eluted with the 10 ml of the buffer contains 20 mM Tris pH 7.5, 500 mM NaCl, 500 mM Imidazole. Eluted FABP4 protein was concentrated to 1 ml and desalted with the buffer containing 20 mM Tris pH 7.5, 50 mM NaCl, 0.5 mM EDTA, 1 mM TCEP using Amicon Centrifugal Filter Units (10,000 kDa NMWL, EMD Millipore). The His tag of the protein was cleaved off by overnight incubation of the protein with MBP tagged TEV protease at 4° C. (1 mg TEV per 100 mg his-tagged protein). The overnight digested protein was centrifuged at 14,000 rpm using microcentrifuge for 10 minutes. For further purification, the sample was applied to a size exclusion column (HiLoad 16/600 Superdex 75 pg) at 0.5 ml/min flow rate by BioLogic DuoFlow 10 system, pre-equilibrated with 20 mM Tris pH 7.5, 150 mM NaCl, 1 mM TCEP at 4° C. The collected fractions containing FABP4 were eluted and combined and then concentrated to 10 mg/ml using Amicon Centrifugal Filter Units (10,000 kDa NMWL, EMD Millipore).

Example 9

Preparation of 2-AG/aP2 complex 10 or 20 μM delipidated mouse recombinant aP2 protein with or without 10 μM 2-AG were diluted in 50 mM potassium phosphate buffer (pH 7.4) and incubated at 37C for overnight. The ratio of aP2 binding to 2-AG was determined by 8-Anilinonaphthalene-1-sulfonic acid (ANS) assay. For antibody neutralization, IgG, CA33, or CA15 antibody at final concentration of 20 μM was added to 50 mM potassium phosphate buffer (pH 7.4) only or to delipidated mouse recombinant aP2 protein (final 10 μM) with 2-AG (final 10 μM) solution in 50 mM potassium phosphate buffer (pH 7.4) and incubated at 37° C. overnight. Final concentration in culture media for aP2, 2-AG, and antibodies were 10, 10, and 20 nM, respectively.

Example 10

8-Anilinonaphthalene-1-sulfonic acid (ANS) binding assay aP2 or aP2/lipid solution (final aP2 concentration 1 μM) and ANS (final 5 μM) was diluted in 50 mM potassium phosphate buffer (pH 7.4) and fluorescence Ex/Em 375/475 was measured.

Example 11

2-AG/aP2 co-crystallization, and data collection

20 μl of 2-AG in acetonitrile (20 mM, Cayman Chemical) was transferred into 1.5 ml centrifuge tube and the acetonitrile was evaporated by using vacuum concentrator for 20 minutes at 30° C. The dried 2-AG was resuspended in 15 μl of pure ethanol and diluted to 1 ml with incubation buffer containing 20 mM Tris pH 7.5, 150 mM NaCl, 1 mM TCEP. The resultant solution was — 400 μM. The aP2 was mixed with 2-AG in the incubation buffer at 1:4 molar ratio. The protein and the fatty acid mixture was incubated overnight at 37° C. After the incubation, the sample was concentrated to 10 mg/ml aP2 using protein concentrator (3000 MWCO, Vivaspin 500, Sartorius). The concentrated samples were screened by using the JCSG Core Suites I-IV and the PEGs Suite (Qiagen). The initial crystal hit was observed in 0.2M LiSO4 and 20% PEG 3350. To get a larger diffracting crystal, a grid screen was prepared at various LiSO4 and PEG 3350 concentrations and pH 7.5. The final crystal was found at 0.1 M Tris pH 7.5, 0.2 M LiSO4 and 30% PEG3350.

Home source x-ray radiation (Rigaku Micromax 007 x-ray generator) was used to collect diffraction data for the crystals after flash-vitrification at 100 K in a cryo stream (X-Stream 2000). The complex crystal was cryoprotected with ethylene glycol (20% ethylene glycol). Diffraction data were collected in home lab using a R-Axis HTC detector. 180 1° oscillation images were recorded at 150 mm crystal-to-detector distance, corresponding to 2.0 A resolution (Table 5). Indexing, integration and scaling of all diffraction images were performed in HKL-2000 (Otwinowski & Minor, 1997). The structure of 2-AG/aP2 crystal was solved by molecular replacement using protein coordinates from a high-resolution model of mouse aP2 (PDB ID: 3HK1). Molrep-AutoMR in CCP4 suite was used to find a solution for phasing. The model was adjusted manually using COOT. Stereochemically restrained refinement of the models was carried out in REFMACS using maximum-likelihood targets (Table 5). The restraints for the 2-AG molecules were calculated by using ProDRG in CCP4 suite. Water molecules were located and verified manually by using COOT. The stereochemical quality of the models was assessed with PROCHECK. Molecular and electron density illustrations were prepared in UCSF Chimera.

TABLE 5

Data collection and structure refinement statistics.

| | |
|---|---|
| Data Collection | |
| Space Group | C 2 2 21 |
| Unit Cell Parameter | |
| a (Å) | 78.990 |
| b (Å) | 95.090 |
| c (Å) | 49.740 |
| Beam Source | Rotating Cu-Anode |
| Wavelength (Å) | 1.54 |
| Temperature (K) | 100 |
| Number of protein molecules in asymmetric unit | 1 |
| Resolution (Å) | 1.99 |
| Number of observations | |
| Number of unique reflections | |
| Completeness (%) | 99.63 |
| Rmerge[a] | |
| Rpim[b] | |
| ⟨I/σ (I)⟩ | |
| Refinement Statistics | |
| Program Used | REFMAC |
| Resolution limits (Å) | 60.76-1.99 |
| Number of reflections | 12475 |
| Number of reflections in test set | 659 |
| Number of atoms | 1207 |
| Water molecules | |
| R/Rfree | 0.19/0.24 |
| Overall B-value (Å2) | 38.5 |
| RMSD from ideal | |
| Bond lengths (Å) | 0.017 |
| Bond angles (°) | 1.674 |
| Ramachandran φ/ϕ angles (%) | |
| Most favored | 93.3 |
| Additionally allowed | 6.7 |
| Generously allowed | 0.0 |
| PDB codes | XXXX |

Values in parentheses correspond to the last resolution shell.

[a]$R_{merge} = \Sigma_{hkl} \Sigma_i | I_i(hkl) -$ ? I(hkl) ? $|/\Sigma_{hkl}\Sigma_i I_i(hkl)$, where $I_i(hkl)$ is the ith observation of reflection hkl, and ⟨I(hkl)⟩ is the weighted average intensity for all observations i of reflection hkl.

[b]$R_{pim} = \Sigma_{hkl}[1/(N-1)]^{1/2}\Sigma_i|I_{i(hkl)} - \langle I_{(hkl)} \rangle|/\Sigma_{hkl}\Sigma_i I_{i(hkl)}$, where N is redundancy[71], calculated in SCALA[72] using data processed with DENZO[73].

Example 12

Western Blotting

The antibodies used were rabbit anti-pAMPK (Cell Signaling), anti-actin HRP conjugated (Abcam), in-house anti-aP2 (H3) HRP conjugated antibodies. For quantification, Western blot images were captured and band intensities were analyzed using ImageJ software.

Example 13

Lipid Analysis

Triglyceride (TG) levels were analyzed using triglyceride assay kit (Randox) and Cholesterol levels were analyzed using by Infinity cholesterol kid (Thermo Scientific). FFA levels in culture media were measured using a NEFA-HR2 kit (Wako) following the manufacturer's instructions.

Example 14

Statistical Analysis

Data are shown as means±SEM. Differences in body weight changes were analyzed using two-way ANOVA. Differences between two groups were analyzed using Student's t test. Comparisons among multiple groups were made using one-way ANOVA followed by a post hoc Tukey-Kramer test for multiple groups. Values of $P<0.05$ were considered significant.

Example 15

Adipocyte Lipolysis Accelerates Hepatic De Novo Lipogenesis (DNL) Through aP2 Secretion Both In Vitro and In Vivo.

Figure 5A:
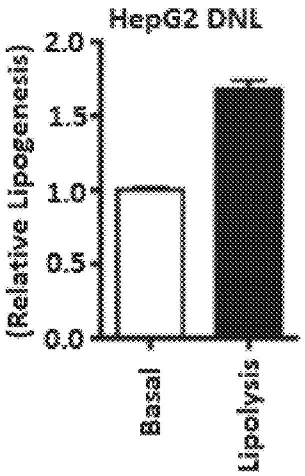
FIG. 5A is a bar graph that shows DNL in HepG2 cells treated with conditioned media from 3T3L1 adipocytes before (Basal) and after (Lipolysis) 1 μM IBMX stimulation. DNL was measured by scintillation count, normalized to protein concentration and expressed relative to the basal condition. n=4 in each condition. Error bars are standard error of the mean. The x-axis shows the treatment group, and the y-axis is relative lipogenesis.

To directly address the possibility that adipose tissue lipolysis contributes to increased hepatic DNL in obesity, lipolysis was stimulated in adipocytes and the effect of the resultant conditioned media was tested on HepG2 cells. Following induction of lipolysis by IBMX, conditioned media from either 3T3L1 adipocytes or white adipose tissue (WAT) explants promoted lipogenesis in HepG2 cells as measured by $^{3}H2O$ incorporation into free fatty acids and non-polar acylglycerols (see FIGS. 1A and 5A).

Figure 5B:
FIG. 5B shows aP2 levels that were measured by western blot.
Figure 5C:
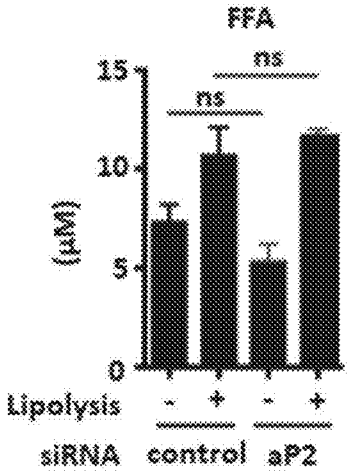
FIG. 5C is a bar graph that shows FFA release from 3T3L1 adipocytes transfected with siRNA against control or aP2. n=3 in each condition. Error bars are standard error of the mean. The x-axis is the treatment group, and the y-axis is micromolar FFA concentration.

It was recently reported that adipocyte fatty acid binding protein aP2 also functions as an adipokine and is secreted in response to lipolysis stimuli in a regulated manner (Cao et al., (2013) Cell Metab. 17, 768-778; Ertunc et al., (2015) J. Lipid Res. 56, 423-434). To examine the potential role of aP2 in driving hepatic DNL, differentiated 3T3L1 adipocytes were first transfected with siRNA against aP2 or a control siRNA (see FIG. 5B). Although there was no difference in the level of lipolysis in these cells (see FIG. 5C), suppression of aP2 abrogated the induction of aP2 secretion (see FIG. 1B) and blocked the ability of the adipocyte conditioned medium to induce DNL in liver cells (see FIG. 1C). Activation of the kinase AMPK, which occurs under conditions of low cellular energy, is associated with inhibition of pathways including DNL, while de-phosphorylation of AMPK relieves this inhibition. In agreement with this model, it was found that treatment with conditioned media from lipolysis-stimulated 3T3L1 adipocytes and adipose tissue explants suppressed phosphorylation of AMPK (Thr172) in HepG2 cells and this effect was also abrogated by genetic suppression of aP2 in adipocytes (see FIG. 1D).

Figure 1H:
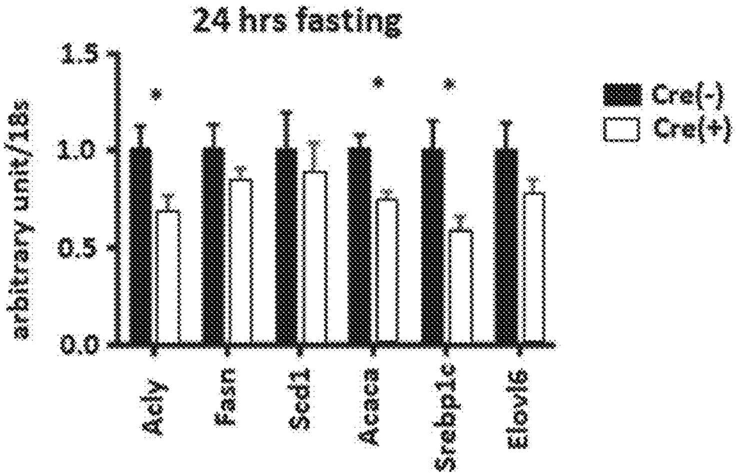
FIG. 1H is a bar graph that shows mRNA levels of lipogenic genes normalized to 18s rRNA and expressed relative to control. n=10 and 11 mice for FABP4$^{f/f}$ and FABP4$^{adip-/-}$ mice, respectively. Error bars are standard error of the mean.
Figure 1I:
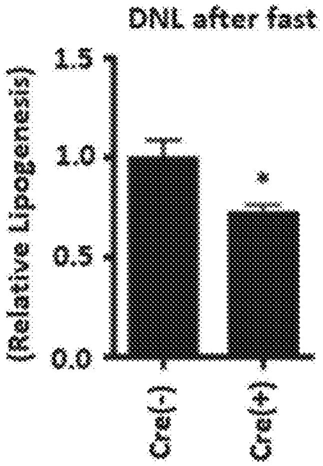
FIG. 1I is a bar graph that shows hepatic DNL of FABP4$^{f/f}$ and FABP4$^{adip-/-}$ mice fasted for 22 hours. DNL was analyzed by scintillation count, normalized to tissue weight (mg) and expressed relative to the level in control mice. n=11 and 10 for FABP4$^{f/f}$ and FABP4$^{adip-/-}$ mice, respectively. Error bars are standard error of the mean. The x-axis is the treatment group, and the y-axis is relative lipogenesis.
Figure 1J:
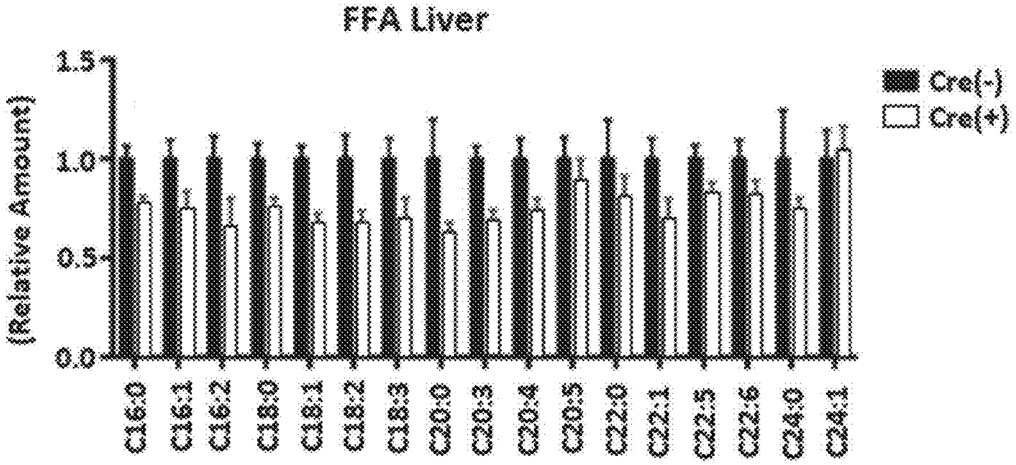
FIG. 1J is a bar graph that shows levels of FFA species in liver of FABP4$^{f/f}$ and FABP4$^{adip-/-}$ mice fasted for 22 hours. n=5 for each genotype. Error bars are standard error of the mean. The x-axis is the FFA species, and the y-axis is relative level.
Figure 5D:
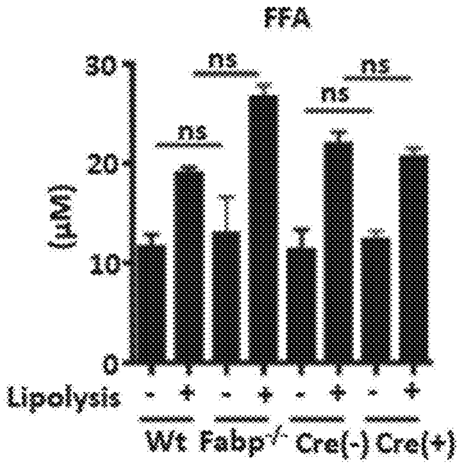
FIG. 5D is a bar graph that shows FFA release from adipose tissue explant from each genotype. n=3 in each condition. Error bars are standard error of the mean. The x-axis is the treatment group, and the y-axis is micromolar FFA concentration.
Figure 5E:
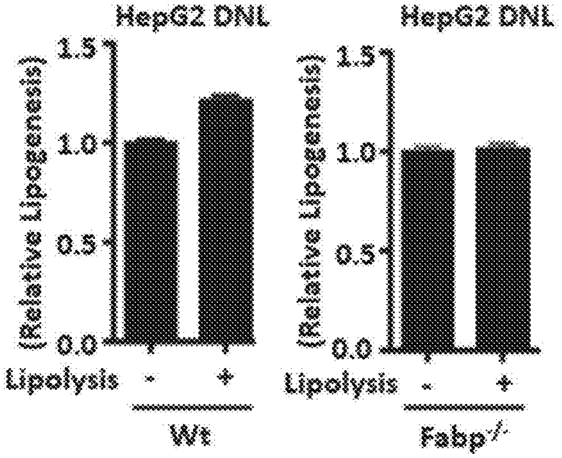
FIG. 5E are bar graphs that show DNL in HepG2 cells treated with conditioned media from adipose tissue explant of each genotype before (Basal) and after (Stimulation) 1 μM IBMX stimulation. DNL was measured by scintillation count, normalized to protein concentration and expressed relative to the basal condition. n=4 in each condition. Error bars are standard error of the mean. The x-axis is the treatment group, and the y-axis is relative lipogenesis.
Figure 5F:
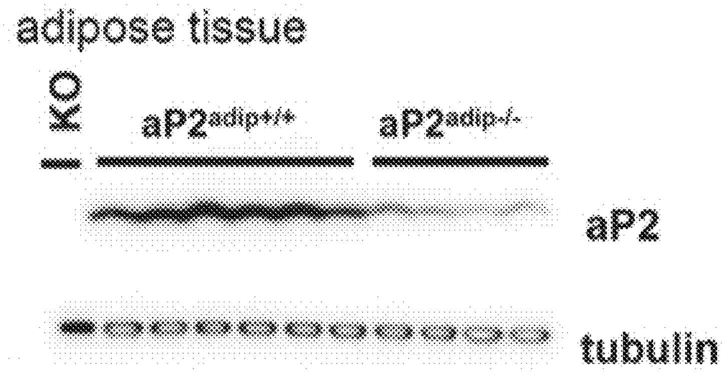
FIG. 5F shows aP2 levels in adipose tissue that were measured by western blot.
Figure 5G:
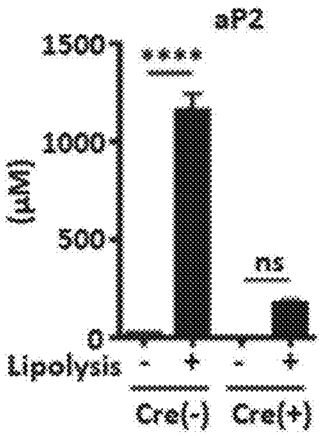
FIG. 5G is a bar graph that shows aP2 secretion from adipose tissue explant of $FABP4^{f/f}$ and $FABP4^{adip-/-}$ mice. n=3 in each condition. Error bars are standard error of the mean. The x-axis is treatment group, and the y-axis is micromolar aP2 concentration.
Figure 5H:
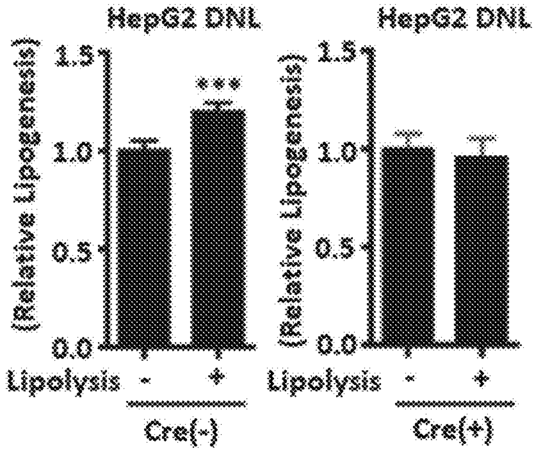
FIG. 5H are bar graphs that show DNL in HepG2 cells treated with conditioned media from adipose tissue explant of each genotype before (Basal) and after (Stimulation) 1 μM IBMX stimulation. DNL was measured by scintillation count, normalized to protein concentration and expressed relative to the basal condition. n=4 in each condition. Error bars are standard error of the mean. The x-axis is the treatment group, and the y-axis is relative lipogenesis.
Figure 5I:
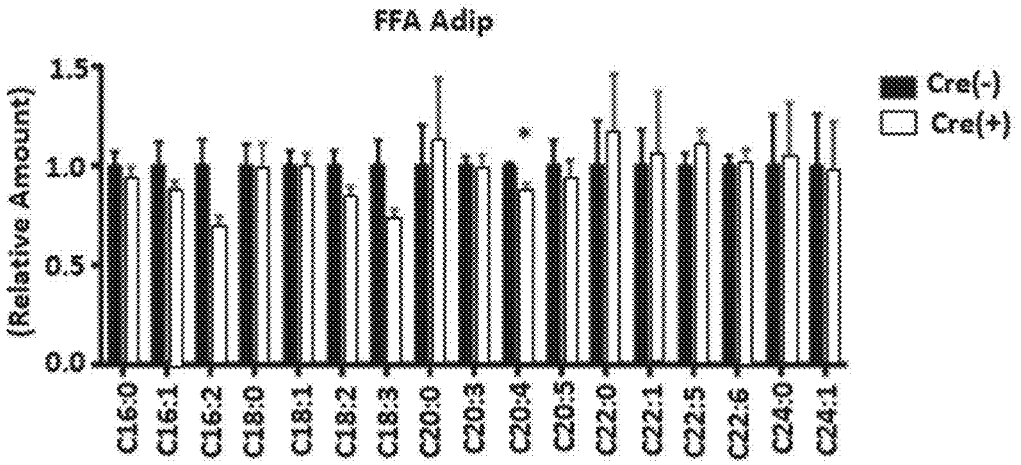
FIG. 5I is a bar graph that shows the levels of FFA species in adipose tissue of $FABP4^{f/f}$ and $FABP4^{adip-/-}$ mice fasted for 22 hours. n=5 for each genotype. Error bars are standard error of the mean. The x-axis is FFA type, and the y-axis is relative amount.
Figure 5J:
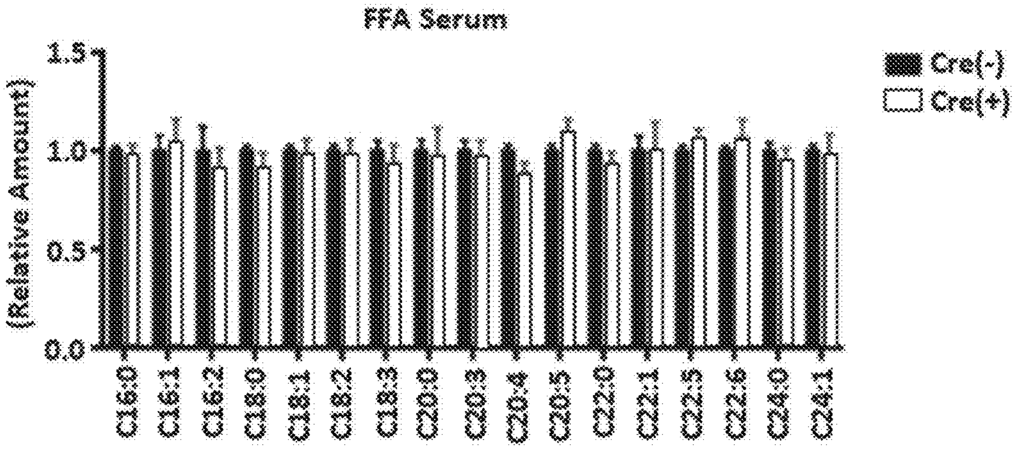
FIG. 5J is a bar graph that shows the levels of FFA species in serum from $FABP4^{f/f}$ and $FABP4^{adip-/-}$ mice fasted for 22 hours. n=4 and 5 for $FABP4^{f/f}$ and $FABP4^{adip-/-}$ mice, respectively. Error bars are standard error of the mean. The x-axis is FFA species, and the y-axis is relative amount.
Figure 5K:
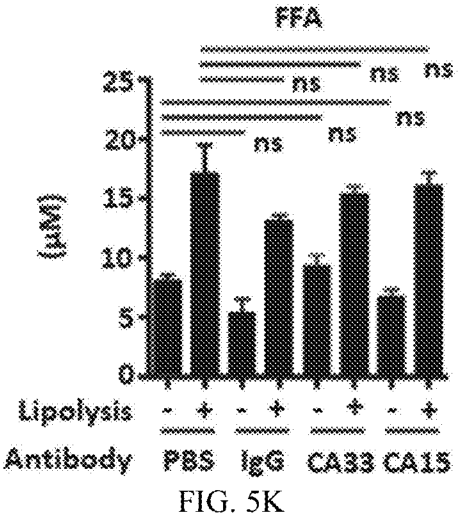
FIG. 5K is a bar graph that shows FFA release from 3T3L1 adipocyte treated with each antibody. n=3 in each condition. Error bars are standard error of the mean. The x-axis is treatment group, and the y-axis is micromolar FFA concentration.

The requirement for aP2 was assessed in two independent genetic models. Conditioned media from WAT explants from mice lacking both aP2 and mall ($Fabp^{-/-}$) lacked detectable activity to induce DNL in HepG2 cells independently of FFA release (see FIGS. 5D and 5E). In addition, a mouse model of inducible aP2 deletion was generated, in which the Fabp4 gene is humanized and flanked by loxP sites (FABP4, see FIG. 1E). FABP4 mice were crossed with AdipoQ-Cre/ERT2 mice to generate adipocyte-specific tamoxifen-inducible aP2 deficient mice ($FABP4^{adip-/-}$, see FIG. 5F). Similar to the experiment with $FABP^{-/-}$ mice, the conditioned medium from $FABP4^{adip-/-}$ mice adipose tissue explants lacked detectable activity to induce DNL in HepG2 cells, revealing that aP2 expression in the adipocytes was required for the effect of adipocyte lipolysis to induce DNL in hepatocytes (see FIGS. 5G and 5H). This model was also utilized to explore the physiological role of adipocyte-derived aP2 in regulating hepatic DNL in vivo. After induction of lipolysis by a 24 hr. fast, $FABP4^{adip-/-}$ mice displayed significantly reduced plasma aP2 levels compared to FABP4"littermate controls (see FIG. 1F), which correlated with increased phosphorylation of AMPK (Thr172) in the liver (see FIG. 1G) as well as decreased expression of lipogenic genes including Srebplc, Acly, and Acaca (see FIG. 1H). Direct analysis of hepatic DNL was performed by in vivo labeling with $^{3}H2O$ followed by lipid extraction (Dole et al., (1960) J. Biol. Chem. 235, 2595-2599; Galton (1968) J. Lipid Res. 9, 19-26). These experiments confirmed a significant reduction of hepatic lipogenesis in the $FABP4^{adip-/-}$ mice after a 22-hr fast (see FIG. 1I). Consistent with this finding, lipidomic analysis revealed a significant reduction in many of the FFA species including both saturated and unsaturated FFAs in the livers of $FABP4^{adip-/-}$ mice compared to controls (see FIG. 1J). Notably, in this model of inducible and adipocyte specific deletion of aP2, alterations in serum FFA species was not observed between genotypes, indicating that FFAs themselves were unlikely to serve as the adipocyte-derived signal (see FIG. 5J). These results demonstrate that adipocyte aP2 controls adipocyte lipolysis-induced hepatic DNL in vitro and in vivo.

Figure 1K:
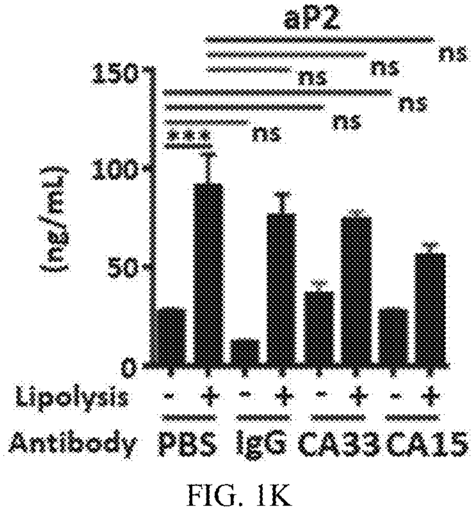
FIG. 1K is a bar graph that shows aP2 levels in the conditioned media from 3T3L1 adipocytes before and after 1 μM IBMX stimulation with various antibodies. n=3 for each condition. Error bars are standard error of the mean. The x-axis is treatment group, and the y-axis is aP2 level measured in nanograms per milliliter.
Figure 1L:
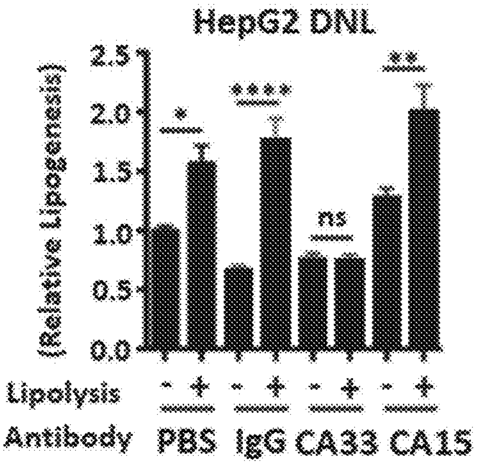
FIG. 1L is a bar graph that shows DNL in HepG2 cells treated with conditioned media from 3T3L1 adipocytes before and after 1 μM IBMX with various antibodies. DNL was analyzed by scintillation count, normalized to protein concentration and expressed relative to the basal condition n=4 in each condition. Error bars are standard error of the mean. The x-axis is treatment group, and the y-axis is relative lipogenesis.

Finally, to directly address the role of adipokine aP2 on the effect on hepatic DNL, antibody-based aP2 neutralization was tested in type 2 diabetes models to block induction of DNL in hepatocytes treated with conditioned media from lipolysis-stimulated adipocytes. The antibodies tested did not show any effect on either FFA release or aP2 secretion (see FIGS. 1K and 5L). However, it was found that the therapeutically active aP2 monoclonal antibody CA33 (Burak et al., (2015) Sci. Trans. Med. 7, 319ra205) completely prevented the induction of DNL by conditioned media from lipolysis stimulated adipocytes in HepG2 cells, while neither the non-active antibody CA15 (Burak et al., (2015) Sci. Trans. Med. 7, 319ra205) nor an IgG control antibody had any effect (see FIG. 1M). These data support the conclusion that adipokine aP2 secreted with lipolysis drives hepatic DNL.

Example 16

Mice with Adipose Tissue Specific aP2 Deficiency Show Reduced Hepatic DNL and Protection from Diet-Induced Hepatic Steatosis and Glucose Intolerance.

Figure 2A:
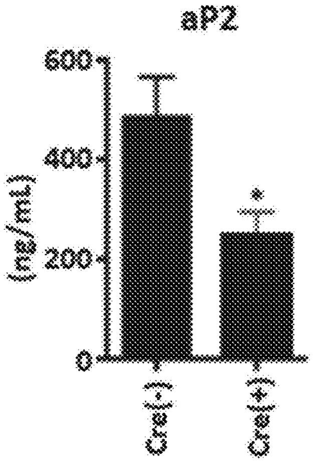
FIG. 2A is a bar graph that shows serum aP2 levels of FABP4$^{f/f}$ and FABP 4$^{adip—/—}$ mice fed HFD. n=10 and 11 for FABP4$^{f/f}$ and FABP 4$^{adip-/-}$ mice, respectively. Error bars are standard error of the mean. The x-axis is the treatment group, and the y-axis is aP2 level measured in nanograms per milliliter.
Figure 2B:
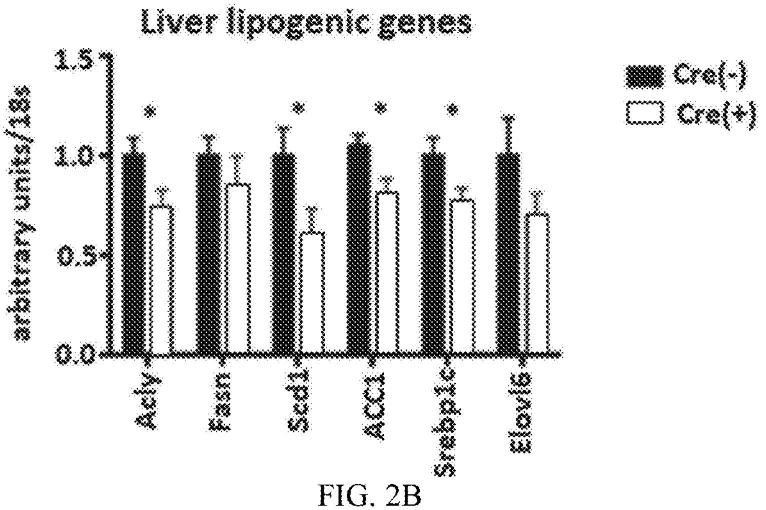
FIG. 2B is a bar graph that shows mRNA levels of lipogenic genes in the liver of FABP4$^{f/f}$ and FABP4$^{adip-/-}$ mice fed HFD. Expression levels were normalized to 18s rRNA and expressed relative to FABP4$^{f/f}$ mice. n=16 and 15 mice for FABP4$^{f/f}$ and FABP 4$^{adip—/—}$ mice, respectively. Error bars are standard error of the mean.
Figure 2C:
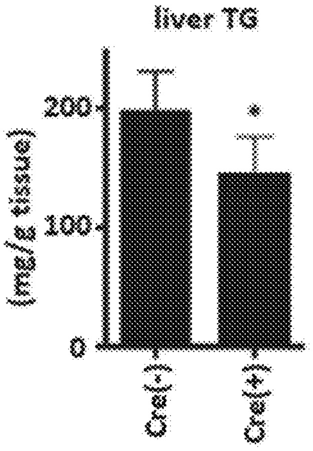
FIG. 2C is a bar graph that shows hepatic TG levels of FABP4$^{f/f}$ and FABP4$^{adip-/-}$ mice fed HFD. n=6 and 8 for FABP4$^{f/f}$ and FABP4$^{adip-/-}$ mice, respectively. Error bars are standard error of the mean. The x-axis is the treatment group, and the y-axis is hepatic TG levels measured in milligrams per gram of tissue.
Figure 2D:
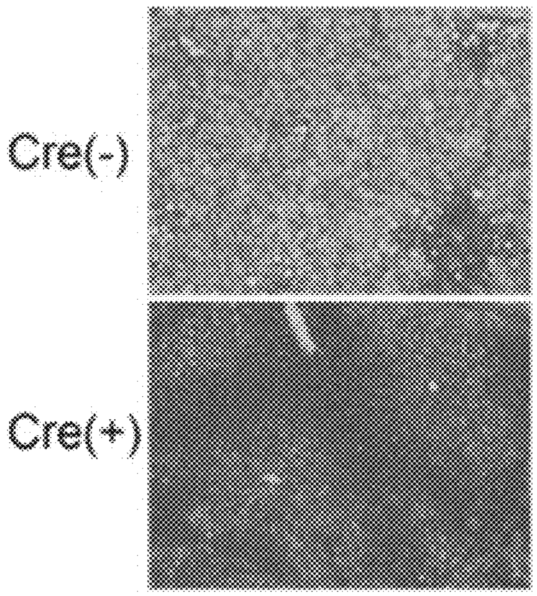
FIG. 2D shows liver histology of FABP4$^{f/f}$ and FABP4$^{adip-/-}$ mice fed HFD. Sections were stained with H&E.
Figure 2E:
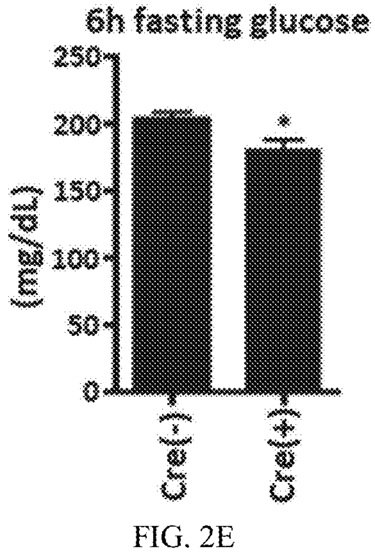
FIG. 2E is a bar graph that shows six hours fasting glucose levels in HFD-fed FABP4$^{f/f}$ and FABP4$^{adip-/-}$ mice. n=12 for each genotype. Error bars are standard error of the mean. The x-axis is treatment group, and the y-axis is fasting glucose measured in milligrams per deciliter.
Figure 2F:
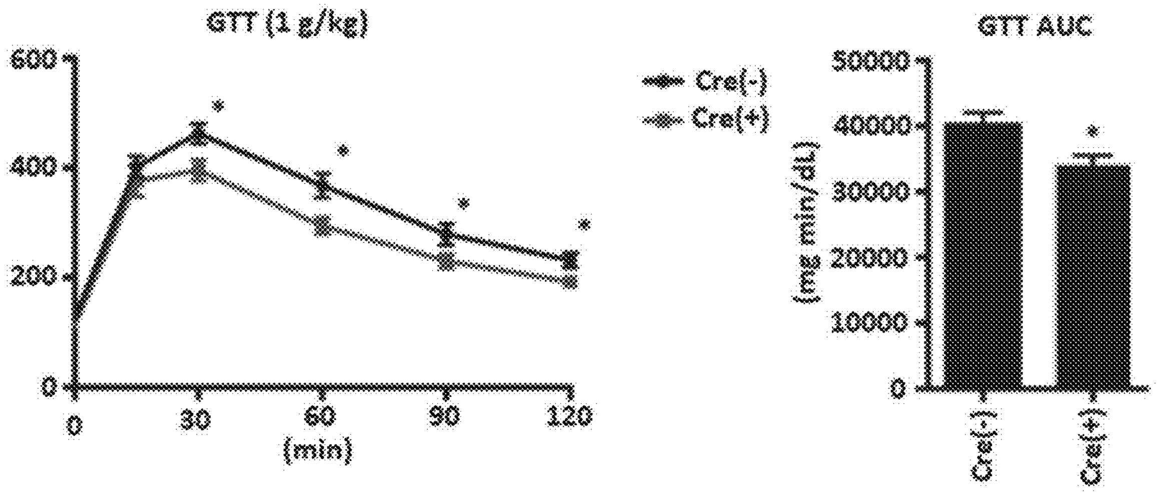
FIG. 2F is a line graph and a bar graph that show a glucose tolerance test (1 g/kg glucose) in FABP4$^{f/f}$ and FABP4$^{adip-/-}$ mice fed HFD. n=12 for each genotype.

In order to determine the role of adipocyte-derived aP2 in obesity-related liver dysfunction, FABP4 and $FABP4^{f/f}$; AdipoQ-Cre/ERT2 mice were fed HFD for 10 weeks and then adipocyte aP2 deletion was induced and metabolic parameters were analyzed 4-6 weeks later. Acute deletion of adipose tissue aP2 resulted in reduced serum aP2 (see FIG. 2A), reduced expression of lipogenic genes (see FIG. 2B), reduced hepatic triglyceride (TG) content (see FIG. 2C), and reduced hepatic steatosis (see FIG. 2D). These results demonstrate the significance of adipocyte-derived aP2 in hepatic DNL regulation and hepatic steatosis in obesity. Remarkably, acute aP2 deletion in adipocytes also improved glucose tolerance in HFD-fed mice, similar to what has been observed in the whole body Fabp4 deficiency (Hotamisligil et al., (1996) Science 274, 1377-1379) (see FIGS. 2E and 2F). These data are also consistent with the phenotype observed in HFD fed mice treated with the monoclonal antibody CA33 (Burak et al., (2015) Sci. Trans. Med. 7, 319ra205), supporting the conclusion that the phenotype of FABP4$^{adip-/-}$ mice is caused by the loss of endocrine action of aP2 as an adipokine.

Example 17 aP2 Binding Facilitates 2AG Signaling Through CB1R to Stimulate Hepatic DNL.

The data presented above indicate that adipocyte secretion of aP2 is required for lipolysis-mediated stimulation of hepatic DNL. However, addition of recombinant aP2 to conditioned media from 3T3L1 adipocytes with siRNA-mediated aP2 suppression was not sufficient to rescue DNL in HepG2 cells (see FIG. 6A), raising the possibility that an additional factor released from adipocytes during lipolysis may also be required for aP2's activity to promote hepatic DNL. As aP2 is a member of lipid chaperone fatty acid binding protein family, it was hypothesized that a specific lipid ligand may activate aP2 to promote hepatic DNL. To address this possibility, wild type (3T3L1) or Fabp-deficient adipocytes was pretreated with 10 μM BMS-309403, a cell-permeable high affinity synthetic molecule that occupies the fatty acid binding pocket of aP2 (Furuhashi et al., (2007) Nature 447, 959-965), starting 48 hours before the collection of conditioned media. Although BMS-309403 treatment did not alter FFA or aP2 secretion in this setting (see FIGS. 3A and 6B), it completely inhibited the ability of conditioned media from lipolysis-stimulated 3T3L1 adipocytes to induce DNL in HepG2 cells (see FIG. 3B). Importantly, when HepG2 cells were treated with conditioned media from Fabp-deficient adipocytes, pre-incubation with BMS-309403 exhibited no additional or Fabp-independent effect on DNL, indicating its on-target action through aP2 (see FIG. 3B).

Regarding the potential lipid ligands for Fabps, it was previously reported that Fabp isoforms present in the central nervous system (Fabp5 and Fabp7) directly bind with endocannabinoids and play significant roles in pain detection (Kaczocha et al., (2009) PNAS 106, 6375-6380; Kaczocha, et al., (2012) J. Biol. Chem. 287, 3415-3424; Kaczocha et al., (2014) PloS one 9, e94200). Endocannabinoids, namely anandamide (AEA) and 2-arachydonylglycerol (2-AG), are endogenous lipids that exert metabolic effects through ligand activity on cannabinoid receptors (Pacher et al., (2006) Pharmacological Rev. 58, 389-462; Maccarrone et al., (2015) Trends Pharma. Sci. 36, 277-296). Interestingly, action of the hepatic cannabinoid receptor 1 (CB1R) has been shown to stimulate DNL and play a significant role in the development of NAFLD and insulin resistance in obesity (Kunos et al., (2008) Gastroenterology 134, 622-625). The findings of decreased hepatic DNL, improved glucose tolerance, and increased hepatic AMPK activity in FABP4$^{adip-/-}$ mice are reminiscent of the reported phenotype of mice with hepatic deletion of CB1 (LCB1$^{-/-}$) (Osei-Hyiaman et al., (2008) J. Clin. Invest. 118, 3160-3169), and the effect of a peripheral CB1R antagonist (Tam et al., (2010) J. Clin. Invest. 120, 2953-2966). Furthermore, circulating levels of 2-AG significantly correlate with visceral fat area (Bluher et al., (2006) J Biol. Chem. 235, 2595-2599). It was therefore considered that the DNL-inducing action of adipocyte aP2 on liver may involve the protein in complex with an endocannabinoid ligand.

It was determined that the effect of adipocyte conditioned media on DNL and AMPK phosphorylation in hepatocytes required signaling through CB1. Indeed, treatment with Rimonabant, a well-established CB1 receptor antagonist, completely inhibited induction of DNL by conditioned media from lipolysis-stimulated 3T3L1 adipocytes, similarly to pretreatment with BMS-309403 (see FIG. 3C). These results indicate that the effect of adipocyte-secreted products on hepatic DNL, which requires aP2, is also dependent on intact CB1R signaling in the target cell.

To address the involvement of endocannabinoid systems in the protection against glucose tolerance and hepatic steatosis in FABP4$^{adip-/-}$ mice fed HFD, cannabinoid levels in plasma and tissues of these mice were explored. Interestingly, while FABP4$^{adip-/-}$ mice fed HFD exhibited significantly increased 2-AG and AEA levels in the serum, there was a trend toward reduced 2-AG and AEA levels in the liver compared to FABP4$^{fl/fl}$ (see FIG. 3D). On the other hand, there was no alteration in the level of endocannabinoids in adipose tissue (see FIG. 6C).

Figure 3D:
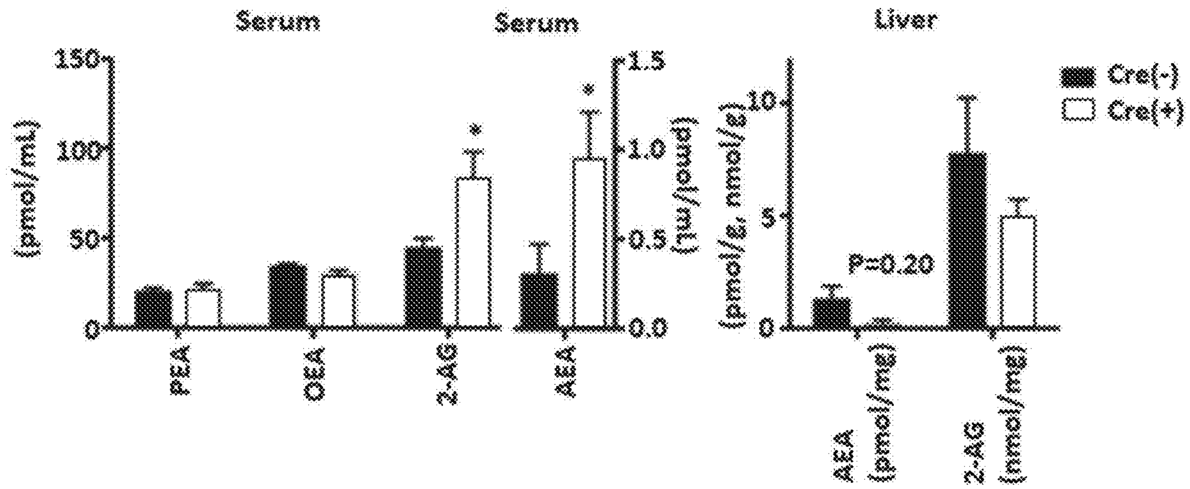
FIG. 3D are bar graphs that show endocannabinoid levels in serum and liver of FABP4$^{f/f}$ and FABP4$^{adip-/-}$ mice fed HFD. n=8 and 6 for FABP4$^{f/f}$ and FABP4$^{adip-/-}$ mice, respectively. Error bars are standard error of the mean.
Figure 3E:
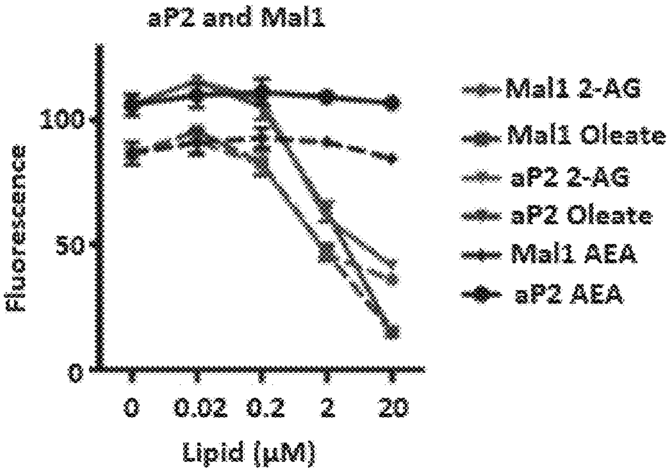
FIG. 3E is a line graph that shows the results of an ANS binding assay analyzing the binding of aP2 and mall to 2-AG, AEA, or oleate. n=3 for each data point. Error bars are standard error of the mean. The x-axis is micromolar lipid concentration, and the y-axis is fluorescence level.
Figure 3F:
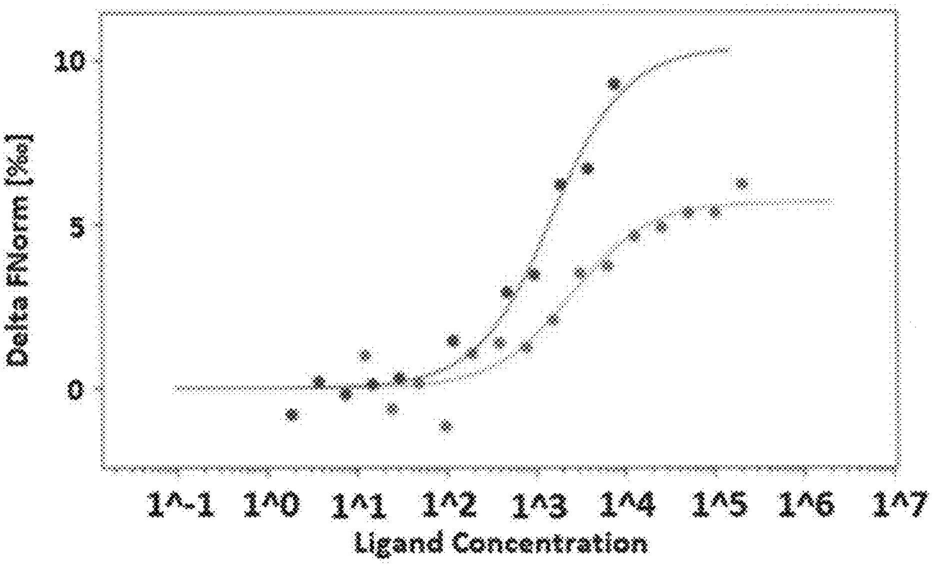
FIG. 3F is a line graph that shows the results of a Microscale Thermophoresis Assay analyzing the binding affinity of aP2 to 2-AG or oleate.
Figure 3G:
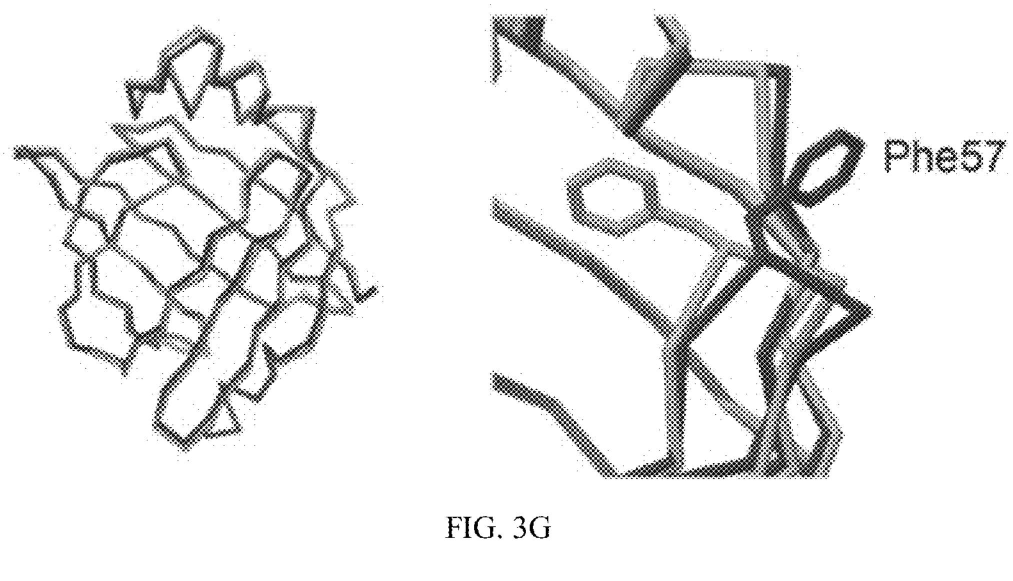
FIG. 3G shows a crystal structure of aP2 binding to 2-AG and comparison of apo FABP4 (PDB ID: 1ALB) and FABP4-2-AG complex.
Figure 3H:
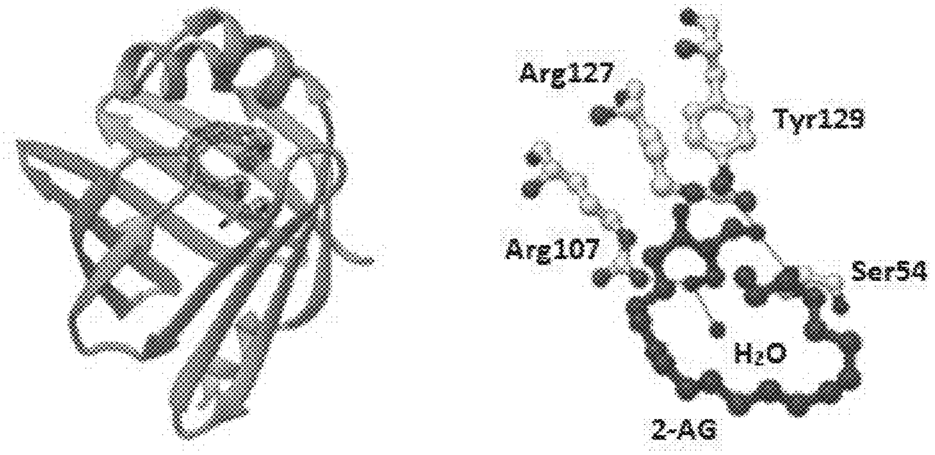
FIG. 3H shows the overall structure of FABP4-2-AG complex and hydrogen bond interactions of 2-AG. 2-AG is shown in 2Fo-Fc electron density contoured at 1.0σ.
Figure 3I:
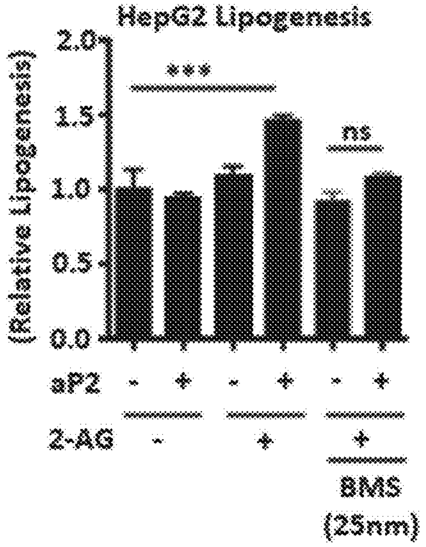
FIG. 3I is a bar graph that shows the effect of vehicle, aP2, 2-AG, or aP2/2-AG complex prepared with or without BMS-309403 on DNL in HepG2 cells. DNL was analyzed by scintillation count, normalized to protein concentration and expressed relative to the vehicle-treated condition. n=4 in each condition. Error bars are standard error of the mean. The x-axis is the treatment group, and the y-axis is relative lipogenesis.
Figure 3J:
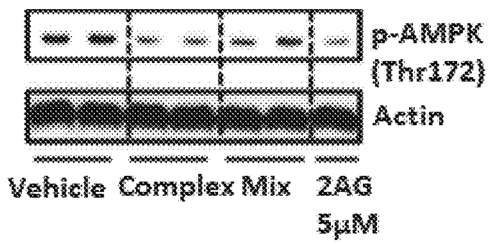
FIG. 3J is a western blot that shows the effect of vehicle, aP2/2-AG complex, mixture of aP2 and 2-AG, and 5 μM of 2-AG on AMPK phosphorylation in HepG2 cells.
Figure 3K:
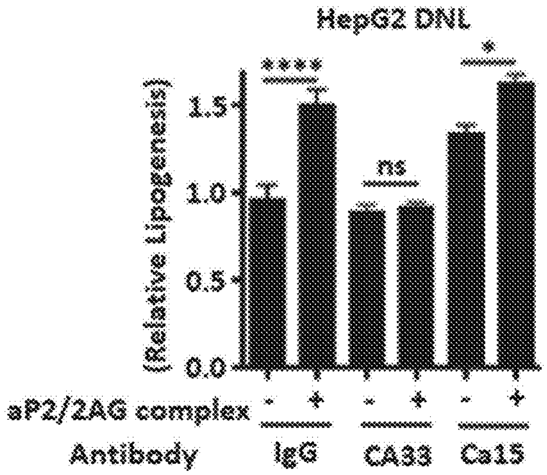
FIG. 3K is a bar graph that shows the effect of vehicle or aP2/2-AG complex incubated with IgG, CA33, or CA15 on DNL in HepG2 cells. DNL was analyzed by scintillation count, normalized to protein concentration and expressed relative to the vehicle-treated condition. n=4 in each condition of DNL analysis. Error bars are standard error of the mean. The x-axis is treatment group, and the y-axis is relative lipogenesis.

These analyses also revealed that 2-AG is 100-times more abundant than AEA in the serum (see FIG. 3D). It has been reported that both 2-AG and AEA have similar affinity for the CB1 receptor (Stella et al., (1997) Nature 388, 773-778; Felder et al., (1993) PNAS 90, 7656-7660), and only the level of 2-AG in serum is regulated in obesity (Bluher et al., (2006) Diabetes 55, 3053-3060). The potential interaction between 2-AG and aP2 was tested. In a substrate competition based assay utilizing 8-Anilinonaphthalene-1-sulfonic acid (ANS), it was found that aP2 binds to 2-AG at the same affinity as does mall (see FIG. 3E), which is a known 2-AG carrier protein in the CNS (Sanson et al., (2014) Biol. Crystallography 70, 290-298). As a complementary approach, a microscale thermophoresis assay (Jerabek-Willemsen et al., (2011) Assay and Drug Dev. Tech. 9, 342-353) was performed to examine direct physical interaction using fluorescence labeled purified aP2 protein and 2-AG, and found that aP2 directly binds to 2-AG with a Kd of 2.40/1, an affinity similar to that observed for oleate (see FIG. 3F). Finally, to resolve the mechanism and structural determinants of this interaction, aP2 and 2-AG was co-crystallized, confirming the ability of these two molecules to bind. In Ca superposition, the root mean square deviation (RMSD) between mouse 2-AG/FABP4 complex and apo mouse FABP4 structure was about 0.548 A (see FIG. 3G). Although this shows high similarity with unbound aP2 structures, the loop position where Phe57 resides was shifted about 1.3 A (see FIG. 3G). Due to steric hindrance of the acyl chain of 2-AG, the Phe57 side chain was modelled as open position in the complex structure. The polar head group of 2-AG was stabilized by hydrogen bond interactions with R127, R107, Y129 and S54 of FABP4 (see FIG. 3H).

Having established the capacity for direct 2-AG/aP2 interaction, additional functional experiments were performed to explore the biological significance of this relationship. aP2 complexed with 2-AG was produced by incubating delipidated recombinant aP2 in the presence of 2-AG and confirmed binding of 2-AG to aP2 by ANS assay (see FIG. 6E). It was found that the 2-AG/aP2 complex, but neither aP2 nor 2-AG alone stimulated DNL in HepG2 cells (see FIG. 3I). Remarkably, addition of BMS-309403 during 2-AG/aP2 complex formation eliminated the effect of 2-AG/aP2 complex on DNL, further supporting the conclusion that 2-AG binding to aP2 is functionally critical for the stimulation of DNL by aP2 (see FIG. 3I). How the 2-AG/aP2 complex modulates AMPK phosphorylation compared to the constituents alone was examined. Incubating HepG2 cells with the 2-AG/aP2 complex at the physiologically relevant concentration of 10 nM dephosphorylated AMPK (Thr172) to the same level that was achieved by incubation with a much higher concentration (5 μM) of 2-AG alone (see FIG. 3J). Importantly, a simple mixture of aP2 and 2-AG in which the two molecules had not formed a complex (see FIG. 3J) had no biological activity. Furthermore, it was also found that when the 2-AG/aP2 complex was formed in the presence of CA33, it lost its ability to regulate DNL in HepG2 cells, while incubation with control antibodies did not affect the activity of the complex (see FIG. 3K).

Figure 3L:
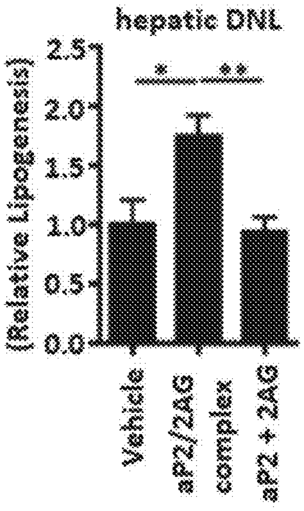
FIG. 3L is a bar graph that shows the effect of vehicle, aP2/2-AG complex, and mixture of aP2 and 2-AG i.p. injected to Fabp4/5 DKO mice fasted for 22 hrs on hepatic DNL. DNL was analyzed by scintillation count, normalized to tissue weight (mg) and expressed relative to the vehicle control. n=8, 9, and 9 mice for vehicle, aP2/2-AG complex, and aP2+2-AG injected group, respectively. Error bars are standard error of the mean. The x-axis is treatment group, and the y-axis is relative lipogenesis.

As these data strongly support that the 2-AG/aP2 complex has biological activity in cultured cells, the action of the 2-AG/aP2 complex was then assessed in vivo in mice. Previous research has demonstrated that physiological serum concentrations of endocannabinoids are too low to stimulate CB1R signaling (Pacher et al., (2006) Pharma. Rev. 58, 389-462; Friedman et al., (2008) Cell Metab. 7, 187-188). In line with this, it was found that concomitant injection of 2.2nmol each of aP2 and 2-AG did not alter hepatic DNL in FABP-deficient mice (see FIG. 3L). Remarkably, however, injection of the same amount of preformed 2-AG/aP2 complex led to robust induction of hepatic DNL in vivo (see FIG. 3L). These data provide strong support for a model in which aP2 binding facilitates and enables physiological concentrations of 2-AG to exert humoral function in the liver, identifying a unique endocrine network between liver and adipose tissue.

Example 18

Genetic Deletion of Adipocyte aP2 Expression or Antibody-Mediated aP2 Neutralization Ameliorates Atherosclerosis in $ApoE^{-/-}$ Mice Through Suppression of VLDL Production and Dyslipidemia.

Figure 4A:
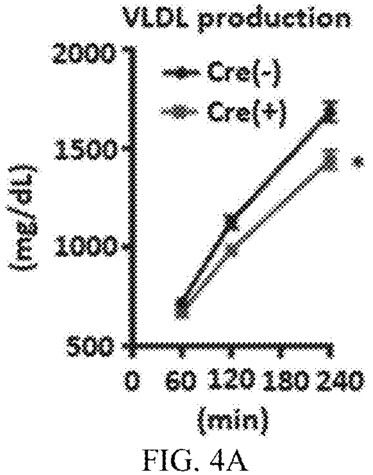
FIG. 4A is a line graph that shows VLDL production in lean $FABP4^{f/f}$ and $FABP4^{adip-/-}$ mice fasted for 18 hours. n=6 and 7 for $FABP4^{f/f}$ and FABP $4^{adip-/-}$ mice, respectively. *$p<0.05$. Error bars are standard error of the mean. The x-axis is time in minutes, and the y-axis is VLDL level in milligrams per deciliter.
Figure 4B:
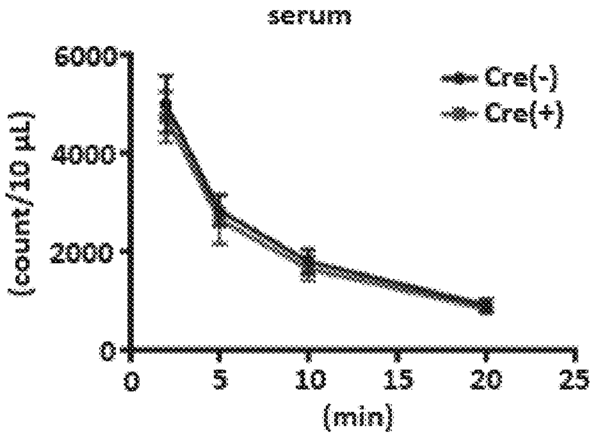
FIG. 4B is a line graph that shows the clearance rate of recombinant lipoprotein in lean $FABP4^{f/f}$ and $FABP4^{adip-/-}$ mice fasted for 18 hours. n=9 and 7 for $FABP4^{f/f}$ and $FABP4^{adip-/-}$ mice, respectively. Error bars are standard error of the mean. The x-axis is time in minutes, and the y-axis is counts per 10 microliters of serum.
Figure 4C:
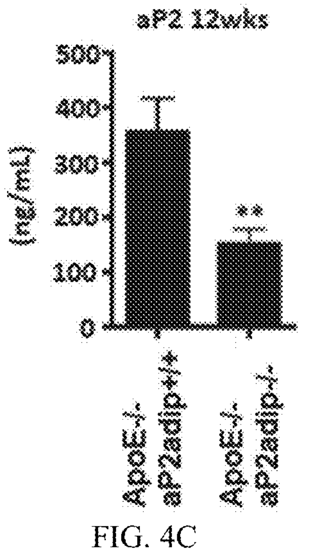
FIG. 4C is a bar graph that shows aP2 levels in $ApoE^{-/-}FABP4^{f/f}$ and $ApoE^{-/-}FABP4^{adip-/-}$ mice fed western diet for 12 weeks. n=17 for each genotype. Error bars are standard error of the mean. The x-axis is treatment group, and the y-axis is aP2 level in nanograms per milliliter.
Figure 4D:
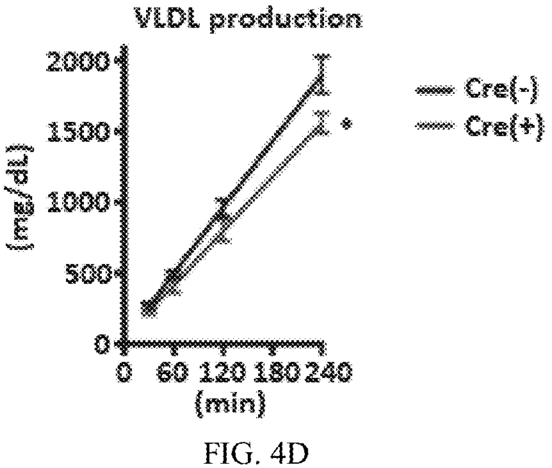
FIG. 4D is a line graph that shows VLDL production in $ApoE^{-/-}FABP4^{f/f}$ and $ApoE^{-/-}FABP4^{adip-/-}$ mice fed western diet for 2 weeks. n=5 and 8 for $ApoE^{-/-}FABP4^{f/f}$ and $ApoE^{-/-}FABP4^{adip-/-}$ mice, respectively. Error bars are standard error of the mean. The x-axis is time in minutes, and the y-axis is VLDL level in milligrams per deciliter.
Figure 4E:
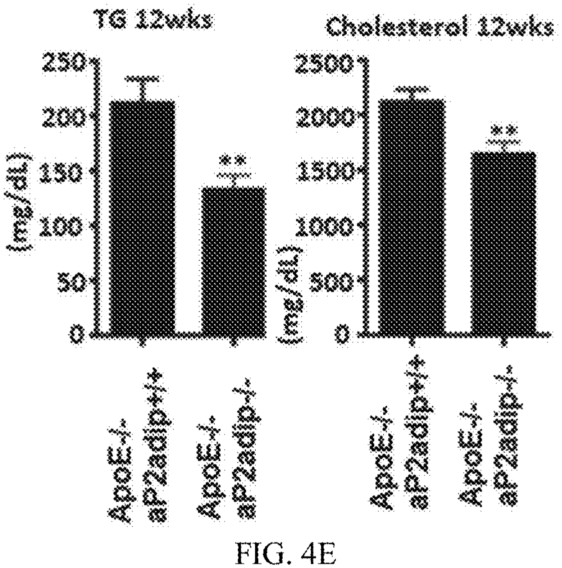
FIG. 4E are bar graphs that show TG and cholesterol levels in $ApoE^{-/-}FABP4^{f/f}$ and $ApoE^{-/-}FABP4^{adip-/-}$ mice fed western diet for 12 weeks. n=18 and 17 for $ApoE^{-/-}FABP4^{f/f}$ and $ApoE^{-/-}FABP4^{adip-/-}$ mice, respectively. Error bars are standard error of the mean. The x-axes are treatment groups, and the y-axes are TG and cholesterol levels, respectively, in milligrams per deciliter.
Figure 4F:
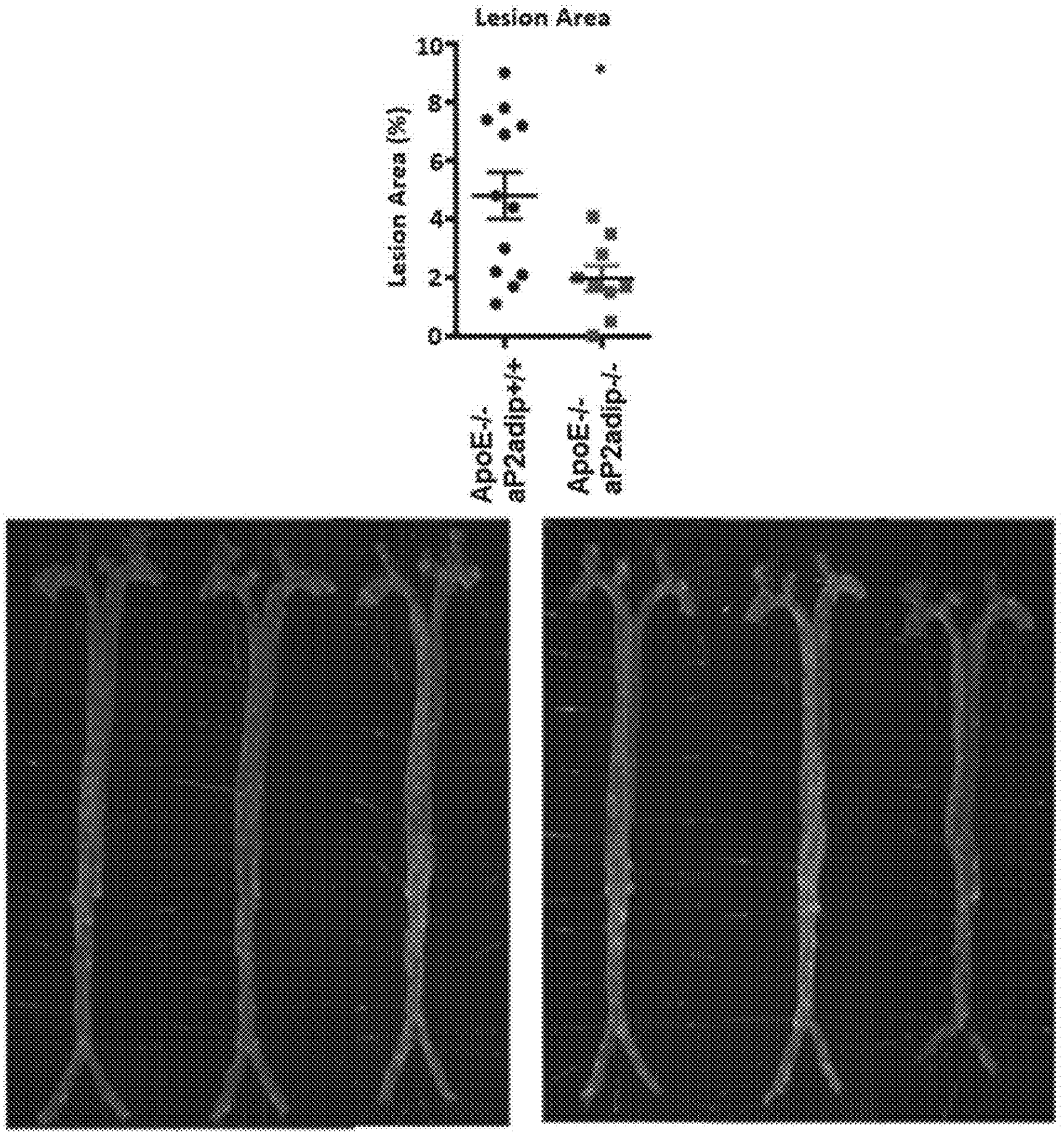
FIG. 4F shows the atherosclerotic lesion area of en face aortas from $ApoE^{-/-}FABP4^{f/f}$ and $ApoE^{-/-}FABP4^{adip-/-}$ male mice fed western diet for 12 weeks. n=12 and 10 mice for $ApoE^{-/-}FABP4^{f/f}$ and $ApoE^{-/-}FABP4^{adip-/-}$ mice, respectively. Error bars are standard error of the mean.
Figure 4G:
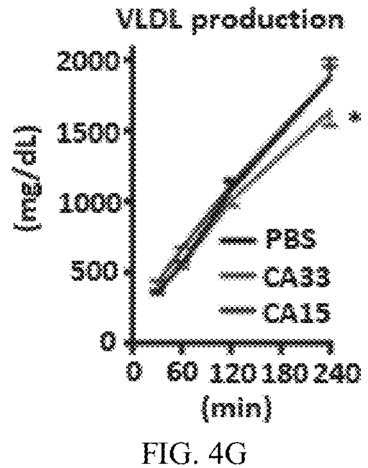
FIG. 4G is a line graph that shows VLDL production in $ApoE^{-/-}$ mice fed western diet and treated with PBS, CA33, or CA15 for 2 weeks. n=6, 8, and 4 for PBS, CA33 and CA15 respectively. *: comparison between PBS vs. CA33. Error bars are standard error of the mean. The x-axis is time in minutes, and the y-axis is VLDL level in milligrams per deciliter.
Figure 4H:
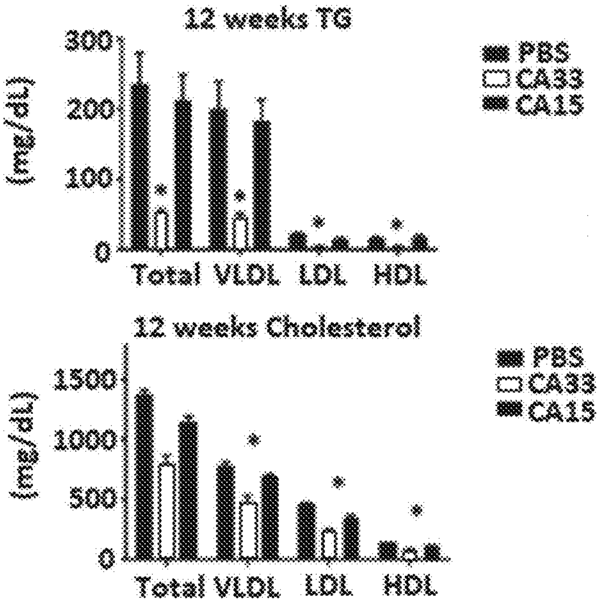
FIG. 4H are bar graphs that show the lipoprotein profile of $ApoE^{-/-}$ mice fed western diet and treated with PBS, CA33, or CA15 for 12 weeks. n=3 for each group. Error bars are standard error of the mean. The x-axis is lipoprotein type, and the y-axis is level in milligrams per deciliter.
Figure 4I:
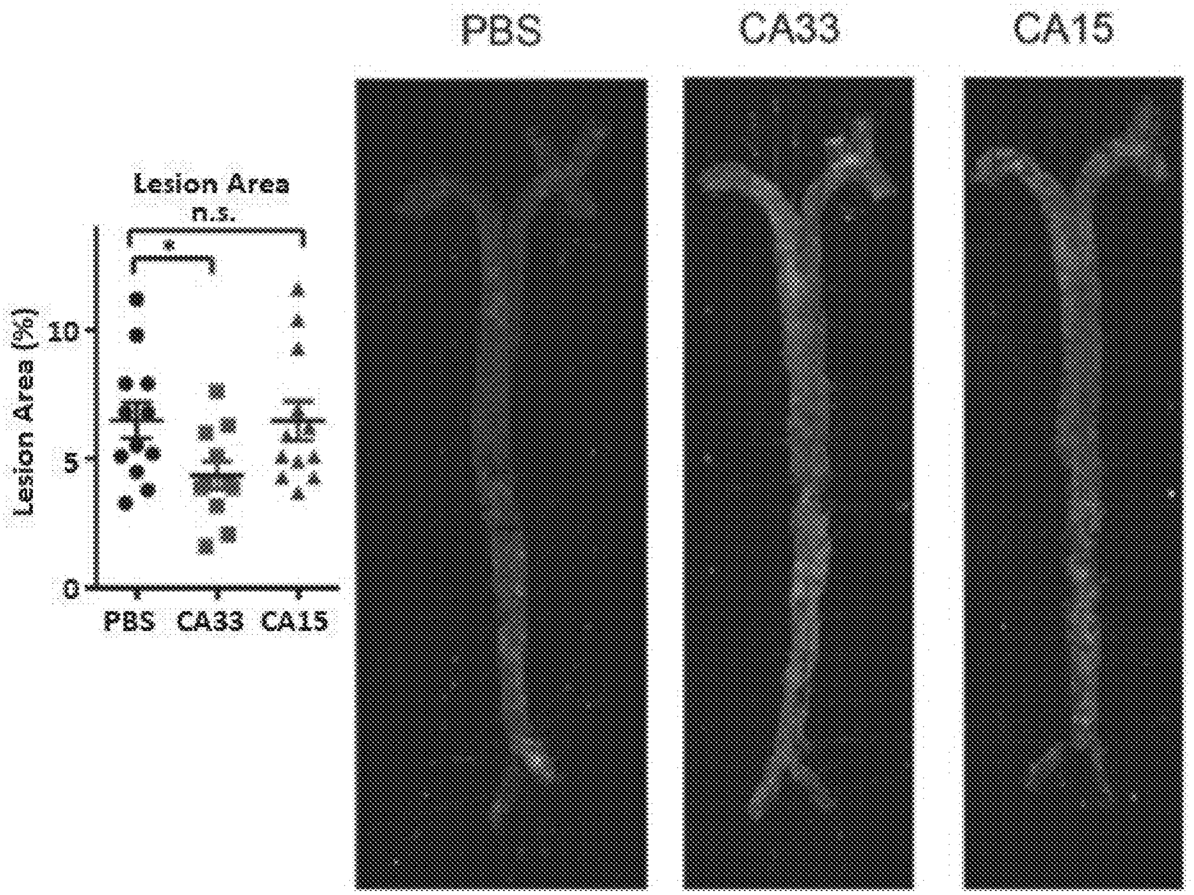
Figure 7A:
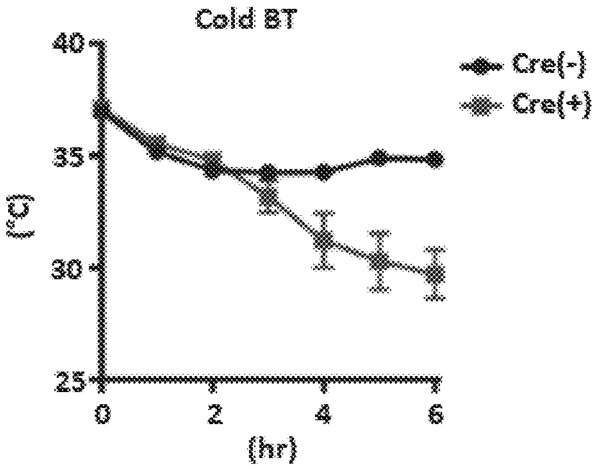
FIG. 7A is a line graph that shows the core body temperature of the $FABP4^{f/f}$ and $FABP4^{adip-/-}$ mice fasted for 18 hrs. n=8 for each genotype. Error bars are standard error of the mean. The x-axis is time in hours, and the y-axis is temperature measured in Celsius.
Figure 7B:
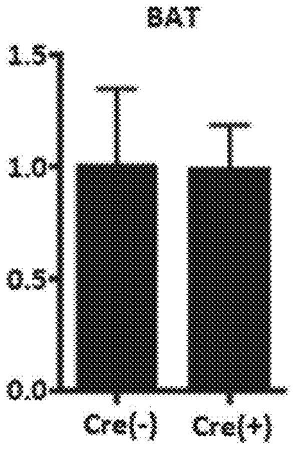
FIG. 7B is a bar graph that shows lipoprotein uptake in brown adipose tissue (BAT) in lipoprotein clearance test. n=9 and 7 for $FABP4^{f/f}$ and $FABP4^{adip-/-}$ mice, respectively. Error bars are standard error of the mean.
Figure 7C:
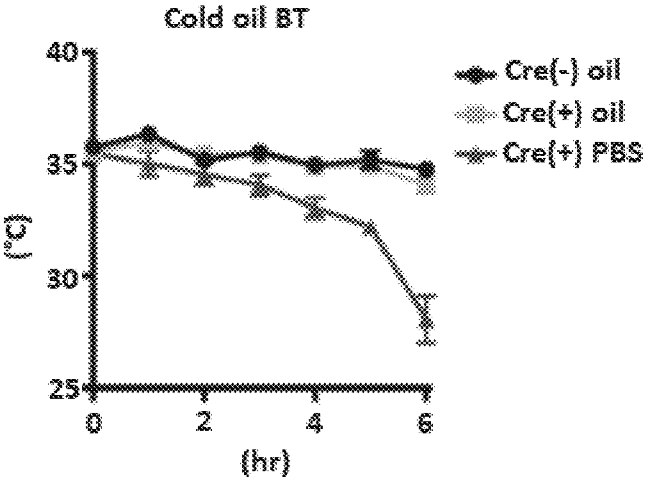
FIG. 7C is a line graph that shows core body temperature of the $FABP4^{f/f}$ and $FABP4^{adip-/-}$ mice fasted for 18 hrs, fed with or without 200p1 olive oil before the cold exposure. n=4 for each condition. Error bars are standard error of the mean. The x-axis is time in hours, and the y-axis is temperature measured in Celsius.
Figure 7D:
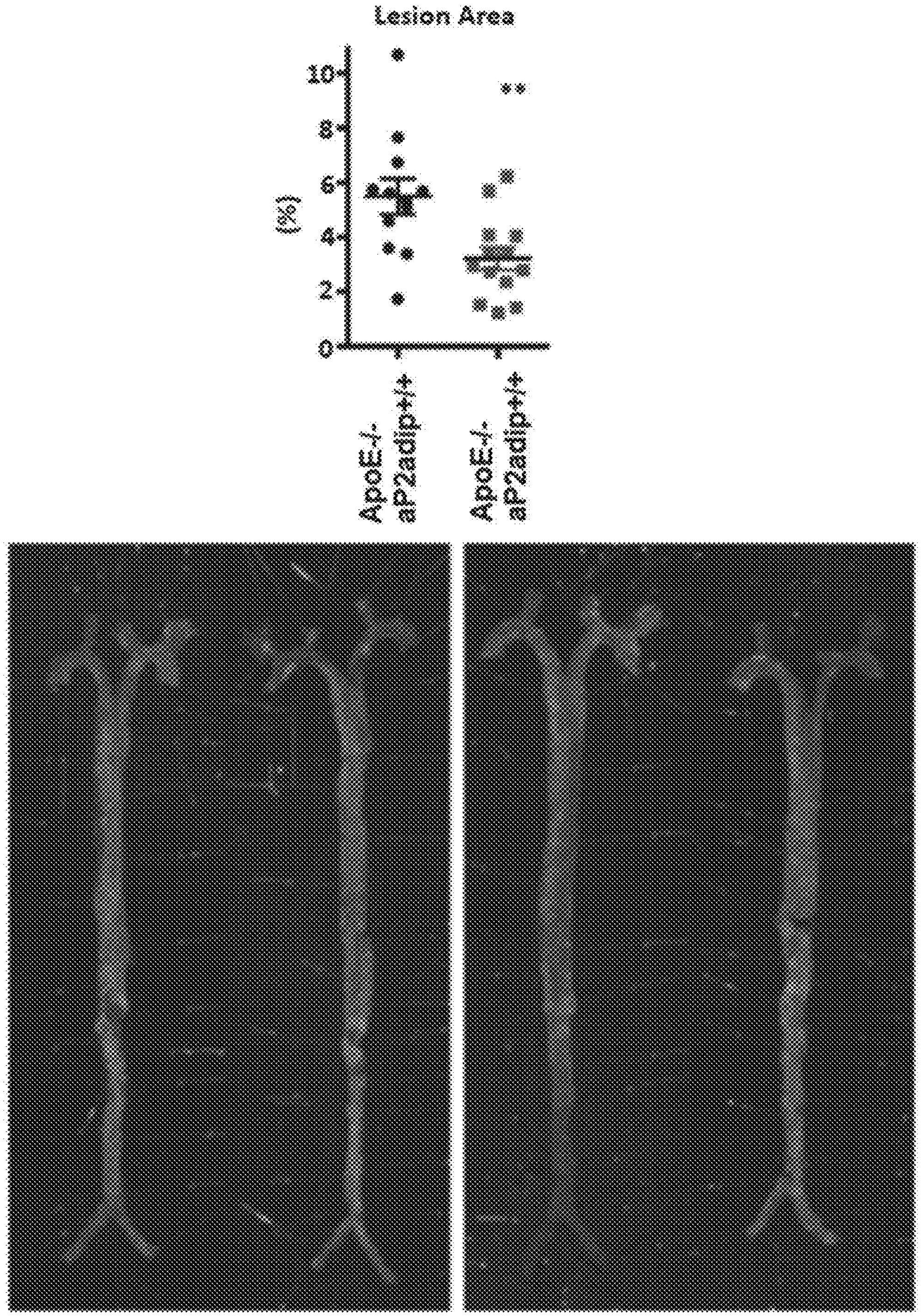
FIG. 7D shows the atherosclerotic lesion area of en face aortas from $ApoE^{-/-}$FABP $4^{f/f}$ and $ApoE^{-/-}FABP4^{adip-/-}$ female mice fed western diet for 12 weeks. n=12 and 13 mice for $ApoE^{-/-}$FABP $4^{f/f}$ and $ApoE^{-/-}FABP4^{adip-/-}$ mice, respectively. Error bars are measured in standard error of the mean.
Figure 7E:
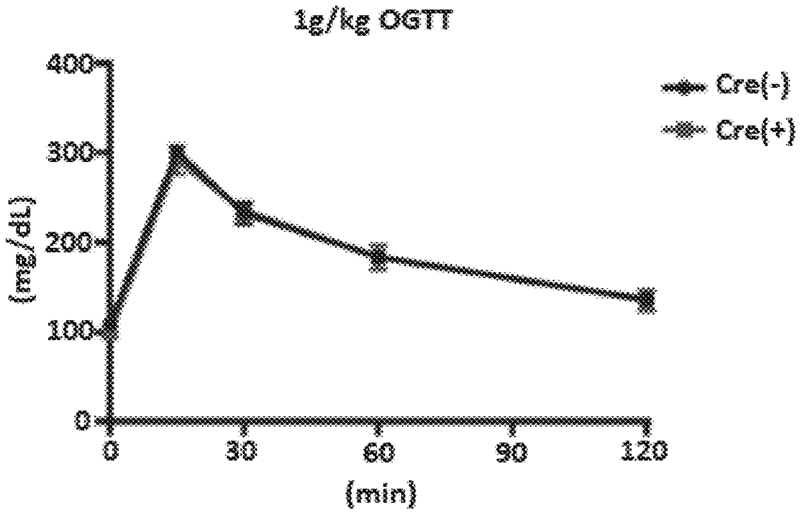
FIG. 7E is a line graph that shows the results of a glucose tolerance test (1 g/kg glucose) in $ApoE^{-/-}$FABP $4^{f/f}$ and $ApoE^{-/-}FABP4^{adip-/-}$ mice fed WD. n=11 and 8 mice for $ApoE^{-/-}$FABP $4^{f/f}$ and $ApoE^{-/-}FABP4^{adip-/-}$ mice.
Figure 7F:
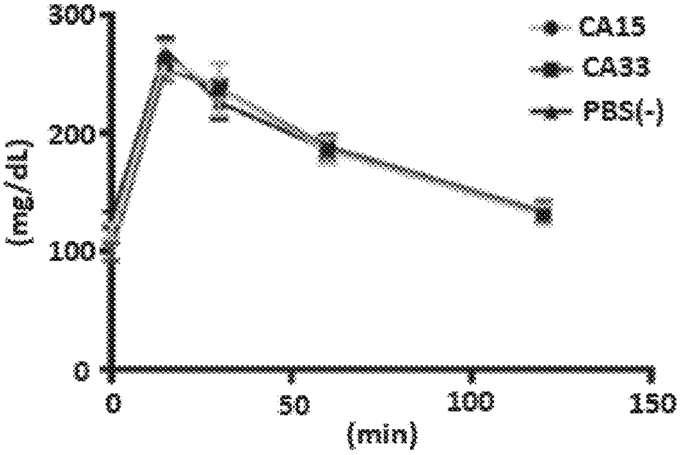
FIG. 7F is a line graph that shows the results of a glucose tolerance test (1 g/kg glucose) in $ApoE^{-/-}$ mice fed WD and treated with PBS, CA33, or CA15. n=8, 8, and 7 mice for PBS, CA33, or CA15 treatment, respectively.
Figure 7G:
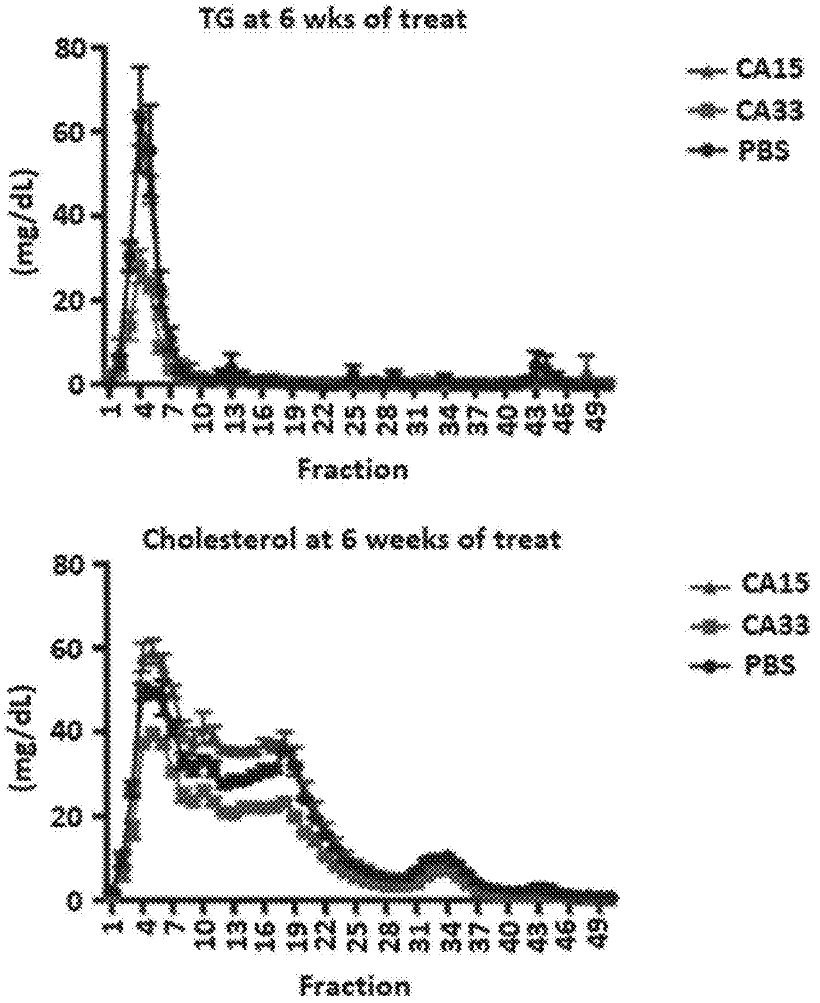
FIG. 7G are line graphs that show the lipoprotein profile of $ApoE^{-/-}$ mice fed western diet and treated with PBS, CA33, or CA15 for 6 weeks. n=3 for each group. Error bars are standard error of the mean. The x-axis is fraction collected, and the y-axis is TG or cholesterol level, respectively, measured in milligrams per deciliter.
Figure 8:
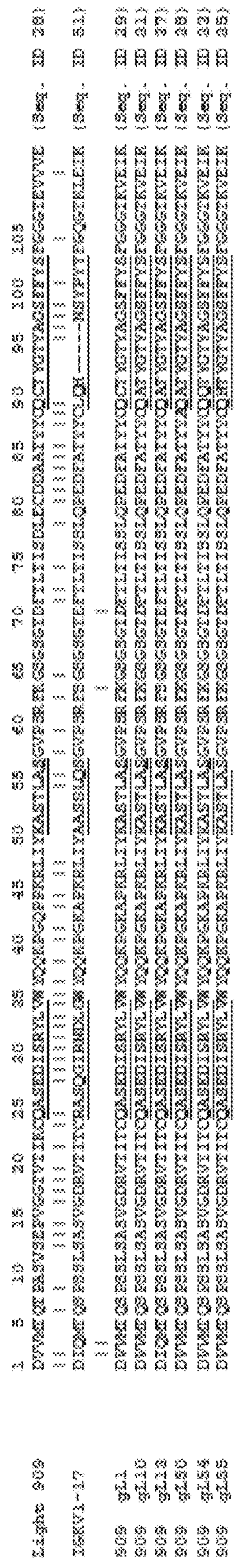
FIG. 8 provides anti-human aP2 humanized kappa light chain variable region antibody fragments, wherein the 909 sequence is rabbit variable light chain sequence, and the 909 gL1, gL10, gL13, gL50, gL54, and gL55 sequences are humanized grafts of 909 variable light chain using IGKV1-17 human germline as the acceptor framework. The CDRs are shown in bold/underlined, while the applicable donor residues are shown in bold/italic and are highlighted: 2V, 3V, 63K and 70D. The mutation in CDRL3 to remove a Cysteine residue is shown in bold/underlined and is highlighted: 90A.
Figure 9:
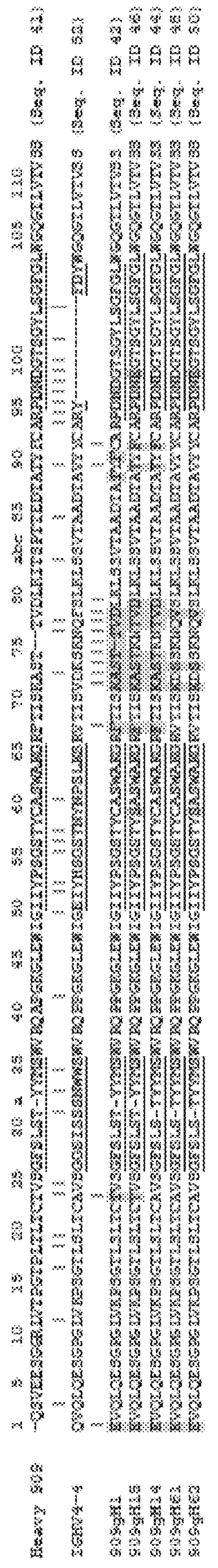
FIG. 9 provides anti-human aP2 humanized heavy chain variable region antibody fragments, wherein the 909 sequence is rabbit variable heavy chain sequence, and the 909gH1, gH14, gH15, gH61, and gH62 sequences are humanized grafts of 909 variable heavy chain using IGHV4-4 human germline as the acceptor framework. The CDRs are shown in bold/underlined. The two-residue gap in framework 3, in the loop between beta sheet strands D and E, is highlighted in gH1: 75 and 76. Applicable donor residues are shown in bold/italic and are highlighted: 23T, 67F, 71K, 72A, 73S, 74T, 77T, 78V, 79D, 89T, and 91F. The mutation in CDRH2 to remove a Cysteine residue is shown in bold/underlined and is highlighted: 59S. The mutation in CDRH3 to remove a potential Aspartate isomerization site is shown in bold/underlined and is highlighted: 98E. The N-terminal Glutamine residue is replaced with Glutamic acid and is shown in bold and highlighted: 1E. The rabbit 909 heavy and light chain comprise CA33.

Genetic studies indicate a strong connection between hepatic DNL, VLDL production and CVD risk (Teslovich et al., (2010) Nature 466, 707-713; Global Lipids Genetics et al., (2013) Nat. Genetics 45, 1274-1283). Also, the circulating levels of both endocannabinoids and aP2 are significantly elevated in patients with coronary artery disease (Sugamura et al., (2009) Circ. 119, 28-36). As it was found that the 2-AG/aP2 complex is a novel and critical component of adipose tissue-liver endocrine network that regulates hepatic DNL its influence on the VLDL production and CVD pathogenesis was explored. To this end VLDL production in response to fasting in $FABP4^{f/f}$ and $FABP4^{adip-/-}$ mice was compared. VLDL production was significantly decreased in $FABP4^{adip-/-}$, demonstrating that adipocyte-derived aP2 enhances VLDL production (see FIG. 4A). As hepatic VLDL-TG production supplies the periphery with nutrients during fasting and stress and aP2 is secreted in response to sympathetic nerve stimulation including fasting, the response of $FABP4^{adip-/-}$ mice to cold exposure after fasting, during which VLDL production is required to fuel adaptive thermogenesis (Bartelt et al., (2011) Nat. Med. 17, 200-205) was explored. Indeed, $FABP4^{adip-/-}$ mice were significantly more sensitive to cold after fasting as their core body temperature dropped faster after the exposure compared to $FABP4^{fl/fl}$ mice (see FIG. 7A). Notably, this effect was independent of difference in lipoprotein clearance and uptake into brown adipose tissue (see FIGS. 4B and 7B). Remarkably, oral administration of 200 μl of olive oil, which supplies triglycerides as chylomicrons produced by the intestine, completely rescued the cold intolerance of $FABP4^{adip-/-}$ mice (see FIG. 7C), demonstrating that an insufficient supply of VLDL underlies the cold intolerance in this model.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A method of selecting a compound capable of binding 2-arachidonylglycerol/adipocyte binding protein complex (2-AG/aP2) for use in treating a human subject with a disorder mediated by the dysregulation of de novo lipogenesis (DNL) comprising:

i. contacting the compound with 2-AG/aP2, wherein the compound is an antibody, antibody fragment, or antigen binding agent that has been humanized;

ii. determining whether the compound binds to 2-AG/aP2 with a KD of less than or equal to $10^{-9}$ M; and iii. the compound binds to the 2-AG/aP2 complex with a KD of less than or equal to $10^{-9}$ M, selecting the compound.

2. The method of claim 1, further comprising:

i. introducing the compound selected in claim 1, into a first cellular assay in the presence of 2-AG and aP2, and/or 2-AG/aP2, wherein the first cellular assay includes a population of cells expressing cannabinoid receptor type-1 (CB1);

ii. measuring the biological activity of CB1 in the first cellular assay;

iii. measuring the biological activity of CB1 in a second cellular assay in the presence of 2-AG and aP2, and/or 2-AG/aP2, wherein the second cellular assay includes a population of cells expressing CB1;

iv. comparing the biological activity of CB1 in the first cellular assay and second cellular assay, wherein the CB1 biological activity is selected from suppression of downstream AMPK phosphorylation, phosphorylation of mitogen-activated protein kinases (MAPK), increased de novo lipogenesis (DNL) production, increased very low-density lipoprotein (VLDL) production, inhibition of cyclic AMP formation, or a combination thereof; and, v. if CB1 biological activity is reduced in the first cellular assay compared to the second cellular assay, selecting the compound.

3. The method of claim 2, wherein the cell population expressing CB1 is a population of human hepatocytes.

4. A method of selecting a compound capable of neutralizing 2-AG/aP2 agonism of CB1 for use in treating a human subject with a disorder mediated by the dysregulation of de novo lipogenesis (DNL) comprising:

i. contacting the compound with 2-AG/aP2, wherein the compound is an antibody, antibody fragment, or antigen binding agent that has been humanized;

ii. determining whether the compound binds to 2-AG/aP2 with a KD of less than or equal to $\mathbf{10}^{-9}$ M;

iii. if the compound binds to the 2-AG/aP2 complex with a KD of less than or equal to $10^{-9}$ M, introducing the compound into an assay with 2-AG and aP2, or 2-AG/aP2, and CB1;

iv. determining whether 2-AG/aP2 binds to CB1; and, v. if non-binding of 2-AG/aP2 to CB1 is observed, selecting the compound.

5. The method of claim 4, further comprising:

i. introducing the compound selected in claim 4 into a first cellular assay in the presence of 2-AG and aP2, and/or 2-AG/aP2, wherein the cellular assay includes a population of cells expressing CB1;

ii. measuring the biological activity of CB1 in the first cellular assay;

iii. measuring the biological activity of CB1 in a second cellular assay in the presence of 2-AG and aP2, and/or 2-AG/aP2, wherein the second cellular assay includes a population of cells expressing CB1;

iv. comparing the biological activity of CB1 in the first cellular assay and second cellular assay, wherein the CB1 biological activity is selected from suppression of downstream AMPK phosphorylation, phosphorylation of mitogen-activated protein kinases (MAPK), increased de novo lipogenesis (DNL) production, increased very low-density lipoprotein (VLDL) production, inhibition of cyclic AMP formation, or a combination thereof; and, v. if CB1 biological activity is reduced in the first cellular assay compared to the second cellular assay, selecting the compound.

6. The method of claim 5, wherein the cell population expressing CB1 is human hepatocytes.

* * * * *